US011124559B2

(12) United States Patent
Despanie et al.

(10) Patent No.: US 11,124,559 B2
(45) Date of Patent: Sep. 21, 2021

(54) GENERATION OF HEMOGLOBIN-BASED OXYGEN CARRIERS USING ELASTIN-LIKE POLYPEPTIDES

(71) Applicant: University of Southern California, Los Angeles, CA (US)

(72) Inventors: Jordan Tremaine Despanie, South Pasadena, CA (US); Hao Guo, Alhambra, CA (US); John Andrew MacKay, San Gabriel, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 16/206,896

(22) Filed: Nov. 30, 2018

(65) Prior Publication Data

US 2020/0062825 A1  Feb. 27, 2020

Related U.S. Application Data

(63) Continuation of application No. 14/965,053, filed on Dec. 10, 2015, now abandoned.

(60) Provisional application No. 62/089,885, filed on Dec. 10, 2014.

(51) Int. Cl.
  *A61K 38/42* (2006.01)
  *C07K 14/78* (2006.01)
  *C07K 14/805* (2006.01)

(52) U.S. Cl.
  CPC ............ *C07K 14/805* (2013.01); *A61K 38/42* (2013.01); *C07K 14/78* (2013.01); *C07K 2319/00* (2013.01)

(58) Field of Classification Search
  None
  See application file for complete search history.

(56) References Cited

U.S. PATENT DOCUMENTS

| | | |
|---|---|---|
| 4,898,926 A | 2/1990 | Urry |
| 6,015,662 A | 1/2000 | Hackett et al. |
| 6,852,834 B2 | 2/2005 | Chilkoti |
| 7,829,681 B2 | 11/2010 | Seefeldt et al. |
| 8,252,740 B2 | 8/2012 | Raucher et al. |
| 8,367,626 B2 | 2/2013 | Furgeson et al. |
| 8,563,521 B2 | 10/2013 | Skerra et al. |
| 8,680,045 B2 | 3/2014 | Primiano et al. |
| 8,841,137 B2 | 9/2014 | Delouise et al. |
| 8,841,414 B1 | 9/2014 | Raucher et al. |
| 8,933,197 B2 | 1/2015 | Stemmer et al. |
| 9,102,763 B2 | 8/2015 | MacKay et al. |
| 2004/0254108 A1 | 12/2004 | Ma et al. |
| 2007/0265197 A1 | 11/2007 | Furgeson et al. |
| 2008/0312156 A1 | 12/2008 | Setton et al. |
| 2010/0048473 A1 | 2/2010 | Chaikof et al. |
| 2010/0119529 A1 | 5/2010 | Furgeson et al. |
| 2010/0189643 A1 | 7/2010 | Chilkoti et al. |
| 2011/0039776 A1 | 2/2011 | Chilkoti |
| 2011/0110866 A1 | 5/2011 | Chilkoti et al. |
| 2011/0151006 A1 | 6/2011 | Weber et al. |
| 2012/0213781 A1 | 8/2012 | Hilbert |
| 2013/0196926 A1 | 8/2013 | MacKay et al. |
| 2013/0210747 A1 | 8/2013 | Hamm-Alvarez et al. |
| 2014/0294932 A1 | 10/2014 | Kim et al. |
| 2015/0209335 A1 | 7/2015 | MacKay et al. |
| 2015/0218280 A1 | 8/2015 | Epstein et al. |
| 2015/0238431 A1 | 8/2015 | Hamm-Alvarez et al. |
| 2016/0017004 A1 | 1/2016 | Hamm-Alvarez et al. |
| 2016/0168228 A1 | 6/2016 | Despanie |
| 2020/0079868 A1 | 3/2020 | Epstein et al. |

FOREIGN PATENT DOCUMENTS

| | | |
|---|---|---|
| JP | 2006-182721 A | 7/2006 |
| WO | WO-96/32406 | 10/1996 |
| WO | WO-2008/033847 | 3/2008 |
| WO | WO 2010/144612 | 12/2010 |
| WO | WO-2011/006069 A1 | 1/2011 |
| WO | WO-2011/133635 | 10/2011 |
| WO | WO-2014/059384 A2 | 4/2014 |
| WO | WO-2014/161004 | 10/2014 |
| WO | WO-2017/020686 A1 | 2/2017 |

OTHER PUBLICATIONS

Amiram M et al: "A depot-forming glucagon-like peptide-1 fusion protein reduces blood glucose for five days with a single injection", Journal of Controlled Release, vol. 172, No. 1 , pp. 144-151, XP028772905, ISSN: 0168-3659, DOI: 10.1016/J.JCONREL.2013.07.021.

Andre F. Palmer et al: "Blood Substitutes", Annual Review of Biomedical Engineering, vol. 16, No. 1, Jul. 11, 2014 (Jul. 11, 2014), pp. 77-101, XP055202930, ISSN: 1523-9829, DOI: 10.1146/annurev-bioeng-071813-104950.

Chang, T. M. S., "Modified hemoglobin-based blood substitutes: crosslinked, recombinant and encapsulated hemoglobin", Vox Sanguinis, 1998, vol. 74 (Suppl. 2), pp. 233-241.

Chilkoti A et al: "Stimulus responsive elastin biopolymers: applications in medicine and biotechnology", Current Opinion in Chemical Biology, Current Biology Ltd, London, GB, vol. 10, No. 6, Dec. 1, 2006 (Dec. 1, 2006), pp. 652-657, XP028014524, ISSN: 1367-5931, DOI: 10.1016/J.CBPA.2006.10.010 [retrieved on Dec. 1, 2006].

(Continued)

*Primary Examiner* — Julie Ha
*Assistant Examiner* — Kristina M Hellman
(74) *Attorney, Agent, or Firm* — Foley & Lardner LLP

(57) ABSTRACT

Described herein is the use of elastin-like polypeptides to generate hemoglobin-based oxygen carriers as a means of preventing and treating conditions caused by blood loss or anemia, for example, hemorrhagic shock. Elastin-like polypeptides are capable of creating therapeutically functional fusion proteins through genetic engineering with a therapeutic agent, for example, hemoglobin and biologic equivalent thereof. Specific forms of these fusion proteins have the ability to form into spherical nanoparticles possessing a therapeutically agent at their core. This provides a unique basis for employing elastin-like polypeptides as hemoglobin carriers in the manufacture of blood substitutes.

14 Claims, 11 Drawing Sheets

Specification includes a Sequence Listing.

(56) References Cited

OTHER PUBLICATIONS

Database Geneseq [Online] Jun. 19, 2014 (Jun. 19, 2014), "ELP component reference polypeptide construct S48I48, SEQ ID 4 #1.", retrieved from EBI accession No. GSP:BBF47655 Database accession No. BBF47655.

Doreen Manuela Floss et al: "Expression and Immunogenicity of the Mycobacterial Ag85B/ESAT-6 Antigens Produced in Transgenic Plants by Elastin-Like Peptide Fusion Strategy", Journal of Biomedicine and Biotechnology, vol. 2010, Jan. 1, 2010 (Jan. 1, 2010), pp. 1-14, XP055476450, US, ISSN: 1110-7243, DOI: 10.1155/2010/274346.

Extended European Search Report dated Jun. 8, 2018, from application No. 15867997.7.

Giselle C. Yeo et al: "Fabricated Elastin", Advanced Healthcare Materials, vol. 4, No. 16, Nov. 1, 2015 (Nov. 1, 2015), pp. 2530-2556, XP055330918, DE, ISSN: 2192-2640, DOI: 10.1002/adhm.201400781.

Hassouneh, Wafa et al., "Fusions of elastin-like polypeptides to pharmaceutical proteins", Methods in Enzymology, 2012, vol. 502, pp. 215-237, NIH Public Access Author Manuscript Version internal p. 1-24.

International Search Report and Written Opinion dated Apr. 12, 2016, from application No. PCT/US2015/064938.

NCBI, GenBank accession No. AAB59408.1 (Aug.10, 2004).

NCBI, GenBank accession No. NM_000558.3 (May 24, 2014).

Shi Pu et al: "Elastin-based protein polymer nanoparticles carrying drug at both corona and core suppress tumor growthin vivo", Journal of Controlled Release, vol. 171, No. 3 , pp. 330-338, XP028740202, ISSN: 0168-3659, DOI: 10.1016/J.JCONREL.2013.05.013.

UnitProt Accession No. P68871, accessed May 28, 2018 at URL. unitprot.org/unitprot/ P68871.

UnitProt Accession No. P69891, accessed May 28, 2018 at URL. unitprot.org/unitprot/ P69891.

UnitProt Accession No. P69905, accessed May 28, 2018 at URL. unitprot.org/unitprot/ P69905.

U.S. Non-final Office Action dated Jun. 1, 2018, from U.S. Appl. No. 14/965,053.

Awasthi et al., "Biodistribution of Radioiodinated Adenovirus Fiber Protein Knob Domain after Intravenous Injection in Mice.," J. Virol., vol. 78, No. 12, Jun. 2004, pp. 6431-6438.

Chilkoti et al., "Design of thermally responsive, recombinant polypeptide carriers for targeted drug delivery." Advanced Drug Delivery Reviews, vol. 54, No. 8, 2002, pp. 1093-1111.

Despanie et al. "Elastin-like polypeptides: Therapeutic applications for an emerging class of nanomedicines," J Control Release, vol. 240, Nov. 11, 2015, pp. 93-108.

Dhandhukia et al., "Switchable elaslin-like polypeptides that respond to chemical inducers of dimerization.," Biomacromolecules, vol. 14, No. 4, Apr. 8, 2013, pp. 976-985.

Dreher et. al., "Temperature Triggered Self-Assembly of Polypeptides into Multivalent Spherical Micelles." J Am Chem Soc., vol. 130, No. 2, Jan. 16, 2008, pp. 687-694.

Fegan et al., "Chemically controlled protein assembly: techniques and applications.," Chem Rev., vol. 110, No. 6, 2010, pp. 3315-3336.

Floss, et al., "Elastin-Like Polypeptides Revolutionize Recombinant Protein Expression and their Biomedical Application.," Trends in Biotechnology, vol. 28, No. 1, 2009, pp. 37-45.

Floss, et al., "Influence of Elastin-Like Peptide Fusions on the Quantity and Quality of a Tobacco-Derived Human Immunodeficiency Virus-Neutralizing Antibody", Plant Biotechnology Journal, vol. 7, 2009, pp. 899-913.

Hamm-Alvarez, "Design and Cellular Internalization of Genetically Engineered Polypeptide Nanoparticles Displaying Adenovirus Knob Domain." Utah Drug Delivery Conference, 15th International Symposium on Recent Advances in Drug Delivery Systems "Drug Delivery: New Directions in a New Decade". Salt Lake City, Utah, Feb. 13-16, 2011, 26 pages.

Hassouneh et al., "Fusions of Elastin-Like Polypeptides to Pharmaceutical Proteins", Methods of Enzymology, vol. 502, 2012, pp. 215-237.

Holliger et al., "Engineered antibody fragments and the rise of single domains", Nature Biotechnology, vol. 23, No. 9, 2005, pp. 1126-1136.

Hsueh et al., "Development of Novel Peptide Nanoparticles Targeted to Coxsackievirus-Adenovirus Receptor Expressing Cells." AAPS 2011, Washington, DC, Oct. 23-27, 2011, 1 page.

Macewan et al., "Elastin-like polypeptides: biomedical applications of tunable biopolymers.," PeptideScience, vol. 94, No. 1, 2010, pp. 60-77.

Mackay et al., "Genetically Engineered Polypeptide Nanoparticles." ACS Western Regional Meeting 2011, Pasadena, CA, Nov. 11, 2011, 31 pages.

Mackay et al., "Ocular Drug Delivery Using a Thermo-responsive Lacritin Fusion Protein," Abstract of presentation at ARVO 2012, Fort Lauderdale, FL (May 4-6, 2012), 2 pages.

Mackay, "Protein polymers—a platform for biopharmaceutical delivery and self-assembly." Keck Seminar, posted online Jun. 27, 2011, 53 pages.

Mcdaniel et al., "Drug delivery to solid tumors by elastin-like polypeptides.," Adv Drug Deliv Rev., vol. 62, No. 15, Dec. 30, 2010, pp. 1456-1467.

Mcdaniel et al., "Recursive Directional Ligation by Plasmid Reconstruction Allows Rapid and Seamless Cloning of Oligomeric Genes.," Biomacromolecules, vol. 11, No. 4, Apr. 12, 2010, pp. 944-952.

Meyer et al., "Purification of recombinant proteins by fusion with thermally-responsive polypeptides.," Nature Biotechnology, vol. 17, No. 11, Nov. 1999, pp. 1112-1115.

Non-Final Office Action on U.S. Appl. No. 16/038,051 dated Dec. 31, 2019, 22 pages.

Putnam et al., "Primary structure of a human IgA1 immunoglobulin. IV. Streptococcal IgA1 protease, digestion, Fab and Fc fragments, and the complete amino acid sequence of the alpha 1 heavy chain." J. Biol. Chem., vol. 254, No. 8, Apr. 25, 1979, pp. 2865-2874.

Scheller et al., "Forcing Single-Chain Variable Fragment Production in Tobacco Seeds by Fusion to Elastin-like Polypeptides", Plant Biotech. Journ., vol. 4, 2006, pp. 243-249.

Scheller, et al., "Purification of Spider Silk-Elastin from Transgenic Plants and Application for Human Chondrocyte Proliferation.," Transgenic Research, vol. 13, 2004, pp. 51-57.

Shah et al., "Biodegradation of elastin-like polypeptide nanoparticles.," Protein Sci., vol. 21, No. 6, Mar. 20, 2012, pp. 743-750.

Sun et al., "Design and cellular internalization of genetically engineered polypeptide nanoparticles displaying adenovirus knob domain" J Control Release., vol. 155, No. 2, Oct. 30, 2011, pp. 218-226.

Sun et al., "Genetically engineered polypeptide nanoparticles targeted to lacrimal gland acinar cells." Presented at ARVO 2011, Fort Lauderdale, FL, May 1-5, 2011, 1 page.

Supplement for Sun et al. "Design and cellular internalization of genetically engineered polypeptide nanoparticles displaying adenovirus knob domain" J Control Release., vol. 155, No. 2, Oct. 30, 2011, pp. 218-226.

Trabbic-Carlson et al., "Expression and purification of recombinant proteins from *Escherichia coli*: Comparison of an elastin-like polypeptide fusion with an oligohistidine fusion.," Protein Science, vol. 13, No. 12, 2004, pp. 3274-3284.

Welply et al., "A peptide isolated by phage display binds to ICAM-1 and inhibits binding to LFA-1", Proteins: Structure, Function and Genetics, vol. 26, 1996, pp. 262-270.

Wu et al., "Fabrication of elastin-like polypeptide nanoparticles for drug delivery by electrospraying," Biomacromolecules, vol. 10, No. 1, Jan. 12, 2009, pp. 19-24.

Yampolsky et al., "The Exchangeability of Amino Acids in Proteins," Genetics, vol. 170, Aug. 2005, pp. 1459-1472.

(56) References Cited

OTHER PUBLICATIONS

Chen et al., "Enhancement and destruction of antibody function by somatic mutation: unequal occurrence is controlled by V gene combinational associations", The EMBO Journal, vol. 14, No. 12, Mar. 12, 1995, pp. 2784-2794.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, vol. 169, 2002, pp. 3076-3084.

Dreher et al. Temperature triggered self-assembly of polypeptides into multivalent spherical micelles. J Am Chem Soc. Jan. 16, 2008;130(2):687-94. doi: 10.1021/ja0764862. Epub Dec. 18, 2007.

Dufner et al., "Harnessing phage and ribosome display for antibody optimization", Trends Biotechnol., vol. 24, No. 11, Sep. 26, 2006, pp. 523-529.

Hamm-Alvarez, "Design and Cellular Internalization of Genetically Engineered Polypeptide Nanoparticles Displaying Adenovirus Knob Domain." presented in Utah on Feb. 14, 2011, 34 pages.

Joensuu et al., "Expression and purification of an anti-Foot-and-mouth disease virus single-chain variable antibody fragment in tobacco plants", Transgenic Res., vol. 18, Apr. 3, 2009, pp. 685-696.

Jubala et al., "CD20 Expression in Normal Canine B Cells and in Canine non-Hodgkin Lymphoma", Vet Pathol., vol. 42, 2005, pp. 468-476.

Kussie et al., "A Single Engineered Amino Acid Substitution Changes Antibody Fine Specificity", J. Immunol., vol. 152, 1994, pp. 146-152.

Maccallum et al., "Antibody-antigen Interactions: Contact Analysis and Binding Site Topography", J. Mol. Biol., vol. 262, Jul. 30, 1996, pp. 732-745.

Rudikoff et al., "Single amino acid substitution altering antigen-binding specificity", Proc. Natl. Acad. Sci. USA, vol. 79, Mar. 1982, pp. 1979-1983.

Sheth et al., "Purification of monoclonal antibodies by affinity precipitation using thermally responsive elastin-like polypeptides(ELPs) fused to IgG binding domains: High-throughput analysis and scale up considerations.," Mar. 27, 2012, 1 page.

Urry. Physical Chemistry of Biological Free Energy Transduction as Demonstrated by Elastic Protein-Based Polymers. J. Phys. Chem. B 1997, 101, 51, 11007-11028. Publication Date:Dec. 18, 1997.

Vajdos et al., "Comprehensive Functional Maps of the Antigen-binding Site of an Anti-ErB2 Antibody Obtained with Shotgun Scanning Mutagenesis", J. Mol. Biol., vol. 320, Mar. 22, 2002, pp. 415-428.

Wang et al., "Control of Ocular Drug Bioavailability Using Thermal-Responsive Polypeptides." Controlled Release Meeting, Aug. 3, 2011, 1 page.

Wu et al., "Humanization of a Murine Monoclonal Antibody by Simultaneous Optimization of Framework and CDR Residues", J. Mol. Biol., vol. 294, Aug. 26, 1999, pp. 151-162.

Dhandhukia, et al., "Berunda Polypeptides: Multi-Headed Fusion Proteins Promote Subcutaneous Administration of Rapamycin to Breast Cancer In Vivo", Theranostics, 2017, vol. 7, Issue 16, pp. 3856-3872.

SEQUENCE LISTING

<160> NUMBER OF SEQ ID NOS: 25

<210> SEQ ID NO 1
<211> LENGTH: 576
<212> TYPE: DNA
<213> ORGANISM: Homo Sapiens

<400> SEQUENCE: 1

```
actcttctgg tccccacaga ctcagagaga acccaccatg gtgctgtctc ctgccgacaa      60
gaccaacgtc aaggccgcct ggggtaaggt cggcgcgcac gctggcgagt atggtgcgga     120
ggccctggag aggatgttcc tgtccttccc caccaccaag acctacttcc cgcacttcga     180
cctgagccac ggctctgccc aggttaaggg ccacggcaag aaggtggccg acgcgctgac     240
caacgccgtg gcgcacgtgg acgacatgcc caacgcgctg tccgccctga gcgacctgca     300
cgcgcacaag cttcgggtgg acccggtcaa cttcaagctc ctaagccact gcctgctggt     360
gaccctggcc gcccacctcc ccgccgagtt caccccctgcg gtgcacgcct ccctggacaa     420
gttcctggct tctgtgagca ccgtgctgac ctccaaatac cgttaagctg gagcctcggt     480
ggccatgctt cttgcccctt gggcctcccc ccagcccctc ctcccttcc tgcacccgta      540 cccccgtggt ctttgaataa agtctgagtg ggcggc                                576
```

<210> SEQ ID NO 2

<211> LENGTH: 622
<212> TYPE: DNA
<213> ORGANISM: Homo Sapiens

<400> SEQUENCE: 2

```
cataaaccct ggcgcgctcg cgggccggca ctcttctggt ccccacagac tcagagagaa      60
cccaccatgg tgctgtctcc tgccgacaag accaacgtca aggccgcctg ggtaaggtc      120
ggcgcgcacg ctggcgagta tggtgcgagg ccctggaga ggatgttcct gtccttcccc      180
accaccaaga cctacttccc gcacttcgac ctgagccacg gctctgccca ggttaagggc      240
cacggcaaga aggtggccga cgcgctgacc aacgccgtgg cgcacgtgga cgacatgccc      300
aacgcgctgt ccgccctgag cgacctgcac gcgcacaagc ttcgggtgga cccggtcaac      360
ttcaagctcc taagccactg cctgctggtg accctggccg cccacctccc cgccgagttc      420
accccctgcgg tgcacgcctc cctggacaag ttcctggctt ctgtgagcac cgtgctgacc      480
tccaaatacc gttaagctgg agcctcggta gccgttcctc ctgcccgctg ggcctcccaa      540
cgggccctcc tccctccttt gcaccggccc ttcctggtct ttgaataaag tctgagtggg      600
cagcaaaaaa aaaaaaaaaa aa                                              622
```

<210> SEQ ID NO 3
<211> LENGTH: 626
<212> TYPE: DNA
<213> ORGANISM: Homo Sapiens

<400> SEQUENCE: 3

```
acatttgctt ctgacacaac tgtgttcact agcaacctca aacagacacc atggtgcatc      60
tgactcctga ggagaagtct gccgttactg ccctgtgggg caaggtgaac gtggatgaag      120
ttggtggtga ggccctgggc aggctgctgg tggtctaccc ttggacccag aggttctttg      180
agtcctttgg ggatctgtcc actcctgatg ctgttatggg caaccctaag gtgaaggctc      240
atggcaagaa agtgctcggt gcctttagtg atggcctggc tcacctggac aacctcaagg      300
gcacctttgc cacactgagt gagctgcact gtgacaagct gcacgtggat cctgagaact      360
tcaggctcct gggcaacgtg ctggtctgtg tgctggccca tcactttggc aaagaattca      420
ccccaccagt gcaggctgcc tatcagaaag tggtggctgg tgtggctaat gccctggccc      480
acaagtatca ctaagctcgc tttcttgctg tccaatttct attaaaggtt cctttgttcc      540
ctaagtccaa ctactaaact gggggatatt atgaagggcc ttgagcatct ggattctgcc      600
taataaaaaa catttatttt cattgc                                          626
```

<210> SEQ ID NO 4
<211> LENGTH: 142
<212> TYPE: PRT
<213> ORGANISM: Homo Sapiens

<400> SEQUENCE: 4

```
Met Val Leu Ser Pro Ala Asp Lys Thr Asn Val Lys Ala Ala Trp Gly
  1               5                  10                  15

Lys Val Gly Ala His Ala Gly Glu Tyr Gly Ala Glu Ala Leu Glu Arg
             20                  25                  30

Met Phe Leu Ser Phe Pro Thr Thr Lys Thr Tyr Phe Pro His Phe Asp
         35                  40                  45

Leu Ser His Gly Ser Ala Gln Val Lys Gly His Gly Lys Lys Val Ala
     50                  55                  60

Asp Ala Leu Thr Asn Ala Val Ala His Val Asp Asp Met Pro Asn Ala
```

65                  70                  75                  80
Leu Ser Ala Leu Ser Asp Leu His Ala His Lys Leu Arg Val Asp Pro
                    85                  90                  95

Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140

<210> SEQ ID NO 5
<211> LENGTH: 147
<212> TYPE: PRT
<213> ORGANISM: Homo Sapiens

<400> SEQUENCE: 5

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 6
<211> LENGTH: 147
<212> TYPE: PRT
<213> ORGANISM: Homo sapiens

<400> SEQUENCE: 6

Met Gly His Phe Thr Glu Glu Asp Lys Ala Thr Ile Thr Ser Leu Trp
1               5                   10                  15

Gly Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60

Gly Lys Lys Val Leu Thr Ser Leu Gly Asp Ala Ile Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val

```
                100             105             110
Thr Val Leu Ala Ile His Phe Gly Lys Glu Phe Thr Pro Glu Val Gln
            115                 120                 125
Ala Ser Trp Gln Lys Met Val Thr Ala Val Ala Ser Ala Leu Ser Ser
            130                 135                 140
Arg Tyr His
145

<210> SEQ ID NO 7
<211> LENGTH: 482
<212> TYPE: PRT
<213> ORGANISM: Homo sapiens

<400> SEQUENCE: 7

Gly Val Pro Gly Ser Gly Val Pro Gly Ser Gly Val Pro Gly Ser Gly
1               5                   10                  15
Val Pro Gly Ser Gly Val Pro Gly Ser Gly Val Pro Gly Ser Gly Val
            20                  25                  30
Pro Gly Ser Gly Val Pro Gly Ser Gly Val Pro Gly Ser Gly Val Pro
            35                  40                  45
Gly Ser Gly Val Pro Gly Ser Gly Val Pro Gly Ser Gly Val Pro Gly
        50                  55                  60
Ser Gly Val Pro Gly Ser Gly Val Pro Gly Ser Gly Val Pro Gly Ser
65                  70                  75                  80
Gly Val Pro Gly Ser Gly Val Pro Gly Ser Gly Val Pro Gly Ser Gly
                85                  90                  95
Val Pro Gly Ser Gly Val Pro Gly Ser Gly Val Pro Gly Ser Gly Val
            100                 105                 110
Pro Gly Ser Gly Val Pro Gly Ser Gly Val Pro Gly Ser Gly Val Pro
            115                 120                 125
Gly Ser Gly Val Pro Gly Ser Gly Val Pro Gly Ser Gly Val Pro Gly
        130                 135                 140
Ser Gly Val Pro Gly Ser Gly Val Pro Gly Ser Gly Val Pro Gly Ser
145                 150                 155                 160
Gly Val Pro Gly Ser Gly Val Pro Gly Ser Gly Val Pro Gly Ser Gly
                165                 170                 175
Val Pro Gly Ser Gly Val Pro Gly Ser Gly Val Pro Gly Ser Gly Val
            180                 185                 190
Pro Gly Ser Gly Val Pro Gly Ser Gly Val Pro Gly Ser Gly Val Pro
            195                 200                 205
Gly Ser Gly Val Pro Gly Ser Gly Val Pro Gly Ser Gly Val Pro Gly
        210                 215                 220
Ser Gly Val Pro Gly Ser Gly Val Pro Gly Ser Gly Val Pro Gly Ser
225                 230                 235                 240
Gly Val Pro Gly Ile Gly Val Pro Gly Ile Gly Val Pro Gly Ile Gly
                245                 250                 255
Val Pro Gly Ile Gly Val Pro Gly Ile Gly Val Pro Gly Ile Gly Val
            260                 265                 270
Pro Gly Ile Gly Val Pro Gly Ile Gly Val Pro Gly Ile Gly Val Pro
            275                 280                 285
Gly Ile Gly Val Pro Gly Ile Gly Val Pro Gly Ile Gly Val Pro Gly
        290                 295                 300
Ile Gly Val Pro Gly Ile Gly Val Pro Gly Ile Gly Val Pro Gly Ile
305                 310                 315                 320
```

-continued

```
Gly Val Pro Gly Ile Gly Val Pro Gly Ile Gly Val Pro Gly Ile Gly
                325                 330                 335
Val Pro Gly Ile Gly Val Pro Gly Ile Gly Val Pro Gly Ile Gly Val
            340                 345                 350
Pro Gly Ile Gly Val Pro Gly Ile Gly Val Pro Gly Ile Gly Val Pro
        355                 360                 365
Gly Ile Gly Val Pro Gly Ile Gly Val Pro Gly Ile Gly Val Pro Gly
    370                 375                 380
Ile Gly Val Pro Gly Ile Gly Val Pro Gly Ile Gly Val Pro Gly Ile
385                 390                 395                 400
Gly Val Pro Gly Ile Gly Val Pro Gly Ile Gly Val Pro Gly Ile Gly
                405                 410                 415
Val Pro Gly Ile Gly Val Pro Gly Ile Gly Val Pro Gly Ile Gly Val
            420                 425                 430
Pro Gly Ile Gly Val Pro Gly Ile Gly Val Pro Gly Ile Gly Val Pro
        435                 440                 445
Gly Ile Gly Val Pro Gly Ile Gly Val Pro Gly Ile Gly Val Pro Gly
    450                 455                 460
Ile Gly Val Pro Gly Ile Gly Val Pro Gly Ile Gly Val Pro Gly Ile
465                 470                 475                 480

Gly Tyr
```

<210> SEQ ID NO 8
<211> LENGTH: 624
<212> TYPE: PRT
<213> ORGANISM: Homo sapiens
<220> FEATURE:
<221> NAME/KEY: NON_CONS
<222> LOCATION: (481)..(482)
<223> OTHER INFORMATION: Residues at these positions are separated by a
      linking peptide which links ELP amino acid sequence to hemoglobin
      amino acid sequence

<400> SEQUENCE: 8

```
Gly Val Pro Gly Ser Gly Val Pro Gly Ser Gly Val Pro Gly Ser Gly
1               5                   10                  15
Val Pro Gly Ser Gly Val Pro Gly Ser Gly Val Pro Gly Ser Gly Val
            20                  25                  30
Pro Gly Ser Gly Val Pro Gly Ser Gly Val Pro Gly Ser Gly Val Pro
        35                  40                  45
Gly Ser Gly Val Pro Gly Ser Gly Val Pro Gly Ser Gly Val Pro Gly
    50                  55                  60
Ser Gly Val Pro Gly Ser Gly Val Pro Gly Ser Gly Val Pro Gly Ser
65                  70                  75                  80
Gly Val Pro Gly Ser Gly Val Pro Gly Ser Gly Val Pro Gly Ser Gly
                85                  90                  95
Val Pro Gly Ser Gly Val Pro Gly Ser Gly Val Pro Gly Ser Gly Val
            100                 105                 110
Pro Gly Ser Gly Val Pro Gly Ser Gly Val Pro Gly Ser Gly Val Pro
        115                 120                 125
Gly Ser Gly Val Pro Gly Ser Gly Val Pro Gly Ser Gly Val Pro Gly
    130                 135                 140
Ser Gly Val Pro Gly Ser Gly Val Pro Gly Ser Gly Val Pro Gly Ser
145                 150                 155                 160
Gly Val Pro Gly Ser Gly Val Pro Gly Ser Gly Val Pro Gly Ser Gly
                165                 170                 175
```

```
Val Pro Gly Ser Gly Val Pro Gly Ser Gly Val Pro Gly Ser Gly Val
            180                 185                 190

Pro Gly Ser Gly Val Pro Gly Ser Gly Val Pro Gly Ser Gly Val Pro
        195                 200                 205

Gly Ser Gly Val Pro Gly Ser Gly Val Pro Gly Ser Gly Val Pro Gly
    210                 215                 220

Ser Gly Val Pro Gly Ser Gly Val Pro Gly Ser Gly Val Pro Gly Ser
225                 230                 235                 240

Gly Val Pro Gly Ile Gly Val Pro Gly Ile Gly Val Pro Gly Ile Gly
                245                 250                 255

Val Pro Gly Ile Gly Val Pro Gly Ile Gly Val Pro Gly Ile Gly Val
            260                 265                 270

Pro Gly Ile Gly Val Pro Gly Ile Gly Val Pro Gly Ile Gly Val Pro
        275                 280                 285

Gly Ile Gly Val Pro Gly Ile Gly Val Pro Gly Ile Gly Val Pro Gly
    290                 295                 300

Ile Gly Val Pro Gly Ile Gly Val Pro Gly Ile Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Ile Gly Val Pro Gly Ile Gly Val
            340                 345                 350

Pro Gly Ile Gly Val Pro Gly Ile Gly Val Pro Gly Ile Gly Val Pro
        355                 360                 365

Gly Ile Gly Val Pro Gly Ile Gly Val Pro Gly Ile Gly Val Pro Gly
    370                 375                 380

Ile Gly Val Pro Gly Ile Gly Val Pro Gly Ile Gly Val Pro Gly Ile
385                 390                 395                 400

Gly Val Pro Gly Ile Gly Val Pro Gly Ile Gly Val Pro Gly Ile Gly
                405                 410                 415

Val Pro Gly Ile Gly Val Pro Gly Ile Gly Val Pro Gly Ile Gly Val
            420                 425                 430

Pro Gly Ile Gly Val Pro Gly Ile Gly Val Pro Gly Ile Gly Val Pro
        435                 440                 445

Gly Ile Gly Val Pro Gly Ile Gly Val Pro Gly Ile Gly Val Pro Gly
    450                 455                 460

Ile Gly Val Pro Gly Ile Gly Val Pro Gly Ile Gly Val Pro Gly Ile
465                 470                 475                 480

Gly Met Val Leu Ser Pro Ala Asp Lys Thr Asn Val Lys Ala Ala Trp
                485                 490                 495

Gly Lys Val Gly Ala His Ala Gly Glu Tyr Gly Ala Glu Ala Leu Glu
            500                 505                 510

Arg Met Phe Leu Ser Phe Pro Thr Thr Lys Thr Tyr Phe Pro His Phe
        515                 520                 525

Asp Leu Ser His Gly Ser Ala Gln Val Lys Gly His Gly Lys Lys Val
    530                 535                 540

Ala Asp Ala Leu Thr Asn Ala Val Ala His Val Asp Asp Met Pro Asn
545                 550                 555                 560

Ala Leu Ser Ala Leu Ser Asp Leu His Ala His Lys Leu Arg Val Asp
                565                 570                 575

Pro Val Asn Phe Lys Leu Leu Ser His Cys Leu Leu Val Thr Leu Ala
            580                 585                 590

Ala His Leu Pro Ala Glu Phe Thr Pro Ala Val His Ala Ser Leu Asp
```

```
                    595                 600                 605

Lys Phe Leu Ala Ser Val Ser Thr Val Leu Thr Ser Lys Tyr Arg Tyr
    610                 615                 620

<210> SEQ ID NO 9
<211> LENGTH: 629
<212> TYPE: PRT
<213> ORGANISM: Homo sapiens
<220> FEATURE:
<221> NAME/KEY: NON_CONS
<222> LOCATION: (481)..(482)
<223> OTHER INFORMATION: Residues at these positions are separated by a
      linking peptide which links ELP amino acid sequence to hemoglobin
      amino acid sequence

<400> SEQUENCE: 9

Gly Val Pro Gly Ser Gly Val Pro Gly Ser Gly Val Pro Gly Ser Gly
1               5                   10                  15

Val Pro Gly Ser Gly Val Pro Gly Ser Gly Val Pro Gly Ser Gly Val
                20                  25                  30

Pro Gly Ser Gly Val Pro Gly Ser Gly Val Pro Gly Ser Gly Val Pro
            35                  40                  45

Gly Ser Gly Val Pro Gly Ser Gly Val Pro Gly Ser Gly Val Pro Gly
    50                  55                  60

Ser Gly Val Pro Gly Ser Gly Val Pro Gly Ser Gly Val Pro Gly Ser
65                  70                  75                  80

Gly Val Pro Gly Ser Gly Val Pro Gly Ser Gly Val Pro Gly Ser Gly
                85                  90                  95

Val Pro Gly Ser Gly Val Pro Gly Ser Gly Val Pro Gly Ser Gly Val
            100                 105                 110

Pro Gly Ser Gly Val Pro Gly Ser Gly Val Pro Gly Ser Gly Val Pro
        115                 120                 125

Gly Ser Gly Val Pro Gly Ser Gly Val Pro Gly Ser Gly Val Pro Gly
    130                 135                 140

Ser Gly Val Pro Gly Ser Gly Val Pro Gly Ser Gly Val Pro Gly Ser
145                 150                 155                 160

Gly Val Pro Gly Ser Gly Val Pro Gly Ser Gly Val Pro Gly Ser Gly
                165                 170                 175

Val Pro Gly Ser Gly Val Pro Gly Ser Gly Val Pro Gly Ser Gly Val
            180                 185                 190

Pro Gly Ser Gly Val Pro Gly Ser Gly Val Pro Gly Ser Gly Val Pro
        195                 200                 205

Gly Ser Gly Val Pro Gly Ser Gly Val Pro Gly Ser Gly Val Pro Gly
    210                 215                 220

Ser Gly Val Pro Gly Ser Gly Val Pro Gly Ser Gly Val Pro Gly Ser
225                 230                 235                 240

Gly Val Pro Gly Ile Gly Val Pro Gly Ile Gly Val Pro Gly Ile Gly
                245                 250                 255

Val Pro Gly Ile Gly Val Pro Gly Ile Gly Val Pro Gly Ile Gly Val
            260                 265                 270

Pro Gly Ile Gly Val Pro Gly Ile Gly Val Pro Gly Ile Gly Val Pro
        275                 280                 285

Gly Ile Gly Val Pro Gly Ile Gly Val Pro Gly Ile Gly Val Pro Gly
    290                 295                 300

Ile Gly Val Pro Gly Ile Gly Val Pro Gly Ile Gly Val Pro Gly Ile
305                 310                 315                 320
```

Gly Val Pro Gly Ile Gly Val Pro Gly Ile Gly Val Pro Gly Ile Gly
                325                 330                 335

Val Pro Gly Ile Gly Val Pro Gly Ile Gly Val Pro Gly Ile Gly Val
            340                 345                 350

Pro Gly Ile Gly Val Pro Gly Ile Gly Val Pro Gly Ile Gly Val Pro
        355                 360                 365

Gly Ile Gly Val Pro Gly Ile Gly Val Pro Gly Ile Gly Val Pro Gly
    370                 375                 380

Ile Gly Val Pro Gly Ile Gly Val Pro Gly Ile Gly Val Pro Gly Ile
385                 390                 395                 400

Gly Val Pro Gly Ile Gly Val Pro Gly Ile Gly Val Pro Gly Ile Gly
                405                 410                 415

Val Pro Gly Ile Gly Val Pro Gly Ile Gly Val Pro Gly Ile Gly Val
            420                 425                 430

Pro Gly Ile Gly Val Pro Gly Ile Gly Val Pro Gly Ile Gly Val Pro
        435                 440                 445

Gly Ile Gly Val Pro Gly Ile Gly Val Pro Gly Ile Gly Val Pro Gly
    450                 455                 460

Ile Gly Val Pro Gly Ile Gly Val Pro Gly Ile Gly Val Pro Gly Ile
465                 470                 475                 480

Gly Met Val His Leu Thr Pro Glu Glu Lys Ser Ala Val Thr Ala Leu
                485                 490                 495

Trp Gly Lys Val Asn Val Asp Glu Val Gly Gly Glu Ala Leu Gly Arg
            500                 505                 510

Leu Leu Val Val Tyr Pro Trp Thr Gln Arg Phe Phe Glu Ser Phe Gly
        515                 520                 525

Asp Leu Ser Thr Pro Asp Ala Val Met Gly Asn Pro Lys Val Lys Ala
    530                 535                 540

His Gly Lys Lys Val Leu Gly Ala Phe Ser Asp Gly Leu Ala His Leu
545                 550                 555                 560

Asp Asn Leu Lys Gly Thr Phe Ala Thr Leu Ser Glu Leu His Cys Asp
                565                 570                 575

Lys Leu His Val Asp Pro Glu Asn Phe Arg Leu Leu Gly Asn Val Leu
            580                 585                 590

Val Cys Val Leu Ala His His Phe Gly Lys Glu Phe Thr Pro Pro Val
        595                 600                 605

Gln Ala Ala Tyr Gln Lys Val Val Ala Gly Val Ala Asn Ala Leu Ala
    610                 615                 620

His Lys Tyr His Tyr
625

<210> SEQ ID NO 10
<211> LENGTH: 629
<212> TYPE: PRT
<213> ORGANISM: Homo sapiens
<220> FEATURE:
<221> NAME/KEY: NON_CONS
<222> LOCATION: (481)..(482)
<223> OTHER INFORMATION: Residues at these positions are separated by a
      linking peptide which links ELP amino acid sequence to hemoglobin
      amino acid sequence

<400> SEQUENCE: 10

Gly Val Pro Gly Ser Gly Val Pro Gly Ser Gly Val Pro Gly Ser Gly
1               5                   10                  15

Val Pro Gly Ser Gly Val Pro Gly Ser Gly Val Pro Gly Ser Gly Val
            20                  25                  30

-continued

Pro Gly Ser Gly Val Pro Gly Ser Gly Val Pro Gly Ser Gly Val Pro
         35                  40                  45

Gly Ser Gly Val Pro Gly Ser Gly Val Pro Gly Ser Gly Val Pro Gly
     50                  55                  60

Ser Gly Val Pro Gly Ser Gly Val Pro Gly Ser Gly Val Pro Gly Ser
 65                  70                  75                  80

Gly Val Pro Gly Ser Gly Val Pro Gly Ser Gly Val Pro Gly Ser Gly
                 85                  90                  95

Val Pro Gly Ser Gly Val Pro Gly Ser Gly Val Pro Gly Ser Gly Val
             100                 105                 110

Pro Gly Ser Gly Val Pro Gly Ser Gly Val Pro Gly Ser Gly Val Pro
         115                 120                 125

Gly Ser Gly Val Pro Gly Ser Gly Val Pro Gly Ser Gly Val Pro Gly
     130                 135                 140

Ser Gly Val Pro Gly Ser Gly Val Pro Gly Ser Gly Val Pro Gly Ser
145                 150                 155                 160

Gly Val Pro Gly Ser Gly Val Pro Gly Ser Gly Val Pro Gly Ser Gly
                165                 170                 175

Val Pro Gly Ser Gly Val Pro Gly Ser Gly Val Pro Gly Ser Gly Val
            180                 185                 190

Pro Gly Ser Gly Val Pro Gly Ser Gly Val Pro Gly Ser Gly Val Pro
        195                 200                 205

Gly Ser Gly Val Pro Gly Ser Gly Val Pro Gly Ser Gly Val Pro Gly
    210                 215                 220

Ser Gly Val Pro Gly Ser Gly Val Pro Gly Ser Gly Val Pro Gly Ser
225                 230                 235                 240

Gly Val Pro Gly Ile Gly Val Pro Gly Ile Gly Val Pro Gly Ile Gly
                245                 250                 255

Val Pro Gly Ile Gly Val Pro Gly Ile Gly Val Pro Gly Ile Gly Val
            260                 265                 270

Pro Gly Ile Gly Val Pro Gly Ile Gly Val Pro Gly Ile Gly Val Pro
        275                 280                 285

Gly Ile Gly Val Pro Gly Ile Gly Val Pro Gly Ile Gly Val Pro Gly
    290                 295                 300

Ile Gly Val Pro Gly Ile Gly Val Pro Gly Ile Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Ile Gly Val Pro Gly Ile Gly Val
            340                 345                 350

Pro Gly Ile Gly Val Pro Gly Ile Gly Val Pro Gly Ile Gly Val Pro
        355                 360                 365

Gly Ile Gly Val Pro Gly Ile Gly Val Pro Gly Ile Gly Val Pro Gly
    370                 375                 380

Ile Gly Val Pro Gly Ile Gly Val Pro Gly Ile Gly Val Pro Gly Ile
385                 390                 395                 400

Gly Val Pro Gly Ile Gly Val Pro Gly Ile Gly Val Pro Gly Ile Gly
                405                 410                 415

Val Pro Gly Ile Gly Val Pro Gly Ile Gly Val Pro Gly Ile Gly Val
            420                 425                 430

Pro Gly Ile Gly Val Pro Gly Ile Gly Val Pro Gly Ile Gly Val Pro
        435                 440                 445

Gly Ile Gly Val Pro Gly Ile Gly Val Pro Gly Ile Gly Val Pro Gly
            450                 455                 460

Ile Gly Val Pro Gly Ile Gly Val Pro Gly Ile Gly Val Pro Gly Ile
465                 470                 475                 480

Gly Met Gly His Phe Thr Glu Glu Asp Lys Ala Thr Ile Thr Ser Leu
                485                 490                 495

Trp Gly Lys Val Asn Val Glu Asp Ala Gly Gly Glu Thr Leu Gly Arg
            500                 505                 510

Leu Leu Val Val Tyr Pro Trp Thr Gln Arg Phe Phe Asp Ser Phe Gly
        515                 520                 525

Asn Leu Ser Ser Ala Ser Ala Ile Met Gly Asn Pro Lys Val Lys Ala
530                 535                 540

His Gly Lys Lys Val Leu Thr Ser Leu Gly Asp Ala Ile Lys His Leu
545                 550                 555                 560

Asp Asp Leu Lys Gly Thr Phe Ala Gln Leu Ser Glu Leu His Cys Asp
                565                 570                 575

Lys Leu His Val Asp Pro Glu Asn Phe Lys Leu Leu Gly Asn Val Leu
            580                 585                 590

Val Thr Val Leu Ala Ile His Phe Gly Lys Glu Phe Thr Pro Glu Val
        595                 600                 605

Gln Ala Ser Trp Gln Lys Met Val Thr Ala Val Ala Ser Ala Leu Ser
    610                 615                 620

Ser Arg Tyr His Tyr
625

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 11

Val Pro Gly Xaa Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Gly Ala Gly Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

-continued

```
Val Pro Gly Val Gly
1               5

<210> SEQ ID NO 14
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any hydrophilic amino acid
<220> FEATURE:
<221> NAME/KEY: MOD_RES
<222> LOCATION: (9)..(9)
<223> OTHER INFORMATION: Any hydrophilic amino acid
<220> FEATURE:
<221> NAME/KEY: MOD_RES
<222> LOCATION: (14)..(14)
<223> OTHER INFORMATION: Any hydrophilic amino acid
<220> FEATURE:
<221> NAME/KEY: MOD_RES
<222> LOCATION: (19)..(19)
<223> OTHER INFORMATION: Any hydrophilic amino acid
<220> FEATURE:
<221> NAME/KEY: MOD_RES
<222> LOCATION: (24)..(24)
<223> OTHER INFORMATION: Any hydrophilic amino acid
<220> FEATURE:
<221> NAME/KEY: MOD_RES
<222> LOCATION: (29)..(29)
<223> OTHER INFORMATION: Any hydrophilic amino acid
<220> FEATURE:
<221> NAME/KEY: MOD_RES
<222> LOCATION: (34)..(34)
<223> OTHER INFORMATION: Any hydrophilic amino acid
<220> FEATURE:
<221> NAME/KEY: MOD_RES
<222> LOCATION: (39)..(39)
<223> OTHER INFORMATION: Any hydrophilic amino acid
<220> FEATURE:
<221> NAME/KEY: MOD_RES
<222> LOCATION: (44)..(44)
<223> OTHER INFORMATION: Any hydrophilic amino acid
<220> FEATURE:
<221> NAME/KEY: MOD_RES
<222> LOCATION: (49)..(49)
<223> OTHER INFORMATION: Any hydrophilic amino acid
<220> FEATURE:
<221> NAME/KEY: MOD_RES
<222> LOCATION: (54)..(54)
<223> OTHER INFORMATION: Any hydrophilic amino acid
<220> FEATURE:
<221> NAME/KEY: MOD_RES
<222> LOCATION: (59)..(59)
<223> OTHER INFORMATION: Any hydrophilic amino acid
<220> FEATURE:
<221> NAME/KEY: MOD_RES
<222> LOCATION: (64)..(64)
<223> OTHER INFORMATION: Any hydrophilic amino acid
<220> FEATURE:
<221> NAME/KEY: MOD_RES
<222> LOCATION: (69)..(69)
<223> OTHER INFORMATION: Any hydrophilic amino acid
<220> FEATURE:
<221> NAME/KEY: MOD_RES
<222> LOCATION: (74)..(74)
<223> OTHER INFORMATION: Any hydrophilic amino acid
<220> FEATURE:
<221> NAME/KEY: MOD_RES
<222> LOCATION: (79)..(79)
<223> OTHER INFORMATION: Any hydrophilic amino acid
<220> FEATURE:
<221> NAME/KEY: MOD_RES
<222> LOCATION: (84)..(84)
<223> OTHER INFORMATION: Any hydrophilic amino acid
```

```
<220> FEATURE:
<221> NAME/KEY: MOD_RES
<222> LOCATION: (89)..(89)
<223> OTHER INFORMATION: Any hydrophilic amino acid
<220> FEATURE:
<221> NAME/KEY: MOD_RES
<222> LOCATION: (94)..(94)
<223> OTHER INFORMATION: Any hydrophilic amino acid
<220> FEATURE:
<221> NAME/KEY: MOD_RES
<222> LOCATION: (99)..(99)
<223> OTHER INFORMATION: Any hydrophilic amino acid
<220> FEATURE:
<221> NAME/KEY: MOD_RES
<222> LOCATION: (104)..(104)
<223> OTHER INFORMATION: Any hydrophilic amino acid
<220> FEATURE:
<221> NAME/KEY: MOD_RES
<222> LOCATION: (109)..(109)
<223> OTHER INFORMATION: Any hydrophilic amino acid
<220> FEATURE:
<221> NAME/KEY: MOD_RES
<222> LOCATION: (114)..(114)
<223> OTHER INFORMATION: Any hydrophilic amino acid
<220> FEATURE:
<221> NAME/KEY: MOD_RES
<222> LOCATION: (119)..(119)
<223> OTHER INFORMATION: Any hydrophilic amino acid
<220> FEATURE:
<221> NAME/KEY: MOD_RES
<222> LOCATION: (124)..(124)
<223> OTHER INFORMATION: Any hydrophilic amino acid
<220> FEATURE:
<221> NAME/KEY: MOD_RES
<222> LOCATION: (129)..(129)
<223> OTHER INFORMATION: Any hydrophilic amino acid
<220> FEATURE:
<221> NAME/KEY: MOD_RES
<222> LOCATION: (134)..(134)
<223> OTHER INFORMATION: Any hydrophilic amino acid
<220> FEATURE:
<221> NAME/KEY: MOD_RES
<222> LOCATION: (139)..(139)
<223> OTHER INFORMATION: Any hydrophilic amino acid
<220> FEATURE:
<221> NAME/KEY: MOD_RES
<222> LOCATION: (144)..(144)
<223> OTHER INFORMATION: Any hydrophilic amino acid
<220> FEATURE:
<221> NAME/KEY: MOD_RES
<222> LOCATION: (149)..(149)
<223> OTHER INFORMATION: Any hydrophilic amino acid
<220> FEATURE:
<221> NAME/KEY: MOD_RES
<222> LOCATION: (154)..(154)
<223> OTHER INFORMATION: Any hydrophilic amino acid
<220> FEATURE:
<221> NAME/KEY: MOD_RES
<222> LOCATION: (159)..(159)
<223> OTHER INFORMATION: Any hydrophilic amino acid
<220> FEATURE:
<221> NAME/KEY: MOD_RES
<222> LOCATION: (164)..(164)
<223> OTHER INFORMATION: Any hydrophilic amino acid
<220> FEATURE:
<221> NAME/KEY: MOD_RES
<222> LOCATION: (169)..(169)
<223> OTHER INFORMATION: Any hydrophilic amino acid
<220> FEATURE:
<221> NAME/KEY: MOD_RES
<222> LOCATION: (174)..(174)
<223> OTHER INFORMATION: Any hydrophilic amino acid
<220> FEATURE:
<221> NAME/KEY: MOD_RES
<222> LOCATION: (179)..(179)
<223> OTHER INFORMATION: Any hydrophilic amino acid
<220> FEATURE:
<221> NAME/KEY: MOD_RES
<222> LOCATION: (184)..(184)
```

```
<223> OTHER INFORMATION: Any hydrophilic amino acid
<220> FEATURE:
<221> NAME/KEY: MOD_RES
<222> LOCATION: (189)..(189)
<223> OTHER INFORMATION: Any hydrophilic amino acid
<220> FEATURE:
<221> NAME/KEY: MOD_RES
<222> LOCATION: (194)..(194)
<223> OTHER INFORMATION: Any hydrophilic amino acid
<220> FEATURE:
<221> NAME/KEY: MOD_RES
<222> LOCATION: (199)..(199)
<223> OTHER INFORMATION: Any hydrophilic amino acid
<220> FEATURE:
<221> NAME/KEY: MOD_RES
<222> LOCATION: (204)..(204)
<223> OTHER INFORMATION: Any hydrophilic amino acid
<220> FEATURE:
<221> NAME/KEY: MOD_RES
<222> LOCATION: (209)..(209)
<223> OTHER INFORMATION: Any hydrophilic amino acid
<220> FEATURE:
<221> NAME/KEY: MOD_RES
<222> LOCATION: (214)..(214)
<223> OTHER INFORMATION: Any hydrophilic amino acid
<220> FEATURE:
<221> NAME/KEY: MOD_RES
<222> LOCATION: (219)..(219)
<223> OTHER INFORMATION: Any hydrophilic amino acid
<220> FEATURE:
<221> NAME/KEY: MOD_RES
<222> LOCATION: (224)..(224)
<223> OTHER INFORMATION: Any hydrophilic amino acid
<220> FEATURE:
<221> NAME/KEY: MOD_RES
<222> LOCATION: (229)..(229)
<223> OTHER INFORMATION: Any hydrophilic amino acid
<220> FEATURE:
<221> NAME/KEY: MOD_RES
<222> LOCATION: (234)..(234)
<223> OTHER INFORMATION: Any hydrophilic amino acid
<220> FEATURE:
<221> NAME/KEY: MOD_RES
<222> LOCATION: (239)..(239)
<223> OTHER INFORMATION: Any hydrophilic amino acid
<220> FEATURE:
<221> NAME/KEY: MOD_RES
<222> LOCATION: (244)..(244)
<223> OTHER INFORMATION: Any hydrophilic amino acid
<220> FEATURE:
<221> NAME/KEY: MOD_RES
<222> LOCATION: (249)..(249)
<223> OTHER INFORMATION: Any hydrophilic amino acid
<220> FEATURE:
<221> NAME/KEY: MOD_RES
<222> LOCATION: (254)..(254)
<223> OTHER INFORMATION: Any hydrophilic amino acid
<220> FEATURE:
<221> NAME/KEY: MOD_RES
<222> LOCATION: (259)..(259)
<223> OTHER INFORMATION: Any hydrophilic amino acid
<220> FEATURE:
<221> NAME/KEY: MOD_RES
<222> LOCATION: (264)..(264)
<223> OTHER INFORMATION: Any hydrophilic amino acid
<220> FEATURE:
<221> NAME/KEY: MOD_RES
<222> LOCATION: (269)..(269)
<223> OTHER INFORMATION: Any hydrophilic amino acid
<220> FEATURE:
<221> NAME/KEY: MOD_RES
<222> LOCATION: (274)..(274)
<223> OTHER INFORMATION: Any hydrophilic amino acid
<220> FEATURE:
<221> NAME/KEY: MOD_RES
<222> LOCATION: (279)..(279)
<223> OTHER INFORMATION: Any hydrophilic amino acid
<220> FEATURE:
<221> NAME/KEY: MOD_RES
```

```
<222> LOCATION: (284)..(284)
<223> OTHER INFORMATION: Any hydrophilic amino acid
<220> FEATURE:
<221> NAME/KEY: MOD_RES
<222> LOCATION: (289)..(289)
<223> OTHER INFORMATION: Any hydrophilic amino acid
<220> FEATURE:
<221> NAME/KEY: MOD_RES
<222> LOCATION: (294)..(294)
<223> OTHER INFORMATION: Any hydrophilic amino acid
<220> FEATURE:
<221> NAME/KEY: MOD_RES
<222> LOCATION: (299)..(299)
<223> OTHER INFORMATION: Any hydrophilic amino acid
<220> FEATURE:
<221> NAME/KEY: MOD_RES
<222> LOCATION: (304)..(304)
<223> OTHER INFORMATION: Any hydrophilic amino acid
<220> FEATURE:
<221> NAME/KEY: MOD_RES
<222> LOCATION: (309)..(309)
<223> OTHER INFORMATION: Any hydrophilic amino acid
<220> FEATURE:
<221> NAME/KEY: MOD_RES
<222> LOCATION: (314)..(314)
<223> OTHER INFORMATION: Any hydrophilic amino acid
<220> FEATURE:
<221> NAME/KEY: MOD_RES
<222> LOCATION: (319)..(319)
<223> OTHER INFORMATION: Any hydrophilic amino acid
<220> FEATURE:
<221> NAME/KEY: MOD_RES
<222> LOCATION: (324)..(324)
<223> OTHER INFORMATION: Any hydrophilic amino acid
<220> FEATURE:
<221> NAME/KEY: MOD_RES
<222> LOCATION: (329)..(329)
<223> OTHER INFORMATION: Any hydrophilic amino acid
<220> FEATURE:
<221> NAME/KEY: MOD_RES
<222> LOCATION: (334)..(334)
<223> OTHER INFORMATION: Any hydrophilic amino acid
<220> FEATURE:
<221> NAME/KEY: MOD_RES
<222> LOCATION: (339)..(339)
<223> OTHER INFORMATION: Any hydrophilic amino acid
<220> FEATURE:
<221> NAME/KEY: MOD_RES
<222> LOCATION: (344)..(344)
<223> OTHER INFORMATION: Any hydrophilic amino acid
<220> FEATURE:
<221> NAME/KEY: MOD_RES
<222> LOCATION: (349)..(349)
<223> OTHER INFORMATION: Any hydrophilic amino acid
<220> FEATURE:
<221> NAME/KEY: MOD_RES
<222> LOCATION: (354)..(354)
<223> OTHER INFORMATION: Any hydrophilic amino acid
<220> FEATURE:
<221> NAME/KEY: MOD_RES
<222> LOCATION: (359)..(359)
<223> OTHER INFORMATION: Any hydrophilic amino acid
<220> FEATURE:
<221> NAME/KEY: MOD_RES
<222> LOCATION: (364)..(364)
<223> OTHER INFORMATION: Any hydrophilic amino acid
<220> FEATURE:
<221> NAME/KEY: MOD_RES
<222> LOCATION: (369)..(369)
<223> OTHER INFORMATION: Any hydrophilic amino acid
<220> FEATURE:
<221> NAME/KEY: MOD_RES
<222> LOCATION: (374)..(374)
<223> OTHER INFORMATION: Any hydrophilic amino acid
<220> FEATURE:
<221> NAME/KEY: MOD_RES
<222> LOCATION: (379)..(379)
<223> OTHER INFORMATION: Any hydrophilic amino acid
<220> FEATURE:
```

<220> FEATURE:
<221> NAME/KEY: MOD_RES
<222> LOCATION: (384)..(384)
<223> OTHER INFORMATION: Any hydrophilic amino acid
<220> FEATURE:
<221> NAME/KEY: MOD_RES
<222> LOCATION: (389)..(389)
<223> OTHER INFORMATION: Any hydrophilic amino acid
<220> FEATURE:
<221> NAME/KEY: MOD_RES
<222> LOCATION: (394)..(394)
<223> OTHER INFORMATION: Any hydrophilic amino acid
<220> FEATURE:
<221> NAME/KEY: MOD_RES
<222> LOCATION: (399)..(399)
<223> OTHER INFORMATION: Any hydrophilic amino acid
<220> FEATURE:
<221> NAME/KEY: MOD_RES
<222> LOCATION: (404)..(404)
<223> OTHER INFORMATION: Any hydrophilic amino acid
<220> FEATURE:
<221> NAME/KEY: MOD_RES
<222> LOCATION: (409)..(409)
<223> OTHER INFORMATION: Any hydrophilic amino acid
<220> FEATURE:
<221> NAME/KEY: MOD_RES
<222> LOCATION: (414)..(414)
<223> OTHER INFORMATION: Any hydrophilic amino acid
<220> FEATURE:
<221> NAME/KEY: MOD_RES
<222> LOCATION: (419)..(419)
<223> OTHER INFORMATION: Any hydrophilic amino acid
<220> FEATURE:
<221> NAME/KEY: MOD_RES
<222> LOCATION: (424)..(424)
<223> OTHER INFORMATION: Any hydrophilic amino acid
<220> FEATURE:
<221> NAME/KEY: MOD_RES
<222> LOCATION: (429)..(429)
<223> OTHER INFORMATION: Any hydrophilic amino acid
<220> FEATURE:
<221> NAME/KEY: MOD_RES
<222> LOCATION: (434)..(434)
<223> OTHER INFORMATION: Any hydrophilic amino acid
<220> FEATURE:
<221> NAME/KEY: MOD_RES
<222> LOCATION: (439)..(439)
<223> OTHER INFORMATION: Any hydrophilic amino acid
<220> FEATURE:
<221> NAME/KEY: MOD_RES
<222> LOCATION: (444)..(444)
<223> OTHER INFORMATION: Any hydrophilic amino acid
<220> FEATURE:
<221> NAME/KEY: MOD_RES
<222> LOCATION: (449)..(449)
<223> OTHER INFORMATION: Any hydrophilic amino acid
<220> FEATURE:
<221> NAME/KEY: MISC_FEATURE
<222> LOCATION: (1)..(450)
<223> OTHER INFORMATION: This sequence may encompass 20-90 "Val-Pro-Gly-Xaa-Gly" repeating units

<400> SEQUENCE: 14

```
Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
```

85                  90                  95
Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
            165                 170                 175

Pro Gly Xaa Gly Val Pro Gly Xaa Gly Val Pro Gly Xaa Gly Val Pro
        180                 185                 190

Gly Xaa Gly Val Pro Gly Xaa Gly Val Pro Gly Xaa Gly Val Pro Gly
    195                 200                 205

Xaa Gly Val Pro Gly Xaa Gly Val Pro Gly Xaa Gly Val Pro Gly Xaa
210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
            245                 250                 255

Pro Gly Xaa Gly Val Pro Gly Xaa Gly Val Pro Gly Xaa Gly Val Pro
        260                 265                 270

Gly Xaa Gly Val Pro Gly Xaa Gly Val Pro Gly Xaa Gly Val Pro Gly
    275                 280                 285

Xaa Gly Val Pro Gly Xaa Gly Val Pro Gly Xaa Gly Val Pro Gly Xaa
290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
            325                 330                 335

Pro Gly Xaa Gly Val Pro Gly Xaa Gly Val Pro Gly Xaa Gly Val Pro
        340                 345                 350

Gly Xaa Gly Val Pro Gly Xaa Gly Val Pro Gly Xaa Gly Val Pro Gly
    355                 360                 365

Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
            405                 410                 415

Pro Gly Xaa Gly Val Pro Gly Xaa Gly Val Pro Gly Xaa Gly Val Pro
        420                 425                 430

Gly Xaa Gly Val Pro Gly Xaa Gly Val Pro Gly Xaa Gly Val Pro Gly
    435                 440                 445

Xaa Gly
    450

<210> SEQ ID NO 15
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide -continued

```
<220> FEATURE:
<221> NAME/KEY: MOD_RES
<222> LOCATION: (4)..(4)
<223> OTHER INFORMATION: Any hydrophilic amino acid
<220> FEATURE:
<221> NAME/KEY: MOD_RES
<222> LOCATION: (9)..(9)
<223> OTHER INFORMATION: Any hydrophilic amino acid
<220> FEATURE:
<221> NAME/KEY: MOD_RES
<222> LOCATION: (14)..(14)
<223> OTHER INFORMATION: Any hydrophilic amino acid
<220> FEATURE:
<221> NAME/KEY: MOD_RES
<222> LOCATION: (19)..(19)
<223> OTHER INFORMATION: Any hydrophilic amino acid
<220> FEATURE:
<221> NAME/KEY: MOD_RES
<222> LOCATION: (24)..(24)
<223> OTHER INFORMATION: Any hydrophilic amino acid
<220> FEATURE:
<221> NAME/KEY: MOD_RES
<222> LOCATION: (29)..(29)
<223> OTHER INFORMATION: Any hydrophilic amino acid
<220> FEATURE:
<221> NAME/KEY: MOD_RES
<222> LOCATION: (34)..(34)
<223> OTHER INFORMATION: Any hydrophilic amino acid
<220> FEATURE:
<221> NAME/KEY: MOD_RES
<222> LOCATION: (39)..(39)
<223> OTHER INFORMATION: Any hydrophilic amino acid
<220> FEATURE:
<221> NAME/KEY: MOD_RES
<222> LOCATION: (44)..(44)
<223> OTHER INFORMATION: Any hydrophilic amino acid
<220> FEATURE:
<221> NAME/KEY: MOD_RES
<222> LOCATION: (49)..(49)
<223> OTHER INFORMATION: Any hydrophilic amino acid
<220> FEATURE:
<221> NAME/KEY: MOD_RES
<222> LOCATION: (54)..(54)
<223> OTHER INFORMATION: Any hydrophilic amino acid
<220> FEATURE:
<221> NAME/KEY: MOD_RES
<222> LOCATION: (59)..(59)
<223> OTHER INFORMATION: Any hydrophilic amino acid
<220> FEATURE:
<221> NAME/KEY: MOD_RES
<222> LOCATION: (64)..(64)
<223> OTHER INFORMATION: Any hydrophilic amino acid
<220> FEATURE:
<221> NAME/KEY: MOD_RES
<222> LOCATION: (69)..(69)
<223> OTHER INFORMATION: Any hydrophilic amino acid
<220> FEATURE:
<221> NAME/KEY: MOD_RES
<222> LOCATION: (74)..(74)
<223> OTHER INFORMATION: Any hydrophilic amino acid
<220> FEATURE:
<221> NAME/KEY: MOD_RES
<222> LOCATION: (79)..(79)
<223> OTHER INFORMATION: Any hydrophilic amino acid
<220> FEATURE:
<221> NAME/KEY: MOD_RES
<222> LOCATION: (84)..(84)
<223> OTHER INFORMATION: Any hydrophilic amino acid
<220> FEATURE:
<221> NAME/KEY: MOD_RES
<222> LOCATION: (89)..(89)
<223> OTHER INFORMATION: Any hydrophilic amino acid
<220> FEATURE:
<221> NAME/KEY: MOD_RES
<222> LOCATION: (94)..(94)
<223> OTHER INFORMATION: Any hydrophilic amino acid
<220> FEATURE:
<221> NAME/KEY: MOD_RES
<222> LOCATION: (99)..(99)
```

```
<223> OTHER INFORMATION: Any hydrophilic amino acid
<220> FEATURE:
<221> NAME/KEY: MOD_RES
<222> LOCATION: (104)..(104)
<223> OTHER INFORMATION: Any hydrophilic amino acid
<220> FEATURE:
<221> NAME/KEY: MOD_RES
<222> LOCATION: (109)..(109)
<223> OTHER INFORMATION: Any hydrophilic amino acid
<220> FEATURE:
<221> NAME/KEY: MOD_RES
<222> LOCATION: (114)..(114)
<223> OTHER INFORMATION: Any hydrophilic amino acid
<220> FEATURE:
<221> NAME/KEY: MOD_RES
<222> LOCATION: (119)..(119)
<223> OTHER INFORMATION: Any hydrophilic amino acid
<220> FEATURE:
<221> NAME/KEY: MOD_RES
<222> LOCATION: (124)..(124)
<223> OTHER INFORMATION: Any hydrophilic amino acid
<220> FEATURE:
<221> NAME/KEY: MOD_RES
<222> LOCATION: (129)..(129)
<223> OTHER INFORMATION: Any hydrophilic amino acid
<220> FEATURE:
<221> NAME/KEY: MOD_RES
<222> LOCATION: (134)..(134)
<223> OTHER INFORMATION: Any hydrophilic amino acid
<220> FEATURE:
<221> NAME/KEY: MOD_RES
<222> LOCATION: (139)..(139)
<223> OTHER INFORMATION: Any hydrophilic amino acid
<220> FEATURE:
<221> NAME/KEY: MOD_RES
<222> LOCATION: (144)..(144)
<223> OTHER INFORMATION: Any hydrophilic amino acid
<220> FEATURE:
<221> NAME/KEY: MOD_RES
<222> LOCATION: (149)..(149)
<223> OTHER INFORMATION: Any hydrophilic amino acid
<220> FEATURE:
<221> NAME/KEY: MOD_RES
<222> LOCATION: (154)..(154)
<223> OTHER INFORMATION: Any hydrophilic amino acid
<220> FEATURE:
<221> NAME/KEY: MOD_RES
<222> LOCATION: (159)..(159)
<223> OTHER INFORMATION: Any hydrophilic amino acid
<220> FEATURE:
<221> NAME/KEY: MOD_RES
<222> LOCATION: (164)..(164)
<223> OTHER INFORMATION: Any hydrophilic amino acid
<220> FEATURE:
<221> NAME/KEY: MOD_RES
<222> LOCATION: (169)..(169)
<223> OTHER INFORMATION: Any hydrophilic amino acid
<220> FEATURE:
<221> NAME/KEY: MOD_RES
<222> LOCATION: (174)..(174)
<223> OTHER INFORMATION: Any hydrophilic amino acid
<220> FEATURE:
<221> NAME/KEY: MOD_RES
<222> LOCATION: (179)..(179)
<223> OTHER INFORMATION: Any hydrophilic amino acid
<220> FEATURE:
<221> NAME/KEY: MOD_RES
<222> LOCATION: (184)..(184)
<223> OTHER INFORMATION: Any hydrophilic amino acid
<220> FEATURE:
<221> NAME/KEY: MOD_RES
<222> LOCATION: (189)..(189)
<223> OTHER INFORMATION: Any hydrophilic amino acid
<220> FEATURE:
<221> NAME/KEY: MOD_RES
<222> LOCATION: (194)..(194)
<223> OTHER INFORMATION: Any hydrophilic amino acid
<220> FEATURE:
<221> NAME/KEY: MOD_RES
```

```
<222> LOCATION: (199)..(199)
<223> OTHER INFORMATION: Any hydrophilic amino acid
<220> FEATURE:
<221> NAME/KEY: MOD_RES
<222> LOCATION: (204)..(204)
<223> OTHER INFORMATION: Any hydrophilic amino acid
<220> FEATURE:
<221> NAME/KEY: MOD_RES
<222> LOCATION: (209)..(209)
<223> OTHER INFORMATION: Any hydrophilic amino acid
<220> FEATURE:
<221> NAME/KEY: MOD_RES
<222> LOCATION: (214)..(214)
<223> OTHER INFORMATION: Any hydrophilic amino acid
<220> FEATURE:
<221> NAME/KEY: MOD_RES
<222> LOCATION: (219)..(219)
<223> OTHER INFORMATION: Any hydrophilic amino acid
<220> FEATURE:
<221> NAME/KEY: MOD_RES
<222> LOCATION: (224)..(224)
<223> OTHER INFORMATION: Any hydrophilic amino acid
<220> FEATURE:
<221> NAME/KEY: MOD_RES
<222> LOCATION: (229)..(229)
<223> OTHER INFORMATION: Any hydrophilic amino acid
<220> FEATURE:
<221> NAME/KEY: MOD_RES
<222> LOCATION: (234)..(234)
<223> OTHER INFORMATION: Any hydrophilic amino acid
<220> FEATURE:
<221> NAME/KEY: MOD_RES
<222> LOCATION: (239)..(239)
<223> OTHER INFORMATION: Any hydrophilic amino acid
<220> FEATURE:
<221> NAME/KEY: MOD_RES
<222> LOCATION: (244)..(244)
<223> OTHER INFORMATION: Any hydrophilic amino acid
<220> FEATURE:
<221> NAME/KEY: MOD_RES
<222> LOCATION: (249)..(249)
<223> OTHER INFORMATION: Any hydrophilic amino acid
<220> FEATURE:
<221> NAME/KEY: MOD_RES
<222> LOCATION: (254)..(254)
<223> OTHER INFORMATION: Any hydrophilic amino acid
<220> FEATURE:
<221> NAME/KEY: MOD_RES
<222> LOCATION: (259)..(259)
<223> OTHER INFORMATION: Any hydrophilic amino acid
<220> FEATURE:
<221> NAME/KEY: MOD_RES
<222> LOCATION: (264)..(264)
<223> OTHER INFORMATION: Any hydrophilic amino acid
<220> FEATURE:
<221> NAME/KEY: MOD_RES
<222> LOCATION: (269)..(269)
<223> OTHER INFORMATION: Any hydrophilic amino acid
<220> FEATURE:
<221> NAME/KEY: MOD_RES
<222> LOCATION: (274)..(274)
<223> OTHER INFORMATION: Any hydrophilic amino acid
<220> FEATURE:
<221> NAME/KEY: MOD_RES
<222> LOCATION: (279)..(279)
<223> OTHER INFORMATION: Any hydrophilic amino acid
<220> FEATURE:
<221> NAME/KEY: MOD_RES
<222> LOCATION: (284)..(284)
<223> OTHER INFORMATION: Any hydrophilic amino acid
<220> FEATURE:
<221> NAME/KEY: MOD_RES
<222> LOCATION: (289)..(289)
<223> OTHER INFORMATION: Any hydrophilic amino acid
<220> FEATURE:
<221> NAME/KEY: MOD_RES
<222> LOCATION: (294)..(294)
<223> OTHER INFORMATION: Any hydrophilic amino acid
<220> FEATURE:
```

```
<221> NAME/KEY: MOD_RES
<222> LOCATION: (299)..(299)
<223> OTHER INFORMATION: Any hydrophilic amino acid
<220> FEATURE:
<221> NAME/KEY: MOD_RES
<222> LOCATION: (304)..(304)
<223> OTHER INFORMATION: Any hydrophilic amino acid
<220> FEATURE:
<221> NAME/KEY: MOD_RES
<222> LOCATION: (309)..(309)
<223> OTHER INFORMATION: Any hydrophilic amino acid
<220> FEATURE:
<221> NAME/KEY: MOD_RES
<222> LOCATION: (314)..(314)
<223> OTHER INFORMATION: Any hydrophilic amino acid
<220> FEATURE:
<221> NAME/KEY: MOD_RES
<222> LOCATION: (319)..(319)
<223> OTHER INFORMATION: Any hydrophilic amino acid
<220> FEATURE:
<221> NAME/KEY: MOD_RES
<222> LOCATION: (324)..(324)
<223> OTHER INFORMATION: Any hydrophilic amino acid
<220> FEATURE:
<221> NAME/KEY: MOD_RES
<222> LOCATION: (329)..(329)
<223> OTHER INFORMATION: Any hydrophilic amino acid
<220> FEATURE:
<221> NAME/KEY: MOD_RES
<222> LOCATION: (334)..(334)
<223> OTHER INFORMATION: Any hydrophilic amino acid
<220> FEATURE:
<221> NAME/KEY: MOD_RES
<222> LOCATION: (339)..(339)
<223> OTHER INFORMATION: Any hydrophilic amino acid
<220> FEATURE:
<221> NAME/KEY: MOD_RES
<222> LOCATION: (344)..(344)
<223> OTHER INFORMATION: Any hydrophilic amino acid
<220> FEATURE:
<221> NAME/KEY: MOD_RES
<222> LOCATION: (349)..(349)
<223> OTHER INFORMATION: Any hydrophilic amino acid
<220> FEATURE:
<221> NAME/KEY: MOD_RES
<222> LOCATION: (354)..(354)
<223> OTHER INFORMATION: Any hydrophilic amino acid
<220> FEATURE:
<221> NAME/KEY: MOD_RES
<222> LOCATION: (359)..(359)
<223> OTHER INFORMATION: Any hydrophilic amino acid
<220> FEATURE:
<221> NAME/KEY: MOD_RES
<222> LOCATION: (364)..(364)
<223> OTHER INFORMATION: Any hydrophilic amino acid
<220> FEATURE:
<221> NAME/KEY: MOD_RES
<222> LOCATION: (369)..(369)
<223> OTHER INFORMATION: Any hydrophilic amino acid
<220> FEATURE:
<221> NAME/KEY: MOD_RES
<222> LOCATION: (374)..(374)
<223> OTHER INFORMATION: Any hydrophilic amino acid
<220> FEATURE:
<221> NAME/KEY: MOD_RES
<222> LOCATION: (379)..(379)
<223> OTHER INFORMATION: Any hydrophilic amino acid
<220> FEATURE:
<221> NAME/KEY: MOD_RES
<222> LOCATION: (384)..(384)
<223> OTHER INFORMATION: Any hydrophilic amino acid
<220> FEATURE:
<221> NAME/KEY: MOD_RES
<222> LOCATION: (389)..(389)
<223> OTHER INFORMATION: Any hydrophilic amino acid
<220> FEATURE:
<221> NAME/KEY: MOD_RES
<222> LOCATION: (394)..(394)
<223> OTHER INFORMATION: Any hydrophilic amino acid
```

<220> FEATURE:
<221> NAME/KEY: MOD_RES
<222> LOCATION: (399)..(399)
<223> OTHER INFORMATION: Any hydrophilic amino acid
<220> FEATURE:
<221> NAME/KEY: MISC_FEATURE
<222> LOCATION: (1)..(400)
<223> OTHER INFORMATION: This sequence may encompass 20-80 "Val-Pro-Gly-
    Xaa-Gly" repeating units

<400> SEQUENCE: 15

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly

```
                355                 360                 365
Xaa Gly Val Pro Gly Xaa Gly Val Pro Gly Xaa Gly Val Pro Gly Xaa
        370                 375                 380

Gly Val Pro Gly Xaa Gly Val Pro Gly Xaa Gly Val Pro Gly Xaa Gly
385                 390                 395                 400

<210> SEQ ID NO 16
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Ser or a conservative amino acid substitute
      thereof
<220> FEATURE:
<221> NAME/KEY: MOD_RES
<222> LOCATION: (9)..(9)
<223> OTHER INFORMATION: Ser or a conservative amino acid substitute
      thereof
<220> FEATURE:
<221> NAME/KEY: MOD_RES
<222> LOCATION: (14)..(14)
<223> OTHER INFORMATION: Ser or a conservative amino acid substitute
      thereof
<220> FEATURE:
<221> NAME/KEY: MOD_RES
<222> LOCATION: (19)..(19)
<223> OTHER INFORMATION: Ser or a conservative amino acid substitute
      thereof
<220> FEATURE:
<221> NAME/KEY: MOD_RES
<222> LOCATION: (24)..(24)
<223> OTHER INFORMATION: Ser or a conservative amino acid substitute
      thereof
<220> FEATURE:
<221> NAME/KEY: MOD_RES
<222> LOCATION: (29)..(29)
<223> OTHER INFORMATION: Ser or a conservative amino acid substitute
      thereof
<220> FEATURE:
<221> NAME/KEY: MOD_RES
<222> LOCATION: (34)..(34)
<223> OTHER INFORMATION: Ser or a conservative amino acid substitute
      thereof
<220> FEATURE:
<221> NAME/KEY: MOD_RES
<222> LOCATION: (39)..(39)
<223> OTHER INFORMATION: Ser or a conservative amino acid substitute
      thereof
<220> FEATURE:
<221> NAME/KEY: MOD_RES
<222> LOCATION: (44)..(44)
<223> OTHER INFORMATION: Ser or a conservative amino acid substitute
      thereof
<220> FEATURE:
<221> NAME/KEY: MOD_RES
<222> LOCATION: (49)..(49)
<223> OTHER INFORMATION: Ser or a conservative amino acid substitute
      thereof
<220> FEATURE:
<221> NAME/KEY: MOD_RES
<222> LOCATION: (54)..(54)
<223> OTHER INFORMATION: Ser or a conservative amino acid substitute
      thereof
<220> FEATURE:
<221> NAME/KEY: MOD_RES
<222> LOCATION: (59)..(59)
<223> OTHER INFORMATION: Ser or a conservative amino acid substitute
      thereof
<220> FEATURE:
<221> NAME/KEY: MOD_RES
<222> LOCATION: (64)..(64)
```

```
<223> OTHER INFORMATION: Ser or a conservative amino acid substitute
      thereof
<220> FEATURE:
<221> NAME/KEY: MOD_RES
<222> LOCATION: (69)..(69)
<223> OTHER INFORMATION: Ser or a conservative amino acid substitute
      thereof
<220> FEATURE:
<221> NAME/KEY: MOD_RES
<222> LOCATION: (74)..(74)
<223> OTHER INFORMATION: Ser or a conservative amino acid substitute
      thereof
<220> FEATURE:
<221> NAME/KEY: MOD_RES
<222> LOCATION: (79)..(79)
<223> OTHER INFORMATION: Ser or a conservative amino acid substitute
      thereof
<220> FEATURE:
<221> NAME/KEY: MOD_RES
<222> LOCATION: (84)..(84)
<223> OTHER INFORMATION: Ser or a conservative amino acid substitute
      thereof
<220> FEATURE:
<221> NAME/KEY: MOD_RES
<222> LOCATION: (89)..(89)
<223> OTHER INFORMATION: Ser or a conservative amino acid substitute
      thereof
<220> FEATURE:
<221> NAME/KEY: MOD_RES
<222> LOCATION: (94)..(94)
<223> OTHER INFORMATION: Ser or a conservative amino acid substitute
      thereof
<220> FEATURE:
<221> NAME/KEY: MOD_RES
<222> LOCATION: (99)..(99)
<223> OTHER INFORMATION: Ser or a conservative amino acid substitute
      thereof
<220> FEATURE:
<221> NAME/KEY: MOD_RES
<222> LOCATION: (104)..(104)
<223> OTHER INFORMATION: Ser or a conservative amino acid substitute
      thereof
<220> FEATURE:
<221> NAME/KEY: MOD_RES
<222> LOCATION: (109)..(109)
<223> OTHER INFORMATION: Ser or a conservative amino acid substitute
      thereof
<220> FEATURE:
<221> NAME/KEY: MOD_RES
<222> LOCATION: (114)..(114)
<223> OTHER INFORMATION: Ser or a conservative amino acid substitute
      thereof
<220> FEATURE:
<221> NAME/KEY: MOD_RES
<222> LOCATION: (119)..(119)
<223> OTHER INFORMATION: Ser or a conservative amino acid substitute
      thereof
<220> FEATURE:
<221> NAME/KEY: MOD_RES
<222> LOCATION: (124)..(124)
<223> OTHER INFORMATION: Ser or a conservative amino acid substitute
      thereof
<220> FEATURE:
<221> NAME/KEY: MOD_RES
<222> LOCATION: (129)..(129)
<223> OTHER INFORMATION: Ser or a conservative amino acid substitute
      thereof
<220> FEATURE:
<221> NAME/KEY: MOD_RES
<222> LOCATION: (134)..(134)
<223> OTHER INFORMATION: Ser or a conservative amino acid substitute
      thereof
<220> FEATURE:
<221> NAME/KEY: MOD_RES
<222> LOCATION: (139)..(139)
<223> OTHER INFORMATION: Ser or a conservative amino acid substitute
      thereof
<220> FEATURE:
<221> NAME/KEY: MOD_RES
```

```
<222> LOCATION: (144)..(144)
<223> OTHER INFORMATION: Ser or a conservative amino acid substitute
      thereof
<220> FEATURE:
<221> NAME/KEY: MOD_RES
<222> LOCATION: (149)..(149)
<223> OTHER INFORMATION: Ser or a conservative amino acid substitute
      thereof
<220> FEATURE:
<221> NAME/KEY: MOD_RES
<222> LOCATION: (154)..(154)
<223> OTHER INFORMATION: Ser or a conservative amino acid substitute
      thereof
<220> FEATURE:
<221> NAME/KEY: MOD_RES
<222> LOCATION: (159)..(159)
<223> OTHER INFORMATION: Ser or a conservative amino acid substitute
      thereof
<220> FEATURE:
<221> NAME/KEY: MOD_RES
<222> LOCATION: (164)..(164)
<223> OTHER INFORMATION: Ser or a conservative amino acid substitute
      thereof
<220> FEATURE:
<221> NAME/KEY: MOD_RES
<222> LOCATION: (169)..(169)
<223> OTHER INFORMATION: Ser or a conservative amino acid substitute
      thereof
<220> FEATURE:
<221> NAME/KEY: MOD_RES
<222> LOCATION: (174)..(174)
<223> OTHER INFORMATION: Ser or a conservative amino acid substitute
      thereof
<220> FEATURE:
<221> NAME/KEY: MOD_RES
<222> LOCATION: (179)..(179)
<223> OTHER INFORMATION: Ser or a conservative amino acid substitute
      thereof
<220> FEATURE:
<221> NAME/KEY: MOD_RES
<222> LOCATION: (184)..(184)
<223> OTHER INFORMATION: Ser or a conservative amino acid substitute
      thereof
<220> FEATURE:
<221> NAME/KEY: MOD_RES
<222> LOCATION: (189)..(189)
<223> OTHER INFORMATION: Ser or a conservative amino acid substitute
      thereof
<220> FEATURE:
<221> NAME/KEY: MOD_RES
<222> LOCATION: (194)..(194)
<223> OTHER INFORMATION: Ser or a conservative amino acid substitute
      thereof
<220> FEATURE:
<221> NAME/KEY: MOD_RES
<222> LOCATION: (199)..(199)
<223> OTHER INFORMATION: Ser or a conservative amino acid substitute
      thereof
<220> FEATURE:
<221> NAME/KEY: MOD_RES
<222> LOCATION: (204)..(204)
<223> OTHER INFORMATION: Ser or a conservative amino acid substitute
      thereof
<220> FEATURE:
<221> NAME/KEY: MOD_RES
<222> LOCATION: (209)..(209)
<223> OTHER INFORMATION: Ser or a conservative amino acid substitute
      thereof
<220> FEATURE:
<221> NAME/KEY: MOD_RES
<222> LOCATION: (214)..(214)
<223> OTHER INFORMATION: Ser or a conservative amino acid substitute
      thereof
<220> FEATURE:
<221> NAME/KEY: MOD_RES
<222> LOCATION: (219)..(219)
<223> OTHER INFORMATION: Ser or a conservative amino acid substitute
      thereof
<220> FEATURE:
```

```
<221> NAME/KEY: MOD_RES
<222> LOCATION: (224)..(224)
<223> OTHER INFORMATION: Ser or a conservative amino acid substitute
      thereof
<220> FEATURE:
<221> NAME/KEY: MOD_RES
<222> LOCATION: (229)..(229)
<223> OTHER INFORMATION: Ser or a conservative amino acid substitute
      thereof
<220> FEATURE:
<221> NAME/KEY: MOD_RES
<222> LOCATION: (234)..(234)
<223> OTHER INFORMATION: Ser or a conservative amino acid substitute
      thereof
<220> FEATURE:
<221> NAME/KEY: MOD_RES
<222> LOCATION: (239)..(239)
<223> OTHER INFORMATION: Ser or a conservative amino acid substitute
      thereof
<220> FEATURE:
<221> NAME/KEY: MOD_RES
<222> LOCATION: (244)..(244)
<223> OTHER INFORMATION: Ser or a conservative amino acid substitute
      thereof
<220> FEATURE:
<221> NAME/KEY: MOD_RES
<222> LOCATION: (249)..(249)
<223> OTHER INFORMATION: Ser or a conservative amino acid substitute
      thereof
<220> FEATURE:
<221> NAME/KEY: MOD_RES
<222> LOCATION: (254)..(254)
<223> OTHER INFORMATION: Ser or a conservative amino acid substitute
      thereof
<220> FEATURE:
<221> NAME/KEY: MOD_RES
<222> LOCATION: (259)..(259)
<223> OTHER INFORMATION: Ser or a conservative amino acid substitute
      thereof
<220> FEATURE:
<221> NAME/KEY: MOD_RES
<222> LOCATION: (264)..(264)
<223> OTHER INFORMATION: Ser or a conservative amino acid substitute
      thereof
<220> FEATURE:
<221> NAME/KEY: MOD_RES
<222> LOCATION: (269)..(269)
<223> OTHER INFORMATION: Ser or a conservative amino acid substitute
      thereof
<220> FEATURE:
<221> NAME/KEY: MOD_RES
<222> LOCATION: (274)..(274)
<223> OTHER INFORMATION: Ser or a conservative amino acid substitute
      thereof
<220> FEATURE:
<221> NAME/KEY: MOD_RES
<222> LOCATION: (279)..(279)
<223> OTHER INFORMATION: Ser or a conservative amino acid substitute
      thereof
<220> FEATURE:
<221> NAME/KEY: MOD_RES
<222> LOCATION: (284)..(284)
<223> OTHER INFORMATION: Ser or a conservative amino acid substitute
      thereof
<220> FEATURE:
<221> NAME/KEY: MOD_RES
<222> LOCATION: (289)..(289)
<223> OTHER INFORMATION: Ser or a conservative amino acid substitute
      thereof
<220> FEATURE:
<221> NAME/KEY: MOD_RES
<222> LOCATION: (294)..(294)
<223> OTHER INFORMATION: Ser or a conservative amino acid substitute
      thereof
<220> FEATURE:
<221> NAME/KEY: MOD_RES
<222> LOCATION: (299)..(299)
<223> OTHER INFORMATION: Ser or a conservative amino acid substitute
      thereof
```

```
<220> FEATURE:
<221> NAME/KEY: MOD_RES
<222> LOCATION: (304)..(304)
<223> OTHER INFORMATION: Ser or a conservative amino acid substitute
      thereof
<220> FEATURE:
<221> NAME/KEY: MOD_RES
<222> LOCATION: (309)..(309)
<223> OTHER INFORMATION: Ser or a conservative amino acid substitute
      thereof
<220> FEATURE:
<221> NAME/KEY: MOD_RES
<222> LOCATION: (314)..(314)
<223> OTHER INFORMATION: Ser or a conservative amino acid substitute
      thereof
<220> FEATURE:
<221> NAME/KEY: MOD_RES
<222> LOCATION: (319)..(319)
<223> OTHER INFORMATION: Ser or a conservative amino acid substitute
      thereof
<220> FEATURE:
<221> NAME/KEY: MOD_RES
<222> LOCATION: (324)..(324)
<223> OTHER INFORMATION: Ser or a conservative amino acid substitute
      thereof
<220> FEATURE:
<221> NAME/KEY: MOD_RES
<222> LOCATION: (329)..(329)
<223> OTHER INFORMATION: Ser or a conservative amino acid substitute
      thereof
<220> FEATURE:
<221> NAME/KEY: MOD_RES
<222> LOCATION: (334)..(334)
<223> OTHER INFORMATION: Ser or a conservative amino acid substitute
      thereof
<220> FEATURE:
<221> NAME/KEY: MOD_RES
<222> LOCATION: (339)..(339)
<223> OTHER INFORMATION: Ser or a conservative amino acid substitute
      thereof
<220> FEATURE:
<221> NAME/KEY: MOD_RES
<222> LOCATION: (344)..(344)
<223> OTHER INFORMATION: Ser or a conservative amino acid substitute
      thereof
<220> FEATURE:
<221> NAME/KEY: MOD_RES
<222> LOCATION: (349)..(349)
<223> OTHER INFORMATION: Ser or a conservative amino acid substitute
      thereof
<220> FEATURE:
<221> NAME/KEY: MOD_RES
<222> LOCATION: (354)..(354)
<223> OTHER INFORMATION: Ser or a conservative amino acid substitute
      thereof
<220> FEATURE:
<221> NAME/KEY: MOD_RES
<222> LOCATION: (359)..(359)
<223> OTHER INFORMATION: Ser or a conservative amino acid substitute
      thereof
<220> FEATURE:
<221> NAME/KEY: MOD_RES
<222> LOCATION: (364)..(364)
<223> OTHER INFORMATION: Ser or a conservative amino acid substitute
      thereof
<220> FEATURE:
<221> NAME/KEY: MOD_RES
<222> LOCATION: (369)..(369)
<223> OTHER INFORMATION: Ser or a conservative amino acid substitute
      thereof
<220> FEATURE:
<221> NAME/KEY: MOD_RES
<222> LOCATION: (374)..(374)
<223> OTHER INFORMATION: Ser or a conservative amino acid substitute
      thereof
<220> FEATURE:
<221> NAME/KEY: MOD_RES
<222> LOCATION: (379)..(379)
<223> OTHER INFORMATION: Ser or a conservative amino acid substitute
```

```
<220> FEATURE:
<221> NAME/KEY: MOD_RES
<222> LOCATION: (384)..(384)
<223> OTHER INFORMATION: Ser or a conservative amino acid substitute
      thereof
<220> FEATURE:
<221> NAME/KEY: MOD_RES
<222> LOCATION: (389)..(389)
<223> OTHER INFORMATION: Ser or a conservative amino acid substitute
      thereof
<220> FEATURE:
<221> NAME/KEY: MOD_RES
<222> LOCATION: (394)..(394)
<223> OTHER INFORMATION: Ser or a conservative amino acid substitute
      thereof
<220> FEATURE:
<221> NAME/KEY: MOD_RES
<222> LOCATION: (399)..(399)
<223> OTHER INFORMATION: Ser or a conservative amino acid substitute
      thereof
<220> FEATURE:
<221> NAME/KEY: MOD_RES
<222> LOCATION: (404)..(404)
<223> OTHER INFORMATION: Ser or a conservative amino acid substitute
      thereof
<220> FEATURE:
<221> NAME/KEY: MOD_RES
<222> LOCATION: (409)..(409)
<223> OTHER INFORMATION: Ser or a conservative amino acid substitute
      thereof
<220> FEATURE:
<221> NAME/KEY: MOD_RES
<222> LOCATION: (414)..(414)
<223> OTHER INFORMATION: Ser or a conservative amino acid substitute
      thereof
<220> FEATURE:
<221> NAME/KEY: MOD_RES
<222> LOCATION: (419)..(419)
<223> OTHER INFORMATION: Ser or a conservative amino acid substitute
      thereof
<220> FEATURE:
<221> NAME/KEY: MOD_RES
<222> LOCATION: (424)..(424)
<223> OTHER INFORMATION: Ser or a conservative amino acid substitute
      thereof
<220> FEATURE:
<221> NAME/KEY: MOD_RES
<222> LOCATION: (429)..(429)
<223> OTHER INFORMATION: Ser or a conservative amino acid substitute
      thereof
<220> FEATURE:
<221> NAME/KEY: MOD_RES
<222> LOCATION: (434)..(434)
<223> OTHER INFORMATION: Ser or a conservative amino acid substitute
      thereof
<220> FEATURE:
<221> NAME/KEY: MOD_RES
<222> LOCATION: (439)..(439)
<223> OTHER INFORMATION: Ser or a conservative amino acid substitute
      thereof
<220> FEATURE:
<221> NAME/KEY: MOD_RES
<222> LOCATION: (444)..(444)
<223> OTHER INFORMATION: Ser or a conservative amino acid substitute
      thereof
<220> FEATURE:
<221> NAME/KEY: MOD_RES
<222> LOCATION: (449)..(449)
<223> OTHER INFORMATION: Ser or a conservative amino acid substitute
      thereof
<220> FEATURE:
<221> NAME/KEY: MISC_FEATURE
<222> LOCATION: (1)..(450)
<223> OTHER INFORMATION: This sequence may encompass 20-90 "Val-Pro-Gly-
      Xaa-Gly" repeating units

<400> SEQUENCE: 16
```

```
Val Pro Gly Xaa Gly Val Pro Gly Xaa Gly Val Pro Gly Xaa Gly Val
1               5                   10                  15
Pro Gly Xaa Gly Val Pro Gly Xaa Gly Val Pro Gly Xaa Gly Val Pro
            20                  25                  30
Gly Xaa Gly Val Pro Gly Xaa Gly Val Pro Gly Xaa Gly Val Pro Gly
        35                  40                  45
Xaa Gly Val Pro Gly Xaa Gly Val Pro Gly Xaa Gly Val Pro Gly Xaa
    50                  55                  60
Gly Val Pro Gly Xaa Gly Val Pro Gly Xaa Gly Val Pro Gly Xaa Gly
65                  70                  75                  80
Val Pro Gly Xaa Gly Val Pro Gly Xaa Gly Val Pro Gly Xaa Gly Val
                85                  90                  95
Pro Gly Xaa Gly Val Pro Gly Xaa Gly Val Pro Gly Xaa Gly Val Pro
            100                 105                 110
Gly Xaa Gly Val Pro Gly Xaa Gly Val Pro Gly Xaa Gly Val Pro Gly
        115                 120                 125
Xaa Gly Val Pro Gly Xaa Gly Val Pro Gly Xaa Gly Val Pro Gly Xaa
    130                 135                 140
Gly Val Pro Gly Xaa Gly Val Pro Gly Xaa Gly Val Pro Gly Xaa Gly
145                 150                 155                 160
Val Pro Gly Xaa Gly Val Pro Gly Xaa Gly Val Pro Gly Xaa Gly Val
                165                 170                 175
Pro Gly Xaa Gly Val Pro Gly Xaa Gly Val Pro Gly Xaa Gly Val Pro
            180                 185                 190
Gly Xaa Gly Val Pro Gly Xaa Gly Val Pro Gly Xaa Gly Val Pro Gly
        195                 200                 205
Xaa Gly Val Pro Gly Xaa Gly Val Pro Gly Xaa Gly Val Pro Gly Xaa
    210                 215                 220
Gly Val Pro Gly Xaa Gly Val Pro Gly Xaa Gly Val Pro Gly Xaa Gly
225                 230                 235                 240
Val Pro Gly Xaa Gly Val Pro Gly Xaa Gly Val Pro Gly Xaa Gly Val
                245                 250                 255
Pro Gly Xaa Gly Val Pro Gly Xaa Gly Val Pro Gly Xaa Gly Val Pro
            260                 265                 270
Gly Xaa Gly Val Pro Gly Xaa Gly Val Pro Gly Xaa Gly Val Pro Gly
        275                 280                 285
Xaa Gly Val Pro Gly Xaa Gly Val Pro Gly Xaa Gly Val Pro Gly Xaa
    290                 295                 300
Gly Val Pro Gly Xaa Gly Val Pro Gly Xaa Gly Val Pro Gly Xaa Gly
305                 310                 315                 320
Val Pro Gly Xaa Gly Val Pro Gly Xaa Gly Val Pro Gly Xaa Gly Val
                325                 330                 335
Pro Gly Xaa Gly Val Pro Gly Xaa Gly Val Pro Gly Xaa Gly Val Pro
            340                 345                 350
Gly Xaa Gly Val Pro Gly Xaa Gly Val Pro Gly Xaa Gly Val Pro Gly
        355                 360                 365
Xaa Gly Val Pro Gly Xaa Gly Val Pro Gly Xaa Gly Val Pro Gly Xaa
    370                 375                 380
Gly Val Pro Gly Xaa Gly Val Pro Gly Xaa Gly Val Pro Gly Xaa Gly
385                 390                 395                 400
Val Pro Gly Xaa Gly Val Pro Gly Xaa Gly Val Pro Gly Xaa Gly Val
                405                 410                 415
Pro Gly Xaa Gly Val Pro Gly Xaa Gly Val Pro Gly Xaa Gly Val Pro
```

```
                420             425             430
Gly Xaa Gly Val Pro Gly Xaa Gly Val Pro Gly Xaa Gly Val Pro Gly
        435             440             445

Xaa Gly
    450

<210> SEQ ID NO 17
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any hydrophobic amino acid
<220> FEATURE:
<221> NAME/KEY: MOD_RES
<222> LOCATION: (19)..(19)
<223> OTHER INFORMATION: Any hydrophobic amino acid
<220> FEATURE:
<221> NAME/KEY: MOD_RES
<222> LOCATION: (24)..(24)
<223> OTHER INFORMATION: Any hydrophobic amino acid
<220> FEATURE:
<221> NAME/KEY: MOD_RES
<222> LOCATION: (29)..(29)
<223> OTHER INFORMATION: Any hydrophobic amino acid
<220> FEATURE:
<221> NAME/KEY: MOD_RES
<222> LOCATION: (34)..(34)
<223> OTHER INFORMATION: Any hydrophobic amino acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: MOD_RES
<222> LOCATION: (44)..(44)
<223> OTHER INFORMATION: Any hydrophobic amino acid
<220> FEATURE:
<221> NAME/KEY: MOD_RES
<222> LOCATION: (49)..(49)
<223> OTHER INFORMATION: Any hydrophobic amino acid
<220> FEATURE:
<221> NAME/KEY: MOD_RES
<222> LOCATION: (54)..(54)
<223> OTHER INFORMATION: Any hydrophobic amino acid
<220> FEATURE:
<221> NAME/KEY: MOD_RES
<222> LOCATION: (59)..(59)
<223> OTHER INFORMATION: Any hydrophobic amino acid
<220> FEATURE:
<221> NAME/KEY: MOD_RES
<222> LOCATION: (64)..(64)
<223> OTHER INFORMATION: Any hydrophobic amino acid
<220> FEATURE:
<221> NAME/KEY: MOD_RES
<222> LOCATION: (69)..(69)
<223> OTHER INFORMATION: Any hydrophobic amino acid
<220> FEATURE:
<221> NAME/KEY: MOD_RES
<222> LOCATION: (74)..(74)
<223> OTHER INFORMATION: Any hydrophobic amino acid
<220> FEATURE:
<221> NAME/KEY: MOD_RES
<222> LOCATION: (79)..(79)
```

```
<223> OTHER INFORMATION: Any hydrophobic amino acid
<220> FEATURE:
<221> NAME/KEY: MOD_RES
<222> LOCATION: (84)..(84)
<223> OTHER INFORMATION: Any hydrophobic amino acid
<220> FEATURE:
<221> NAME/KEY: MOD_RES
<222> LOCATION: (89)..(89)
<223> OTHER INFORMATION: Any hydrophobic amino acid
<220> FEATURE:
<221> NAME/KEY: MOD_RES
<222> LOCATION: (94)..(94)
<223> OTHER INFORMATION: Any hydrophobic amino acid
<220> FEATURE:
<221> NAME/KEY: MOD_RES
<222> LOCATION: (99)..(99)
<223> OTHER INFORMATION: Any hydrophobic amino acid
<220> FEATURE:
<221> NAME/KEY: MOD_RES
<222> LOCATION: (104)..(104)
<223> OTHER INFORMATION: Any hydrophobic amino acid
<220> FEATURE:
<221> NAME/KEY: MOD_RES
<222> LOCATION: (109)..(109)
<223> OTHER INFORMATION: Any hydrophobic amino acid
<220> FEATURE:
<221> NAME/KEY: MOD_RES
<222> LOCATION: (114)..(114)
<223> OTHER INFORMATION: Any hydrophobic amino acid
<220> FEATURE:
<221> NAME/KEY: MOD_RES
<222> LOCATION: (119)..(119)
<223> OTHER INFORMATION: Any hydrophobic amino acid
<220> FEATURE:
<221> NAME/KEY: MOD_RES
<222> LOCATION: (124)..(124)
<223> OTHER INFORMATION: Any hydrophobic amino acid
<220> FEATURE:
<221> NAME/KEY: MOD_RES
<222> LOCATION: (129)..(129)
<223> OTHER INFORMATION: Any hydrophobic amino acid
<220> FEATURE:
<221> NAME/KEY: MOD_RES
<222> LOCATION: (134)..(134)
<223> OTHER INFORMATION: Any hydrophobic amino acid
<220> FEATURE:
<221> NAME/KEY: MOD_RES
<222> LOCATION: (139)..(139)
<223> OTHER INFORMATION: Any hydrophobic amino acid
<220> FEATURE:
<221> NAME/KEY: MOD_RES
<222> LOCATION: (144)..(144)
<223> OTHER INFORMATION: Any hydrophobic amino acid
<220> FEATURE:
<221> NAME/KEY: MOD_RES
<222> LOCATION: (149)..(149)
<223> OTHER INFORMATION: Any hydrophobic amino acid
<220> FEATURE:
<221> NAME/KEY: MOD_RES
<222> LOCATION: (154)..(154)
<223> OTHER INFORMATION: Any hydrophobic amino acid
<220> FEATURE:
<221> NAME/KEY: MOD_RES
<222> LOCATION: (159)..(159)
<223> OTHER INFORMATION: Any hydrophobic amino acid
<220> FEATURE:
<221> NAME/KEY: MOD_RES
<222> LOCATION: (164)..(164)
<223> OTHER INFORMATION: Any hydrophobic amino acid
<220> FEATURE:
<221> NAME/KEY: MOD_RES
<222> LOCATION: (169)..(169)
<223> OTHER INFORMATION: Any hydrophobic amino acid
<220> FEATURE:
<221> NAME/KEY: MOD_RES
<222> LOCATION: (174)..(174)
<223> OTHER INFORMATION: Any hydrophobic amino acid
<220> FEATURE:
<221> NAME/KEY: MOD_RES
```

-continued

```
<222> LOCATION: (179)..(179)
<223> OTHER INFORMATION: Any hydrophobic amino acid
<220> FEATURE:
<221> NAME/KEY: MOD_RES
<222> LOCATION: (184)..(184)
<223> OTHER INFORMATION: Any hydrophobic amino acid
<220> FEATURE:
<221> NAME/KEY: MOD_RES
<222> LOCATION: (189)..(189)
<223> OTHER INFORMATION: Any hydrophobic amino acid
<220> FEATURE:
<221> NAME/KEY: MOD_RES
<222> LOCATION: (194)..(194)
<223> OTHER INFORMATION: Any hydrophobic amino acid
<220> FEATURE:
<221> NAME/KEY: MOD_RES
<222> LOCATION: (199)..(199)
<223> OTHER INFORMATION: Any hydrophobic amino acid
<220> FEATURE:
<221> NAME/KEY: MOD_RES
<222> LOCATION: (204)..(204)
<223> OTHER INFORMATION: Any hydrophobic amino acid
<220> FEATURE:
<221> NAME/KEY: MOD_RES
<222> LOCATION: (209)..(209)
<223> OTHER INFORMATION: Any hydrophobic amino acid
<220> FEATURE:
<221> NAME/KEY: MOD_RES
<222> LOCATION: (214)..(214)
<223> OTHER INFORMATION: Any hydrophobic amino acid
<220> FEATURE:
<221> NAME/KEY: MOD_RES
<222> LOCATION: (219)..(219)
<223> OTHER INFORMATION: Any hydrophobic amino acid
<220> FEATURE:
<221> NAME/KEY: MOD_RES
<222> LOCATION: (224)..(224)
<223> OTHER INFORMATION: Any hydrophobic amino acid
<220> FEATURE:
<221> NAME/KEY: MOD_RES
<222> LOCATION: (229)..(229)
<223> OTHER INFORMATION: Any hydrophobic amino acid
<220> FEATURE:
<221> NAME/KEY: MOD_RES
<222> LOCATION: (234)..(234)
<223> OTHER INFORMATION: Any hydrophobic amino acid
<220> FEATURE:
<221> NAME/KEY: MOD_RES
<222> LOCATION: (239)..(239)
<223> OTHER INFORMATION: Any hydrophobic amino acid
<220> FEATURE:
<221> NAME/KEY: MOD_RES
<222> LOCATION: (244)..(244)
<223> OTHER INFORMATION: Any hydrophobic amino acid
<220> FEATURE:
<221> NAME/KEY: MOD_RES
<222> LOCATION: (249)..(249)
<223> OTHER INFORMATION: Any hydrophobic amino acid
<220> FEATURE:
<221> NAME/KEY: MOD_RES
<222> LOCATION: (254)..(254)
<223> OTHER INFORMATION: Any hydrophobic amino acid
<220> FEATURE:
<221> NAME/KEY: MOD_RES
<222> LOCATION: (259)..(259)
<223> OTHER INFORMATION: Any hydrophobic amino acid
<220> FEATURE:
<221> NAME/KEY: MOD_RES
<222> LOCATION: (264)..(264)
<223> OTHER INFORMATION: Any hydrophobic amino acid
<220> FEATURE:
<221> NAME/KEY: MOD_RES
<222> LOCATION: (269)..(269)
<223> OTHER INFORMATION: Any hydrophobic amino acid
<220> FEATURE:
<221> NAME/KEY: MOD_RES
<222> LOCATION: (274)..(274)
<223> OTHER INFORMATION: Any hydrophobic amino acid
<220> FEATURE:
```

```
<221> NAME/KEY: MOD_RES
<222> LOCATION: (279)..(279)
<223> OTHER INFORMATION: Any hydrophobic amino acid
<220> FEATURE:
<221> NAME/KEY: MOD_RES
<222> LOCATION: (284)..(284)
<223> OTHER INFORMATION: Any hydrophobic amino acid
<220> FEATURE:
<221> NAME/KEY: MOD_RES
<222> LOCATION: (289)..(289)
<223> OTHER INFORMATION: Any hydrophobic amino acid
<220> FEATURE:
<221> NAME/KEY: MOD_RES
<222> LOCATION: (294)..(294)
<223> OTHER INFORMATION: Any hydrophobic amino acid
<220> FEATURE:
<221> NAME/KEY: MOD_RES
<222> LOCATION: (299)..(299)
<223> OTHER INFORMATION: Any hydrophobic amino acid
<220> FEATURE:
<221> NAME/KEY: MISC_FEATURE
<222> LOCATION: (1)..(300)
<223> OTHER INFORMATION: This sequence may encompass 40-60 "Val-Pro-Gly-
      Xaa-Gly" repeating units

<400> SEQUENCE: 17

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
```

```
            275                 280                 285
Xaa Gly Val Pro Gly Xaa Gly Val Pro Gly Xaa Gly
    290                 295                 300

<210> SEQ ID NO 18
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(450)
<223> OTHER INFORMATION: This sequence may encompass 20-90 "Val-Pro-Gly-
      Ser-Gly" repeating units

<400> SEQUENCE: 18

Val Pro Gly Ser Gly Val Pro Gly Ser Gly Val Pro Gly Ser Gly Val
1               5                   10                  15

Pro Gly Ser Gly Val Pro Gly Ser Gly Val Pro Gly Ser Gly Val Pro
            20                  25                  30

Gly Ser Gly Val Pro Gly Ser Gly Val Pro Gly Ser Gly Val Pro Gly
        35                  40                  45

Ser Gly Val Pro Gly Ser Gly Val Pro Gly Ser Gly Val Pro Gly Ser
    50                  55                  60

Gly Val Pro Gly Ser Gly Val Pro Gly Ser Gly Val Pro Gly Ser Gly
65                  70                  75                  80

Val Pro Gly Ser Gly Val Pro Gly Ser Gly Val Pro Gly Ser Gly Val
                85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
        115                 120                 125

Ser Gly Val Pro Gly Ser Gly Val Pro Gly Ser Gly Val Pro Gly Ser
    130                 135                 140

Gly Val Pro Gly Ser Gly Val Pro Gly Ser Gly Val Pro Gly Ser Gly
145                 150                 155                 160

Val Pro Gly Ser Gly Val Pro Gly Ser Gly Val Pro Gly Ser Gly Val
                165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
        195                 200                 205

Ser Gly Val Pro Gly Ser Gly Val Pro Gly Ser Gly Val Pro Gly Ser
    210                 215                 220

Gly Val Pro Gly Ser Gly Val Pro Gly Ser Gly Val Pro Gly Ser Gly
225                 230                 235                 240

Val Pro Gly Ser Gly Val Pro Gly Ser Gly Val Pro Gly Ser Gly Val
                245                 250                 255

Pro Gly Ser Gly Val Pro Gly Ser Gly Val Pro Gly Ser Gly Val Pro
            260                 265                 270

Gly Ser Gly Val Pro Gly Ser Gly Val Pro Gly Ser Gly Val Pro Gly
        275                 280                 285

Ser Gly Val Pro Gly Ser Gly Val Pro Gly Ser Gly Val Pro Gly Ser
    290                 295                 300

Gly Val Pro Gly Ser Gly Val Pro Gly Ser Gly Val Pro Gly Ser Gly
```

```
                        305                 310                 315                 320
Val Pro Gly Ser Gly Val Pro Gly Ser Gly Val Pro Gly Ser Gly Val
                    325                 330                 335

Pro Gly Ser Gly Val Pro Gly Ser Gly Val Pro Gly Ser Gly Val Pro
                340                 345                 350

Gly Ser Gly Val Pro Gly Ser Gly Val Pro Gly Ser Gly Val Pro Gly
            355                 360                 365

Ser Gly Val Pro Gly Ser Gly Val Pro Gly Ser Gly Val Pro Gly Ser
        370                 375                 380

Gly Val Pro Gly Ser Gly Val Pro Gly Ser Gly Val Pro Gly Ser Gly
385                 390                 395                 400

Val Pro Gly Ser Gly Val Pro Gly Ser Gly Val Pro Gly Ser Gly Val
                405                 410                 415

Pro Gly Ser Gly Val Pro Gly Ser Gly Val Pro Gly Ser Gly Val Pro
            420                 425                 430

Gly Ser Gly Val Pro Gly Ser Gly Val Pro Gly Ser Gly Val Pro Gly
        435                 440                 445

Ser Gly
    450

<210> SEQ ID NO 19
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Ile or a conservative amino acid substitute
      thereof
<220> FEATURE:
<221> NAME/KEY: MOD_RES
<222> LOCATION: (9)..(9)
<223> OTHER INFORMATION: Ile or a conservative amino acid substitute
      thereof
<220> FEATURE:
<221> NAME/KEY: MOD_RES
<222> LOCATION: (14)..(14)
<223> OTHER INFORMATION: Ile or a conservative amino acid substitute
      thereof
<220> FEATURE:
<221> NAME/KEY: MOD_RES
<222> LOCATION: (19)..(19)
<223> OTHER INFORMATION: Ile or a conservative amino acid substitute
      thereof
<220> FEATURE:
<221> NAME/KEY: MOD_RES
<222> LOCATION: (24)..(24)
<223> OTHER INFORMATION: Ile or a conservative amino acid substitute
      thereof
<220> FEATURE:
<221> NAME/KEY: MOD_RES
<222> LOCATION: (29)..(29)
<223> OTHER INFORMATION: Ile or a conservative amino acid substitute
      thereof
<220> FEATURE:
<221> NAME/KEY: MOD_RES
<222> LOCATION: (34)..(34)
<223> OTHER INFORMATION: Ile or a conservative amino acid substitute
      thereof
<220> FEATURE:
<221> NAME/KEY: MOD_RES
<222> LOCATION: (39)..(39)
<223> OTHER INFORMATION: Ile or a conservative amino acid substitute
      thereof
<220> FEATURE:
<221> NAME/KEY: MOD_RES
```

```
<222> LOCATION: (44)..(44)
<223> OTHER INFORMATION: Ile or a conservative amino acid substitute
      thereof
<220> FEATURE:
<221> NAME/KEY: MOD_RES
<222> LOCATION: (49)..(49)
<223> OTHER INFORMATION: Ile or a conservative amino acid substitute
      thereof
<220> FEATURE:
<221> NAME/KEY: MOD_RES
<222> LOCATION: (54)..(54)
<223> OTHER INFORMATION: Ile or a conservative amino acid substitute
      thereof
<220> FEATURE:
<221> NAME/KEY: MOD_RES
<222> LOCATION: (59)..(59)
<223> OTHER INFORMATION: Ile or a conservative amino acid substitute
      thereof
<220> FEATURE:
<221> NAME/KEY: MOD_RES
<222> LOCATION: (64)..(64)
<223> OTHER INFORMATION: Ile or a conservative amino acid substitute
      thereof
<220> FEATURE:
<221> NAME/KEY: MOD_RES
<222> LOCATION: (69)..(69)
<223> OTHER INFORMATION: Ile or a conservative amino acid substitute
      thereof
<220> FEATURE:
<221> NAME/KEY: MOD_RES
<222> LOCATION: (74)..(74)
<223> OTHER INFORMATION: Ile or a conservative amino acid substitute
      thereof
<220> FEATURE:
<221> NAME/KEY: MOD_RES
<222> LOCATION: (79)..(79)
<223> OTHER INFORMATION: Ile or a conservative amino acid substitute
      thereof
<220> FEATURE:
<221> NAME/KEY: MOD_RES
<222> LOCATION: (84)..(84)
<223> OTHER INFORMATION: Ile or a conservative amino acid substitute
      thereof
<220> FEATURE:
<221> NAME/KEY: MOD_RES
<222> LOCATION: (89)..(89)
<223> OTHER INFORMATION: Ile or a conservative amino acid substitute
      thereof
<220> FEATURE:
<221> NAME/KEY: MOD_RES
<222> LOCATION: (94)..(94)
<223> OTHER INFORMATION: Ile or a conservative amino acid substitute
      thereof
<220> FEATURE:
<221> NAME/KEY: MOD_RES
<222> LOCATION: (99)..(99)
<223> OTHER INFORMATION: Ile or a conservative amino acid substitute
      thereof
<220> FEATURE:
<221> NAME/KEY: MOD_RES
<222> LOCATION: (104)..(104)
<223> OTHER INFORMATION: Ile or a conservative amino acid substitute
      thereof
<220> FEATURE:
<221> NAME/KEY: MOD_RES
<222> LOCATION: (109)..(109)
<223> OTHER INFORMATION: Ile or a conservative amino acid substitute
      thereof
<220> FEATURE:
<221> NAME/KEY: MOD_RES
<222> LOCATION: (114)..(114)
<223> OTHER INFORMATION: Ile or a conservative amino acid substitute
      thereof
<220> FEATURE:
<221> NAME/KEY: MOD_RES
<222> LOCATION: (119)..(119)
<223> OTHER INFORMATION: Ile or a conservative amino acid substitute
      thereof
<220> FEATURE:
```

```
<221> NAME/KEY: MOD_RES
<222> LOCATION: (124)..(124)
<223> OTHER INFORMATION: Ile or a conservative amino acid substitute
      thereof
<220> FEATURE:
<221> NAME/KEY: MOD_RES
<222> LOCATION: (129)..(129)
<223> OTHER INFORMATION: Ile or a conservative amino acid substitute
      thereof
<220> FEATURE:
<221> NAME/KEY: MOD_RES
<222> LOCATION: (134)..(134)
<223> OTHER INFORMATION: Ile or a conservative amino acid substitute
      thereof
<220> FEATURE:
<221> NAME/KEY: MOD_RES
<222> LOCATION: (139)..(139)
<223> OTHER INFORMATION: Ile or a conservative amino acid substitute
      thereof
<220> FEATURE:
<221> NAME/KEY: MOD_RES
<222> LOCATION: (144)..(144)
<223> OTHER INFORMATION: Ile or a conservative amino acid substitute
      thereof
<220> FEATURE:
<221> NAME/KEY: MOD_RES
<222> LOCATION: (149)..(149)
<223> OTHER INFORMATION: Ile or a conservative amino acid substitute
      thereof
<220> FEATURE:
<221> NAME/KEY: MOD_RES
<222> LOCATION: (154)..(154)
<223> OTHER INFORMATION: Ile or a conservative amino acid substitute
      thereof
<220> FEATURE:
<221> NAME/KEY: MOD_RES
<222> LOCATION: (159)..(159)
<223> OTHER INFORMATION: Ile or a conservative amino acid substitute
      thereof
<220> FEATURE:
<221> NAME/KEY: MOD_RES
<222> LOCATION: (164)..(164)
<223> OTHER INFORMATION: Ile or a conservative amino acid substitute
      thereof
<220> FEATURE:
<221> NAME/KEY: MOD_RES
<222> LOCATION: (169)..(169)
<223> OTHER INFORMATION: Ile or a conservative amino acid substitute
      thereof
<220> FEATURE:
<221> NAME/KEY: MOD_RES
<222> LOCATION: (174)..(174)
<223> OTHER INFORMATION: Ile or a conservative amino acid substitute
      thereof
<220> FEATURE:
<221> NAME/KEY: MOD_RES
<222> LOCATION: (179)..(179)
<223> OTHER INFORMATION: Ile or a conservative amino acid substitute
      thereof
<220> FEATURE:
<221> NAME/KEY: MOD_RES
<222> LOCATION: (184)..(184)
<223> OTHER INFORMATION: Ile or a conservative amino acid substitute
      thereof
<220> FEATURE:
<221> NAME/KEY: MOD_RES
<222> LOCATION: (189)..(189)
<223> OTHER INFORMATION: Ile or a conservative amino acid substitute
      thereof
<220> FEATURE:
<221> NAME/KEY: MOD_RES
<222> LOCATION: (194)..(194)
<223> OTHER INFORMATION: Ile or a conservative amino acid substitute
      thereof
<220> FEATURE:
<221> NAME/KEY: MOD_RES
<222> LOCATION: (199)..(199)
<223> OTHER INFORMATION: Ile or a conservative amino acid substitute
      thereof
```

```
<220> FEATURE:
<221> NAME/KEY: MOD_RES
<222> LOCATION: (204)..(204)
<223> OTHER INFORMATION: Ile or a conservative amino acid substitute
      thereof
<220> FEATURE:
<221> NAME/KEY: MOD_RES
<222> LOCATION: (209)..(209)
<223> OTHER INFORMATION: Ile or a conservative amino acid substitute
      thereof
<220> FEATURE:
<221> NAME/KEY: MOD_RES
<222> LOCATION: (214)..(214)
<223> OTHER INFORMATION: Ile or a conservative amino acid substitute
      thereof
<220> FEATURE:
<221> NAME/KEY: MOD_RES
<222> LOCATION: (219)..(219)
<223> OTHER INFORMATION: Ile or a conservative amino acid substitute
      thereof
<220> FEATURE:
<221> NAME/KEY: MOD_RES
<222> LOCATION: (224)..(224)
<223> OTHER INFORMATION: Ile or a conservative amino acid substitute
      thereof
<220> FEATURE:
<221> NAME/KEY: MOD_RES
<222> LOCATION: (229)..(229)
<223> OTHER INFORMATION: Ile or a conservative amino acid substitute
      thereof
<220> FEATURE:
<221> NAME/KEY: MOD_RES
<222> LOCATION: (234)..(234)
<223> OTHER INFORMATION: Ile or a conservative amino acid substitute
      thereof
<220> FEATURE:
<221> NAME/KEY: MOD_RES
<222> LOCATION: (239)..(239)
<223> OTHER INFORMATION: Ile or a conservative amino acid substitute
      thereof
<220> FEATURE:
<221> NAME/KEY: MOD_RES
<222> LOCATION: (244)..(244)
<223> OTHER INFORMATION: Ile or a conservative amino acid substitute
      thereof
<220> FEATURE:
<221> NAME/KEY: MOD_RES
<222> LOCATION: (249)..(249)
<223> OTHER INFORMATION: Ile or a conservative amino acid substitute
      thereof
<220> FEATURE:
<221> NAME/KEY: MOD_RES
<222> LOCATION: (254)..(254)
<223> OTHER INFORMATION: Ile or a conservative amino acid substitute
      thereof
<220> FEATURE:
<221> NAME/KEY: MOD_RES
<222> LOCATION: (259)..(259)
<223> OTHER INFORMATION: Ile or a conservative amino acid substitute
      thereof
<220> FEATURE:
<221> NAME/KEY: MOD_RES
<222> LOCATION: (264)..(264)
<223> OTHER INFORMATION: Ile or a conservative amino acid substitute
      thereof
<220> FEATURE:
<221> NAME/KEY: MOD_RES
<222> LOCATION: (269)..(269)
<223> OTHER INFORMATION: Ile or a conservative amino acid substitute
      thereof
<220> FEATURE:
<221> NAME/KEY: MOD_RES
<222> LOCATION: (274)..(274)
<223> OTHER INFORMATION: Ile or a conservative amino acid substitute
      thereof
<220> FEATURE:
<221> NAME/KEY: MOD_RES
<222> LOCATION: (279)..(279)
<223> OTHER INFORMATION: Ile or a conservative amino acid substitute
```

```
      thereof
<220> FEATURE:
<221> NAME/KEY: MOD_RES
<222> LOCATION: (284)..(284)
<223> OTHER INFORMATION: Ile or a conservative amino acid substitute
      thereof
<220> FEATURE:
<221> NAME/KEY: MOD_RES
<222> LOCATION: (289)..(289)
<223> OTHER INFORMATION: Ile or a conservative amino acid substitute
      thereof
<220> FEATURE:
<221> NAME/KEY: MOD_RES
<222> LOCATION: (294)..(294)
<223> OTHER INFORMATION: Ile or a conservative amino acid substitute
      thereof
<220> FEATURE:
<221> NAME/KEY: MOD_RES
<222> LOCATION: (299)..(299)
<223> OTHER INFORMATION: Ile or a conservative amino acid substitute
      thereof
<220> FEATURE:
<221> NAME/KEY: MOD_RES
<222> LOCATION: (304)..(304)
<223> OTHER INFORMATION: Ile or a conservative amino acid substitute
      thereof
<220> FEATURE:
<221> NAME/KEY: MOD_RES
<222> LOCATION: (309)..(309)
<223> OTHER INFORMATION: Ile or a conservative amino acid substitute
      thereof
<220> FEATURE:
<221> NAME/KEY: MOD_RES
<222> LOCATION: (314)..(314)
<223> OTHER INFORMATION: Ile or a conservative amino acid substitute
      thereof
<220> FEATURE:
<221> NAME/KEY: MOD_RES
<222> LOCATION: (319)..(319)
<223> OTHER INFORMATION: Ile or a conservative amino acid substitute
      thereof
<220> FEATURE:
<221> NAME/KEY: MOD_RES
<222> LOCATION: (324)..(324)
<223> OTHER INFORMATION: Ile or a conservative amino acid substitute
      thereof
<220> FEATURE:
<221> NAME/KEY: MOD_RES
<222> LOCATION: (329)..(329)
<223> OTHER INFORMATION: Ile or a conservative amino acid substitute
      thereof
<220> FEATURE:
<221> NAME/KEY: MOD_RES
<222> LOCATION: (334)..(334)
<223> OTHER INFORMATION: Ile or a conservative amino acid substitute
      thereof
<220> FEATURE:
<221> NAME/KEY: MOD_RES
<222> LOCATION: (339)..(339)
<223> OTHER INFORMATION: Ile or a conservative amino acid substitute
      thereof
<220> FEATURE:
<221> NAME/KEY: MOD_RES
<222> LOCATION: (344)..(344)
<223> OTHER INFORMATION: Ile or a conservative amino acid substitute
      thereof
<220> FEATURE:
<221> NAME/KEY: MOD_RES
<222> LOCATION: (349)..(349)
<223> OTHER INFORMATION: Ile or a conservative amino acid substitute
      thereof
<220> FEATURE:
<221> NAME/KEY: MOD_RES
<222> LOCATION: (354)..(354)
<223> OTHER INFORMATION: Ile or a conservative amino acid substitute
      thereof
<220> FEATURE:
<221> NAME/KEY: MOD_RES
<222> LOCATION: (359)..(359)
```

```
<223> OTHER INFORMATION: Ile or a conservative amino acid substitute
      thereof
<220> FEATURE:
<221> NAME/KEY: MOD_RES
<222> LOCATION: (364)..(364)
<223> OTHER INFORMATION: Ile or a conservative amino acid substitute
      thereof
<220> FEATURE:
<221> NAME/KEY: MOD_RES
<222> LOCATION: (369)..(369)
<223> OTHER INFORMATION: Ile or a conservative amino acid substitute
      thereof
<220> FEATURE:
<221> NAME/KEY: MOD_RES
<222> LOCATION: (374)..(374)
<223> OTHER INFORMATION: Ile or a conservative amino acid substitute
      thereof
<220> FEATURE:
<221> NAME/KEY: MOD_RES
<222> LOCATION: (379)..(379)
<223> OTHER INFORMATION: Ile or a conservative amino acid substitute
      thereof
<220> FEATURE:
<221> NAME/KEY: MOD_RES
<222> LOCATION: (384)..(384)
<223> OTHER INFORMATION: Ile or a conservative amino acid substitute
      thereof
<220> FEATURE:
<221> NAME/KEY: MOD_RES
<222> LOCATION: (389)..(389)
<223> OTHER INFORMATION: Ile or a conservative amino acid substitute
      thereof
<220> FEATURE:
<221> NAME/KEY: MOD_RES
<222> LOCATION: (394)..(394)
<223> OTHER INFORMATION: Ile or a conservative amino acid substitute
      thereof
<220> FEATURE:
<221> NAME/KEY: MOD_RES
<222> LOCATION: (399)..(399)
<223> OTHER INFORMATION: Ile or a conservative amino acid substitute
      thereof
<220> FEATURE:
<221> NAME/KEY: MOD_RES
<222> LOCATION: (404)..(404)
<223> OTHER INFORMATION: Ile or a conservative amino acid substitute
      thereof
<220> FEATURE:
<221> NAME/KEY: MOD_RES
<222> LOCATION: (409)..(409)
<223> OTHER INFORMATION: Ile or a conservative amino acid substitute
      thereof
<220> FEATURE:
<221> NAME/KEY: MOD_RES
<222> LOCATION: (414)..(414)
<223> OTHER INFORMATION: Ile or a conservative amino acid substitute
      thereof
<220> FEATURE:
<221> NAME/KEY: MOD_RES
<222> LOCATION: (419)..(419)
<223> OTHER INFORMATION: Ile or a conservative amino acid substitute
      thereof
<220> FEATURE:
<221> NAME/KEY: MOD_RES
<222> LOCATION: (424)..(424)
<223> OTHER INFORMATION: Ile or a conservative amino acid substitute
      thereof
<220> FEATURE:
<221> NAME/KEY: MOD_RES
<222> LOCATION: (429)..(429)
<223> OTHER INFORMATION: Ile or a conservative amino acid substitute
      thereof
<220> FEATURE:
<221> NAME/KEY: MOD_RES
<222> LOCATION: (434)..(434)
<223> OTHER INFORMATION: Ile or a conservative amino acid substitute
      thereof
<220> FEATURE:
<221> NAME/KEY: MOD_RES
```

```
<222> LOCATION: (439)..(439)
<223> OTHER INFORMATION: Ile or a conservative amino acid substitute
      thereof
<220> FEATURE:
<221> NAME/KEY: MOD_RES
<222> LOCATION: (444)..(444)
<223> OTHER INFORMATION: Ile or a conservative amino acid substitute
      thereof
<220> FEATURE:
<221> NAME/KEY: MOD_RES
<222> LOCATION: (449)..(449)
<223> OTHER INFORMATION: Ile or a conservative amino acid substitute
      thereof
<220> FEATURE:
<221> NAME/KEY: MISC_FEATURE
<222> LOCATION: (1)..(450)
<223> OTHER INFORMATION: This sequence may encompass 20-90 "Val-Pro-Gly-
      Xaa-Gly" repeating units

<400> SEQUENCE: 19

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
```

```
305                 310                 315                 320
Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly
        355                 360                 365

Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
                405                 410                 415

Pro Gly Xaa Gly Val Pro Gly Xaa Gly Val Pro Gly Xaa Gly Val Pro
            420                 425                 430

Gly Xaa Gly Val Pro Gly Xaa Gly Val Pro Gly Xaa Gly Val Pro Gly
        435                 440                 445

Xaa Gly
    450

<210> SEQ ID NO 20
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any hydrophilic amino acid
<220> FEATURE:
<221> NAME/KEY: MOD_RES
<222> LOCATION: (9)..(9)
<223> OTHER INFORMATION: Any hydrophilic amino acid
<220> FEATURE:
<221> NAME/KEY: MOD_RES
<222> LOCATION: (14)..(14)
<223> OTHER INFORMATION: Any hydrophilic amino acid
<220> FEATURE:
<221> NAME/KEY: MOD_RES
<222> LOCATION: (19)..(19)
<223> OTHER INFORMATION: Any hydrophilic amino acid
<220> FEATURE:
<221> NAME/KEY: MOD_RES
<222> LOCATION: (24)..(24)
<223> OTHER INFORMATION: Any hydrophilic amino acid
<220> FEATURE:
<221> NAME/KEY: MOD_RES
<222> LOCATION: (29)..(29)
<223> OTHER INFORMATION: Any hydrophilic amino acid
<220> FEATURE:
<221> NAME/KEY: MOD_RES
<222> LOCATION: (34)..(34)
<223> OTHER INFORMATION: Any hydrophilic amino acid
<220> FEATURE:
<221> NAME/KEY: MOD_RES
<222> LOCATION: (39)..(39)
<223> OTHER INFORMATION: Any hydrophilic amino acid
<220> FEATURE:
<221> NAME/KEY: MOD_RES
<222> LOCATION: (44)..(44)
<223> OTHER INFORMATION: Any hydrophilic amino acid
<220> FEATURE:
<221> NAME/KEY: MOD_RES
<222> LOCATION: (49)..(49)
<223> OTHER INFORMATION: Any hydrophilic amino acid
<220> FEATURE:
<221> NAME/KEY: MOD_RES
```

```
<222> LOCATION: (54)..(54)
<223> OTHER INFORMATION: Any hydrophilic amino acid
<220> FEATURE:
<221> NAME/KEY: MOD_RES
<222> LOCATION: (59)..(59)
<223> OTHER INFORMATION: Any hydrophilic amino acid
<220> FEATURE:
<221> NAME/KEY: MOD_RES
<222> LOCATION: (64)..(64)
<223> OTHER INFORMATION: Any hydrophilic amino acid
<220> FEATURE:
<221> NAME/KEY: MOD_RES
<222> LOCATION: (69)..(69)
<223> OTHER INFORMATION: Any hydrophilic amino acid
<220> FEATURE:
<221> NAME/KEY: MOD_RES
<222> LOCATION: (74)..(74)
<223> OTHER INFORMATION: Any hydrophilic amino acid
<220> FEATURE:
<221> NAME/KEY: MOD_RES
<222> LOCATION: (79)..(79)
<223> OTHER INFORMATION: Any hydrophilic amino acid
<220> FEATURE:
<221> NAME/KEY: MOD_RES
<222> LOCATION: (84)..(84)
<223> OTHER INFORMATION: Any hydrophilic amino acid
<220> FEATURE:
<221> NAME/KEY: MOD_RES
<222> LOCATION: (89)..(89)
<223> OTHER INFORMATION: Any hydrophilic amino acid
<220> FEATURE:
<221> NAME/KEY: MOD_RES
<222> LOCATION: (94)..(94)
<223> OTHER INFORMATION: Any hydrophilic amino acid
<220> FEATURE:
<221> NAME/KEY: MOD_RES
<222> LOCATION: (99)..(99)
<223> OTHER INFORMATION: Any hydrophilic amino acid
<220> FEATURE:
<221> NAME/KEY: MOD_RES
<222> LOCATION: (104)..(104)
<223> OTHER INFORMATION: Any hydrophilic amino acid
<220> FEATURE:
<221> NAME/KEY: MOD_RES
<222> LOCATION: (109)..(109)
<223> OTHER INFORMATION: Any hydrophilic amino acid
<220> FEATURE:
<221> NAME/KEY: MOD_RES
<222> LOCATION: (114)..(114)
<223> OTHER INFORMATION: Any hydrophilic amino acid
<220> FEATURE:
<221> NAME/KEY: MOD_RES
<222> LOCATION: (119)..(119)
<223> OTHER INFORMATION: Any hydrophilic amino acid
<220> FEATURE:
<221> NAME/KEY: MOD_RES
<222> LOCATION: (124)..(124)
<223> OTHER INFORMATION: Any hydrophilic amino acid
<220> FEATURE:
<221> NAME/KEY: MOD_RES
<222> LOCATION: (129)..(129)
<223> OTHER INFORMATION: Any hydrophilic amino acid
<220> FEATURE:
<221> NAME/KEY: MOD_RES
<222> LOCATION: (134)..(134)
<223> OTHER INFORMATION: Any hydrophilic amino acid
<220> FEATURE:
<221> NAME/KEY: MOD_RES
<222> LOCATION: (139)..(139)
<223> OTHER INFORMATION: Any hydrophilic amino acid
<220> FEATURE:
<221> NAME/KEY: MOD_RES
<222> LOCATION: (144)..(144)
<223> OTHER INFORMATION: Any hydrophilic amino acid
<220> FEATURE:
<221> NAME/KEY: MOD_RES
<222> LOCATION: (149)..(149)
<223> OTHER INFORMATION: Any hydrophilic amino acid
<220> FEATURE:
```

-continued

```
<221> NAME/KEY: MOD_RES
<222> LOCATION: (154)..(154)
<223> OTHER INFORMATION: Any hydrophilic amino acid
<220> FEATURE:
<221> NAME/KEY: MOD_RES
<222> LOCATION: (159)..(159)
<223> OTHER INFORMATION: Any hydrophilic amino acid
<220> FEATURE:
<221> NAME/KEY: MOD_RES
<222> LOCATION: (164)..(164)
<223> OTHER INFORMATION: Any hydrophilic amino acid
<220> FEATURE:
<221> NAME/KEY: MOD_RES
<222> LOCATION: (169)..(169)
<223> OTHER INFORMATION: Any hydrophilic amino acid
<220> FEATURE:
<221> NAME/KEY: MOD_RES
<222> LOCATION: (174)..(174)
<223> OTHER INFORMATION: Any hydrophilic amino acid
<220> FEATURE:
<221> NAME/KEY: MOD_RES
<222> LOCATION: (179)..(179)
<223> OTHER INFORMATION: Any hydrophilic amino acid
<220> FEATURE:
<221> NAME/KEY: MOD_RES
<222> LOCATION: (184)..(184)
<223> OTHER INFORMATION: Any hydrophilic amino acid
<220> FEATURE:
<221> NAME/KEY: MOD_RES
<222> LOCATION: (189)..(189)
<223> OTHER INFORMATION: Any hydrophilic amino acid
<220> FEATURE:
<221> NAME/KEY: MOD_RES
<222> LOCATION: (194)..(194)
<223> OTHER INFORMATION: Any hydrophilic amino acid
<220> FEATURE:
<221> NAME/KEY: MOD_RES
<222> LOCATION: (199)..(199)
<223> OTHER INFORMATION: Any hydrophilic amino acid
<220> FEATURE:
<221> NAME/KEY: MOD_RES
<222> LOCATION: (204)..(204)
<223> OTHER INFORMATION: Any hydrophilic amino acid
<220> FEATURE:
<221> NAME/KEY: MOD_RES
<222> LOCATION: (209)..(209)
<223> OTHER INFORMATION: Any hydrophilic amino acid
<220> FEATURE:
<221> NAME/KEY: MOD_RES
<222> LOCATION: (214)..(214)
<223> OTHER INFORMATION: Any hydrophilic amino acid
<220> FEATURE:
<221> NAME/KEY: MOD_RES
<222> LOCATION: (219)..(219)
<223> OTHER INFORMATION: Any hydrophilic amino acid
<220> FEATURE:
<221> NAME/KEY: MOD_RES
<222> LOCATION: (224)..(224)
<223> OTHER INFORMATION: Any hydrophilic amino acid
<220> FEATURE:
<221> NAME/KEY: MOD_RES
<222> LOCATION: (229)..(229)
<223> OTHER INFORMATION: Any hydrophilic amino acid
<220> FEATURE:
<221> NAME/KEY: MOD_RES
<222> LOCATION: (234)..(234)
<223> OTHER INFORMATION: Any hydrophilic amino acid
<220> FEATURE:
<221> NAME/KEY: MOD_RES
<222> LOCATION: (239)..(239)
<223> OTHER INFORMATION: Any hydrophilic amino acid
<220> FEATURE:
<221> NAME/KEY: MOD_RES
<222> LOCATION: (244)..(244)
<223> OTHER INFORMATION: Any hydrophilic amino acid
<220> FEATURE:
<221> NAME/KEY: MOD_RES
<222> LOCATION: (249)..(249)
<223> OTHER INFORMATION: Any hydrophilic amino acid
```

```
<220> FEATURE:
<221> NAME/KEY: MOD_RES
<222> LOCATION: (254)..(254)
<223> OTHER INFORMATION: Any hydrophilic amino acid
<220> FEATURE:
<221> NAME/KEY: MOD_RES
<222> LOCATION: (259)..(259)
<223> OTHER INFORMATION: Any hydrophilic amino acid
<220> FEATURE:
<221> NAME/KEY: MOD_RES
<222> LOCATION: (264)..(264)
<223> OTHER INFORMATION: Any hydrophilic amino acid
<220> FEATURE:
<221> NAME/KEY: MOD_RES
<222> LOCATION: (269)..(269)
<223> OTHER INFORMATION: Any hydrophilic amino acid
<220> FEATURE:
<221> NAME/KEY: MOD_RES
<222> LOCATION: (274)..(274)
<223> OTHER INFORMATION: Any hydrophilic amino acid
<220> FEATURE:
<221> NAME/KEY: MOD_RES
<222> LOCATION: (279)..(279)
<223> OTHER INFORMATION: Any hydrophilic amino acid
<220> FEATURE:
<221> NAME/KEY: MOD_RES
<222> LOCATION: (284)..(284)
<223> OTHER INFORMATION: Any hydrophilic amino acid
<220> FEATURE:
<221> NAME/KEY: MOD_RES
<222> LOCATION: (289)..(289)
<223> OTHER INFORMATION: Any hydrophilic amino acid
<220> FEATURE:
<221> NAME/KEY: MOD_RES
<222> LOCATION: (294)..(294)
<223> OTHER INFORMATION: Any hydrophilic amino acid
<220> FEATURE:
<221> NAME/KEY: MOD_RES
<222> LOCATION: (299)..(299)
<223> OTHER INFORMATION: Any hydrophilic amino acid
<220> FEATURE:
<221> NAME/KEY: MISC_FEATURE
<222> LOCATION: (1)..(300)
<223> OTHER INFORMATION: This sequence may encompass 40-60 "Val-Pro-Gly-
      Xaa-Gly" repeating units

<400> SEQUENCE: 20

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
```

165                 170                 175
Pro Gly Xaa Gly Val Pro Gly Xaa Gly Val Pro Gly Xaa Gly Val Pro
            180                 185                 190
Gly Xaa Gly Val Pro Gly Xaa Gly Val Pro Gly Xaa Gly Val Pro Gly
        195                 200                 205
Xaa Gly Val Pro Gly Xaa Gly Val Pro Gly Xaa Gly Val Pro Gly Xaa
    210                 215                 220
Gly Val Pro Gly Xaa Gly Val Pro Gly Xaa Gly Val Pro Gly Xaa Gly
225                 230                 235                 240
Val Pro Gly Xaa Gly Val Pro Gly Xaa Gly Val Pro Gly Xaa Gly Val
            245                 250                 255
Pro Gly Xaa Gly Val Pro Gly Xaa Gly Val Pro Gly Xaa Gly Val Pro
        260                 265                 270
Gly Xaa Gly Val Pro Gly Xaa Gly Val Pro Gly Xaa Gly Val Pro Gly
    275                 280                 285
Xaa Gly Val Pro Gly Xaa Gly Val Pro Gly Xaa Gly
    290                 295                 300

<210> SEQ ID NO 21
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Pro Gly Ile Gly Val Pro Gly Ile Gly Val Pro Gly Ile Gly Val
1               5                   10                  15
Pro Gly Ile Gly Val Pro Gly Ile Gly Val Pro Gly Ile Gly Val Pro
            20                  25                  30
Gly Ile Gly Val Pro Gly Ile Gly Val Pro Gly Ile Gly Val Pro Gly
        35                  40                  45
Ile Gly Val Pro Gly Ile Gly Val Pro Gly Ile Gly Val Pro Gly Ile
    50                  55                  60
Gly Val Pro Gly Ile Gly Val Pro Gly Ile Gly Val Pro Gly Ile Gly
65                  70                  75                  80
Val Pro Gly Ile Gly Val Pro Gly Ile Gly Val Pro Gly Ile Gly Val
            85                  90                  95
Pro Gly Ile Gly Val Pro Gly Ile Gly Val Pro Gly Ile Gly Val Pro
        100                 105                 110
Gly Ile Gly Val Pro Gly Ile Gly Val Pro Gly Ile Gly Val Pro Gly
    115                 120                 125
Ile Gly Val Pro Gly Ile Gly Val Pro Gly Ile Gly Val Pro Gly Ile
    130                 135                 140
Gly Val Pro Gly Ile Gly Val Pro Gly Ile Gly Val Pro Gly Ile Gly
145                 150                 155                 160
Val Pro Gly Ile Gly Val Pro Gly Ile Gly Val Pro Gly Ile Gly Val
            165                 170                 175
Pro Gly Ile Gly Val Pro Gly Ile Gly Val Pro Gly Ile Gly Val Pro
        180                 185                 190
Gly Ile Gly Val Pro Gly Ile Gly Val Pro Gly Ile Gly Val Pro Gly
    195                 200                 205
Ile Gly Val Pro Gly Ile Gly Val Pro Gly Ile Gly Val Pro Gly Ile
    210                 215                 220

Gly Val Pro Gly Ile Gly Val Pro Gly Ile Gly Val Pro Gly Ile Gly
225                 230                 235                 240

<210> SEQ ID NO 22
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Pro Gly Ser Gly Val Pro Gly Ser Gly Val Pro Gly Ser Gly Val
1               5                   10                  15

Pro Gly Ser Gly Val Pro Gly Ser Gly Val Pro Gly Ser Gly Val Pro
            20                  25                  30

Gly Ser Gly Val Pro Gly Ser Gly Val Pro Gly Ser Gly Val Pro Gly
        35                  40                  45

Ser Gly Val Pro Gly Ser Gly Val Pro Gly Ser Gly Val Pro Gly Ser
    50                  55                  60

Gly Val Pro Gly Ser Gly Val Pro Gly Ser Gly Val Pro Gly Ser Gly
65                  70                  75                  80

Val Pro Gly Ser Gly Val Pro Gly Ser Gly Val Pro Gly Ser Gly Val
                85                  90                  95

Pro Gly Ser Gly Val Pro Gly Ser Gly Val Pro Gly Ser Gly Val Pro
            100                 105                 110

Gly Ser Gly Val Pro Gly Ser Gly Val Pro Gly Ser Gly Val Pro Gly
        115                 120                 125

Ser Gly Val Pro Gly Ser Gly Val Pro Gly Ser Gly Val Pro Gly Ser
    130                 135                 140

Gly Val Pro Gly Ser Gly Val Pro Gly Ser Gly Val Pro Gly Ser Gly
145                 150                 155                 160

Val Pro Gly Ser Gly Val Pro Gly Ser Gly Val Pro Gly Ser Gly Val
                165                 170                 175

Pro Gly Ser Gly Val Pro Gly Ser Gly Val Pro Gly Ser Gly Val Pro
            180                 185                 190

Gly Ser Gly Val Pro Gly Ser Gly Val Pro Gly Ser Gly Val Pro Gly
        195                 200                 205

Ser Gly Val Pro Gly Ser Gly Val Pro Gly Ser Gly Val Pro Gly Ser
    210                 215                 220

Gly Val Pro Gly Ser Gly Val Pro Gly Ser Gly Val Pro Gly Ser Gly
225                 230                 235                 240

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any hydrophobic amino acid

<400> SEQUENCE: 23

Val Pro Gly Xaa Gly
1               5

<210> SEQ ID NO 24

```
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any hydrophobic amino acid
<220> FEATURE:
<221> NAME/KEY: MOD_RES
<222> LOCATION: (19)..(19)
<223> OTHER INFORMATION: Any hydrophobic amino acid
<220> FEATURE:
<221> NAME/KEY: MOD_RES
<222> LOCATION: (24)..(24)
<223> OTHER INFORMATION: Any hydrophobic amino acid
<220> FEATURE:
<221> NAME/KEY: MOD_RES
<222> LOCATION: (29)..(29)
<223> OTHER INFORMATION: Any hydrophobic amino acid
<220> FEATURE:
<221> NAME/KEY: MOD_RES
<222> LOCATION: (34)..(34)
<223> OTHER INFORMATION: Any hydrophobic amino acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: MOD_RES
<222> LOCATION: (44)..(44)
<223> OTHER INFORMATION: Any hydrophobic amino acid
<220> FEATURE:
<221> NAME/KEY: MOD_RES
<222> LOCATION: (49)..(49)
<223> OTHER INFORMATION: Any hydrophobic amino acid
<220> FEATURE:
<221> NAME/KEY: MOD_RES
<222> LOCATION: (54)..(54)
<223> OTHER INFORMATION: Any hydrophobic amino acid
<220> FEATURE:
<221> NAME/KEY: MOD_RES
<222> LOCATION: (59)..(59)
<223> OTHER INFORMATION: Any hydrophobic amino acid
<220> FEATURE:
<221> NAME/KEY: MOD_RES
<222> LOCATION: (64)..(64)
<223> OTHER INFORMATION: Any hydrophobic amino acid
<220> FEATURE:
<221> NAME/KEY: MOD_RES
<222> LOCATION: (69)..(69)
<223> OTHER INFORMATION: Any hydrophobic amino acid
<220> FEATURE:
<221> NAME/KEY: MOD_RES
<222> LOCATION: (74)..(74)
<223> OTHER INFORMATION: Any hydrophobic amino acid
<220> FEATURE:
<221> NAME/KEY: MOD_RES
<222> LOCATION: (79)..(79)
<223> OTHER INFORMATION: Any hydrophobic amino acid
<220> FEATURE:
<221> NAME/KEY: MOD_RES
<222> LOCATION: (84)..(84)
<223> OTHER INFORMATION: Any hydrophobic amino acid
<220> FEATURE:
<221> NAME/KEY: MOD_RES
<222> LOCATION: (89)..(89)
<223> OTHER INFORMATION: Any hydrophobic amino acid
<220> FEATURE:
```

```
<221> NAME/KEY: MOD_RES
<222> LOCATION: (94)..(94)
<223> OTHER INFORMATION: Any hydrophobic amino acid
<220> FEATURE:
<221> NAME/KEY: MOD_RES
<222> LOCATION: (99)..(99)
<223> OTHER INFORMATION: Any hydrophobic amino acid
<220> FEATURE:
<221> NAME/KEY: MOD_RES
<222> LOCATION: (104)..(104)
<223> OTHER INFORMATION: Any hydrophobic amino acid
<220> FEATURE:
<221> NAME/KEY: MOD_RES
<222> LOCATION: (109)..(109)
<223> OTHER INFORMATION: Any hydrophobic amino acid
<220> FEATURE:
<221> NAME/KEY: MOD_RES
<222> LOCATION: (114)..(114)
<223> OTHER INFORMATION: Any hydrophobic amino acid
<220> FEATURE:
<221> NAME/KEY: MOD_RES
<222> LOCATION: (119)..(119)
<223> OTHER INFORMATION: Any hydrophobic amino acid
<220> FEATURE:
<221> NAME/KEY: MOD_RES
<222> LOCATION: (124)..(124)
<223> OTHER INFORMATION: Any hydrophobic amino acid
<220> FEATURE:
<221> NAME/KEY: MOD_RES
<222> LOCATION: (129)..(129)
<223> OTHER INFORMATION: Any hydrophobic amino acid
<220> FEATURE:
<221> NAME/KEY: MOD_RES
<222> LOCATION: (134)..(134)
<223> OTHER INFORMATION: Any hydrophobic amino acid
<220> FEATURE:
<221> NAME/KEY: MOD_RES
<222> LOCATION: (139)..(139)
<223> OTHER INFORMATION: Any hydrophobic amino acid
<220> FEATURE:
<221> NAME/KEY: MOD_RES
<222> LOCATION: (144)..(144)
<223> OTHER INFORMATION: Any hydrophobic amino acid
<220> FEATURE:
<221> NAME/KEY: MOD_RES
<222> LOCATION: (149)..(149)
<223> OTHER INFORMATION: Any hydrophobic amino acid
<220> FEATURE:
<221> NAME/KEY: MOD_RES
<222> LOCATION: (154)..(154)
<223> OTHER INFORMATION: Any hydrophobic amino acid
<220> FEATURE:
<221> NAME/KEY: MOD_RES
<222> LOCATION: (159)..(159)
<223> OTHER INFORMATION: Any hydrophobic amino acid
<220> FEATURE:
<221> NAME/KEY: MOD_RES
<222> LOCATION: (164)..(164)
<223> OTHER INFORMATION: Any hydrophobic amino acid
<220> FEATURE:
<221> NAME/KEY: MOD_RES
<222> LOCATION: (169)..(169)
<223> OTHER INFORMATION: Any hydrophobic amino acid
<220> FEATURE:
<221> NAME/KEY: MOD_RES
<222> LOCATION: (174)..(174)
<223> OTHER INFORMATION: Any hydrophobic amino acid
<220> FEATURE:
<221> NAME/KEY: MOD_RES
<222> LOCATION: (179)..(179)
<223> OTHER INFORMATION: Any hydrophobic amino acid
<220> FEATURE:
<221> NAME/KEY: MOD_RES
<222> LOCATION: (184)..(184)
<223> OTHER INFORMATION: Any hydrophobic amino acid
<220> FEATURE:
<221> NAME/KEY: MOD_RES
<222> LOCATION: (189)..(189)
<223> OTHER INFORMATION: Any hydrophobic amino acid
```

-continued

```
<220> FEATURE:
<221> NAME/KEY: MOD_RES
<222> LOCATION: (194)..(194)
<223> OTHER INFORMATION: Any hydrophobic amino acid
<220> FEATURE:
<221> NAME/KEY: MOD_RES
<222> LOCATION: (199)..(199)
<223> OTHER INFORMATION: Any hydrophobic amino acid
<220> FEATURE:
<221> NAME/KEY: MOD_RES
<222> LOCATION: (204)..(204)
<223> OTHER INFORMATION: Any hydrophobic amino acid
<220> FEATURE:
<221> NAME/KEY: MOD_RES
<222> LOCATION: (209)..(209)
<223> OTHER INFORMATION: Any hydrophobic amino acid
<220> FEATURE:
<221> NAME/KEY: MOD_RES
<222> LOCATION: (214)..(214)
<223> OTHER INFORMATION: Any hydrophobic amino acid
<220> FEATURE:
<221> NAME/KEY: MOD_RES
<222> LOCATION: (219)..(219)
<223> OTHER INFORMATION: Any hydrophobic amino acid
<220> FEATURE:
<221> NAME/KEY: MOD_RES
<222> LOCATION: (224)..(224)
<223> OTHER INFORMATION: Any hydrophobic amino acid
<220> FEATURE:
<221> NAME/KEY: MOD_RES
<222> LOCATION: (229)..(229)
<223> OTHER INFORMATION: Any hydrophobic amino acid
<220> FEATURE:
<221> NAME/KEY: MOD_RES
<222> LOCATION: (234)..(234)
<223> OTHER INFORMATION: Any hydrophobic amino acid
<220> FEATURE:
<221> NAME/KEY: MOD_RES
<222> LOCATION: (239)..(239)
<223> OTHER INFORMATION: Any hydrophobic amino acid
<220> FEATURE:
<221> NAME/KEY: MOD_RES
<222> LOCATION: (244)..(244)
<223> OTHER INFORMATION: Any hydrophobic amino acid
<220> FEATURE:
<221> NAME/KEY: MOD_RES
<222> LOCATION: (249)..(249)
<223> OTHER INFORMATION: Any hydrophobic amino acid
<220> FEATURE:
<221> NAME/KEY: MOD_RES
<222> LOCATION: (254)..(254)
<223> OTHER INFORMATION: Any hydrophobic amino acid
<220> FEATURE:
<221> NAME/KEY: MOD_RES
<222> LOCATION: (259)..(259)
<223> OTHER INFORMATION: Any hydrophobic amino acid
<220> FEATURE:
<221> NAME/KEY: MOD_RES
<222> LOCATION: (264)..(264)
<223> OTHER INFORMATION: Any hydrophobic amino acid
<220> FEATURE:
<221> NAME/KEY: MOD_RES
<222> LOCATION: (269)..(269)
<223> OTHER INFORMATION: Any hydrophobic amino acid
<220> FEATURE:
<221> NAME/KEY: MOD_RES
<222> LOCATION: (274)..(274)
<223> OTHER INFORMATION: Any hydrophobic amino acid
<220> FEATURE:
<221> NAME/KEY: MOD_RES
<222> LOCATION: (279)..(279)
<223> OTHER INFORMATION: Any hydrophobic amino acid
<220> FEATURE:
<221> NAME/KEY: MOD_RES
<222> LOCATION: (284)..(284)
<223> OTHER INFORMATION: Any hydrophobic amino acid
<220> FEATURE:
<221> NAME/KEY: MOD_RES
<222> LOCATION: (289)..(289)
```

```
<223> OTHER INFORMATION: Any hydrophobic amino acid
<220> FEATURE:
<221> NAME/KEY: MOD_RES
<222> LOCATION: (294)..(294)
<223> OTHER INFORMATION: Any hydrophobic amino acid
<220> FEATURE:
<221> NAME/KEY: MOD_RES
<222> LOCATION: (299)..(299)
<223> OTHER INFORMATION: Any hydrophobic amino acid
<220> FEATURE:
<221> NAME/KEY: MOD_RES
<222> LOCATION: (304)..(304)
<223> OTHER INFORMATION: Any hydrophobic amino acid
<220> FEATURE:
<221> NAME/KEY: MOD_RES
<222> LOCATION: (309)..(309)
<223> OTHER INFORMATION: Any hydrophobic amino acid
<220> FEATURE:
<221> NAME/KEY: MOD_RES
<222> LOCATION: (314)..(314)
<223> OTHER INFORMATION: Any hydrophobic amino acid
<220> FEATURE:
<221> NAME/KEY: MOD_RES
<222> LOCATION: (319)..(319)
<223> OTHER INFORMATION: Any hydrophobic amino acid
<220> FEATURE:
<221> NAME/KEY: MOD_RES
<222> LOCATION: (324)..(324)
<223> OTHER INFORMATION: Any hydrophobic amino acid
<220> FEATURE:
<221> NAME/KEY: MOD_RES
<222> LOCATION: (329)..(329)
<223> OTHER INFORMATION: Any hydrophobic amino acid
<220> FEATURE:
<221> NAME/KEY: MOD_RES
<222> LOCATION: (334)..(334)
<223> OTHER INFORMATION: Any hydrophobic amino acid
<220> FEATURE:
<221> NAME/KEY: MOD_RES
<222> LOCATION: (339)..(339)
<223> OTHER INFORMATION: Any hydrophobic amino acid
<220> FEATURE:
<221> NAME/KEY: MOD_RES
<222> LOCATION: (344)..(344)
<223> OTHER INFORMATION: Any hydrophobic amino acid
<220> FEATURE:
<221> NAME/KEY: MOD_RES
<222> LOCATION: (349)..(349)
<223> OTHER INFORMATION: Any hydrophobic amino acid
<220> FEATURE:
<221> NAME/KEY: MOD_RES
<222> LOCATION: (354)..(354)
<223> OTHER INFORMATION: Any hydrophobic amino acid
<220> FEATURE:
<221> NAME/KEY: MOD_RES
<222> LOCATION: (359)..(359)
<223> OTHER INFORMATION: Any hydrophobic amino acid
<220> FEATURE:
<221> NAME/KEY: MOD_RES
<222> LOCATION: (364)..(364)
<223> OTHER INFORMATION: Any hydrophobic amino acid
<220> FEATURE:
<221> NAME/KEY: MOD_RES
<222> LOCATION: (369)..(369)
<223> OTHER INFORMATION: Any hydrophobic amino acid
<220> FEATURE:
<221> NAME/KEY: MOD_RES
<222> LOCATION: (374)..(374)
<223> OTHER INFORMATION: Any hydrophobic amino acid
<220> FEATURE:
<221> NAME/KEY: MOD_RES
<222> LOCATION: (379)..(379)
<223> OTHER INFORMATION: Any hydrophobic amino acid
<220> FEATURE:
<221> NAME/KEY: MOD_RES
<222> LOCATION: (384)..(384)
<223> OTHER INFORMATION: Any hydrophobic amino acid
<220> FEATURE:
<221> NAME/KEY: MOD_RES
```

```
<222> LOCATION: (389)..(389)
<223> OTHER INFORMATION: Any hydrophobic amino acid
<220> FEATURE:
<221> NAME/KEY: MOD_RES
<222> LOCATION: (394)..(394)
<223> OTHER INFORMATION: Any hydrophobic amino acid
<220> FEATURE:
<221> NAME/KEY: MOD_RES
<222> LOCATION: (399)..(399)
<223> OTHER INFORMATION: Any hydrophobic amino acid
<220> FEATURE:
<221> NAME/KEY: MOD_RES
<222> LOCATION: (404)..(404)
<223> OTHER INFORMATION: Any hydrophobic amino acid
<220> FEATURE:
<221> NAME/KEY: MOD_RES
<222> LOCATION: (409)..(409)
<223> OTHER INFORMATION: Any hydrophobic amino acid
<220> FEATURE:
<221> NAME/KEY: MOD_RES
<222> LOCATION: (414)..(414)
<223> OTHER INFORMATION: Any hydrophobic amino acid
<220> FEATURE:
<221> NAME/KEY: MOD_RES
<222> LOCATION: (419)..(419)
<223> OTHER INFORMATION: Any hydrophobic amino acid
<220> FEATURE:
<221> NAME/KEY: MOD_RES
<222> LOCATION: (424)..(424)
<223> OTHER INFORMATION: Any hydrophobic amino acid
<220> FEATURE:
<221> NAME/KEY: MOD_RES
<222> LOCATION: (429)..(429)
<223> OTHER INFORMATION: Any hydrophobic amino acid
<220> FEATURE:
<221> NAME/KEY: MOD_RES
<222> LOCATION: (434)..(434)
<223> OTHER INFORMATION: Any hydrophobic amino acid
<220> FEATURE:
<221> NAME/KEY: MOD_RES
<222> LOCATION: (439)..(439)
<223> OTHER INFORMATION: Any hydrophobic amino acid
<220> FEATURE:
<221> NAME/KEY: MOD_RES
<222> LOCATION: (444)..(444)
<223> OTHER INFORMATION: Any hydrophobic amino acid
<220> FEATURE:
<221> NAME/KEY: MOD_RES
<222> LOCATION: (449)..(449)
<223> OTHER INFORMATION: Any hydrophobic amino acid
<220> FEATURE:
<221> NAME/KEY: MISC_FEATURE
<222> LOCATION: (1)..(450)
<223> OTHER INFORMATION: This sequence may encompass 20-90 "Val-Pro-Gly-
      Xaa-Gly" repeating units

<400> SEQUENCE: 24

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110
```

Gly Xaa Gly Val Pro Gly Xaa Gly Val Pro Gly Xaa Gly Val Pro Gly
            115                 120                 125

Xaa Gly Val Pro Gly Xaa Gly Val Pro Gly Xaa Gly Val Pro Gly Xaa
        130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly
        355                 360                 365

Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
                405                 410                 415

Pro Gly Xaa Gly Val Pro Gly Xaa Gly Val Pro Gly Xaa Gly Val Pro
            420                 425                 430

Gly Xaa Gly Val Pro Gly Xaa Gly Val Pro Gly Xaa Gly Val Pro Gly
        435                 440                 445

Xaa Gly
    450

<210> SEQ ID NO 25
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any hydrophobic amino acid
<220> FEATURE:

```
<221> NAME/KEY: MOD_RES
<222> LOCATION: (9)..(9)
<223> OTHER INFORMATION: Any hydrophobic amino acid
<220> FEATURE:
<221> NAME/KEY: MOD_RES
<222> LOCATION: (14)..(14)
<223> OTHER INFORMATION: Any hydrophobic amino acid
<220> FEATURE:
<221> NAME/KEY: MOD_RES
<222> LOCATION: (19)..(19)
<223> OTHER INFORMATION: Any hydrophobic amino acid
<220> FEATURE:
<221> NAME/KEY: MOD_RES
<222> LOCATION: (24)..(24)
<223> OTHER INFORMATION: Any hydrophobic amino acid
<220> FEATURE:
<221> NAME/KEY: MOD_RES
<222> LOCATION: (29)..(29)
<223> OTHER INFORMATION: Any hydrophobic amino acid
<220> FEATURE:
<221> NAME/KEY: MOD_RES
<222> LOCATION: (34)..(34)
<223> OTHER INFORMATION: Any hydrophobic amino acid
<220> FEATURE:
<221> NAME/KEY: MOD_RES
<222> LOCATION: (39)..(39)
<223> OTHER INFORMATION: Any hydrophobic amino acid
<220> FEATURE:
<221> NAME/KEY: MOD_RES
<222> LOCATION: (44)..(44)
<223> OTHER INFORMATION: Any hydrophobic amino acid
<220> FEATURE:
<221> NAME/KEY: MOD_RES
<222> LOCATION: (49)..(49)
<223> OTHER INFORMATION: Any hydrophobic amino acid
<220> FEATURE:
<221> NAME/KEY: MOD_RES
<222> LOCATION: (54)..(54)
<223> OTHER INFORMATION: Any hydrophobic amino acid
<220> FEATURE:
<221> NAME/KEY: MOD_RES
<222> LOCATION: (59)..(59)
<223> OTHER INFORMATION: Any hydrophobic amino acid
<220> FEATURE:
<221> NAME/KEY: MOD_RES
<222> LOCATION: (64)..(64)
<223> OTHER INFORMATION: Any hydrophobic amino acid
<220> FEATURE:
<221> NAME/KEY: MOD_RES
<222> LOCATION: (69)..(69)
<223> OTHER INFORMATION: Any hydrophobic amino acid
<220> FEATURE:
<221> NAME/KEY: MOD_RES
<222> LOCATION: (74)..(74)
<223> OTHER INFORMATION: Any hydrophobic amino acid
<220> FEATURE:
<221> NAME/KEY: MOD_RES
<222> LOCATION: (79)..(79)
<223> OTHER INFORMATION: Any hydrophobic amino acid
<220> FEATURE:
<221> NAME/KEY: MOD_RES
<222> LOCATION: (84)..(84)
<223> OTHER INFORMATION: Any hydrophobic amino acid
<220> FEATURE:
<221> NAME/KEY: MOD_RES
<222> LOCATION: (89)..(89)
<223> OTHER INFORMATION: Any hydrophobic amino acid
<220> FEATURE:
<221> NAME/KEY: MOD_RES
<222> LOCATION: (94)..(94)
<223> OTHER INFORMATION: Any hydrophobic amino acid
<220> FEATURE:
<221> NAME/KEY: MOD_RES
<222> LOCATION: (99)..(99)
<223> OTHER INFORMATION: Any hydrophobic amino acid
<220> FEATURE:
<221> NAME/KEY: MOD_RES
<222> LOCATION: (104)..(104)
<223> OTHER INFORMATION: Any hydrophobic amino acid
```

-continued

```
<220> FEATURE:
<221> NAME/KEY: MOD_RES
<222> LOCATION: (109)..(109)
<223> OTHER INFORMATION: Any hydrophobic amino acid
<220> FEATURE:
<221> NAME/KEY: MOD_RES
<222> LOCATION: (114)..(114)
<223> OTHER INFORMATION: Any hydrophobic amino acid
<220> FEATURE:
<221> NAME/KEY: MOD_RES
<222> LOCATION: (119)..(119)
<223> OTHER INFORMATION: Any hydrophobic amino acid
<220> FEATURE:
<221> NAME/KEY: MOD_RES
<222> LOCATION: (124)..(124)
<223> OTHER INFORMATION: Any hydrophobic amino acid
<220> FEATURE:
<221> NAME/KEY: MOD_RES
<222> LOCATION: (129)..(129)
<223> OTHER INFORMATION: Any hydrophobic amino acid
<220> FEATURE:
<221> NAME/KEY: MOD_RES
<222> LOCATION: (134)..(134)
<223> OTHER INFORMATION: Any hydrophobic amino acid
<220> FEATURE:
<221> NAME/KEY: MOD_RES
<222> LOCATION: (139)..(139)
<223> OTHER INFORMATION: Any hydrophobic amino acid
<220> FEATURE:
<221> NAME/KEY: MOD_RES
<222> LOCATION: (144)..(144)
<223> OTHER INFORMATION: Any hydrophobic amino acid
<220> FEATURE:
<221> NAME/KEY: MOD_RES
<222> LOCATION: (149)..(149)
<223> OTHER INFORMATION: Any hydrophobic amino acid
<220> FEATURE:
<221> NAME/KEY: MOD_RES
<222> LOCATION: (154)..(154)
<223> OTHER INFORMATION: Any hydrophobic amino acid
<220> FEATURE:
<221> NAME/KEY: MOD_RES
<222> LOCATION: (159)..(159)
<223> OTHER INFORMATION: Any hydrophobic amino acid
<220> FEATURE:
<221> NAME/KEY: MOD_RES
<222> LOCATION: (164)..(164)
<223> OTHER INFORMATION: Any hydrophobic amino acid
<220> FEATURE:
<221> NAME/KEY: MOD_RES
<222> LOCATION: (169)..(169)
<223> OTHER INFORMATION: Any hydrophobic amino acid
<220> FEATURE:
<221> NAME/KEY: MOD_RES
<222> LOCATION: (174)..(174)
<223> OTHER INFORMATION: Any hydrophobic amino acid
<220> FEATURE:
<221> NAME/KEY: MOD_RES
<222> LOCATION: (179)..(179)
<223> OTHER INFORMATION: Any hydrophobic amino acid
<220> FEATURE:
<221> NAME/KEY: MOD_RES
<222> LOCATION: (184)..(184)
<223> OTHER INFORMATION: Any hydrophobic amino acid
<220> FEATURE:
<221> NAME/KEY: MOD_RES
<222> LOCATION: (189)..(189)
<223> OTHER INFORMATION: Any hydrophobic amino acid
<220> FEATURE:
<221> NAME/KEY: MOD_RES
<222> LOCATION: (194)..(194)
<223> OTHER INFORMATION: Any hydrophobic amino acid
<220> FEATURE:
<221> NAME/KEY: MOD_RES
<222> LOCATION: (199)..(199)
<223> OTHER INFORMATION: Any hydrophobic amino acid
<220> FEATURE:
<221> NAME/KEY: MOD_RES
<222> LOCATION: (204)..(204)
```

```
<223> OTHER INFORMATION: Any hydrophobic amino acid
<220> FEATURE:
<221> NAME/KEY: MOD_RES
<222> LOCATION: (209)..(209)
<223> OTHER INFORMATION: Any hydrophobic amino acid
<220> FEATURE:
<221> NAME/KEY: MOD_RES
<222> LOCATION: (214)..(214)
<223> OTHER INFORMATION: Any hydrophobic amino acid
<220> FEATURE:
<221> NAME/KEY: MOD_RES
<222> LOCATION: (219)..(219)
<223> OTHER INFORMATION: Any hydrophobic amino acid
<220> FEATURE:
<221> NAME/KEY: MOD_RES
<222> LOCATION: (224)..(224)
<223> OTHER INFORMATION: Any hydrophobic amino acid
<220> FEATURE:
<221> NAME/KEY: MOD_RES
<222> LOCATION: (229)..(229)
<223> OTHER INFORMATION: Any hydrophobic amino acid
<220> FEATURE:
<221> NAME/KEY: MOD_RES
<222> LOCATION: (234)..(234)
<223> OTHER INFORMATION: Any hydrophobic amino acid
<220> FEATURE:
<221> NAME/KEY: MOD_RES
<222> LOCATION: (239)..(239)
<223> OTHER INFORMATION: Any hydrophobic amino acid
<220> FEATURE:
<221> NAME/KEY: MOD_RES
<222> LOCATION: (244)..(244)
<223> OTHER INFORMATION: Any hydrophobic amino acid
<220> FEATURE:
<221> NAME/KEY: MOD_RES
<222> LOCATION: (249)..(249)
<223> OTHER INFORMATION: Any hydrophobic amino acid
<220> FEATURE:
<221> NAME/KEY: MOD_RES
<222> LOCATION: (254)..(254)
<223> OTHER INFORMATION: Any hydrophobic amino acid
<220> FEATURE:
<221> NAME/KEY: MOD_RES
<222> LOCATION: (259)..(259)
<223> OTHER INFORMATION: Any hydrophobic amino acid
<220> FEATURE:
<221> NAME/KEY: MOD_RES
<222> LOCATION: (264)..(264)
<223> OTHER INFORMATION: Any hydrophobic amino acid
<220> FEATURE:
<221> NAME/KEY: MOD_RES
<222> LOCATION: (269)..(269)
<223> OTHER INFORMATION: Any hydrophobic amino acid
<220> FEATURE:
<221> NAME/KEY: MOD_RES
<222> LOCATION: (274)..(274)
<223> OTHER INFORMATION: Any hydrophobic amino acid
<220> FEATURE:
<221> NAME/KEY: MOD_RES
<222> LOCATION: (279)..(279)
<223> OTHER INFORMATION: Any hydrophobic amino acid
<220> FEATURE:
<221> NAME/KEY: MOD_RES
<222> LOCATION: (284)..(284)
<223> OTHER INFORMATION: Any hydrophobic amino acid
<220> FEATURE:
<221> NAME/KEY: MOD_RES
<222> LOCATION: (289)..(289)
<223> OTHER INFORMATION: Any hydrophobic amino acid
<220> FEATURE:
<221> NAME/KEY: MOD_RES
<222> LOCATION: (294)..(294)
<223> OTHER INFORMATION: Any hydrophobic amino acid
<220> FEATURE:
<221> NAME/KEY: MOD_RES
<222> LOCATION: (299)..(299)
<223> OTHER INFORMATION: Any hydrophobic amino acid
<220> FEATURE:
<221> NAME/KEY: MOD_RES
```

```
<222> LOCATION: (304)..(304)
<223> OTHER INFORMATION: Any hydrophobic amino acid
<220> FEATURE:
<221> NAME/KEY: MOD_RES
<222> LOCATION: (309)..(309)
<223> OTHER INFORMATION: Any hydrophobic amino acid
<220> FEATURE:
<221> NAME/KEY: MOD_RES
<222> LOCATION: (314)..(314)
<223> OTHER INFORMATION: Any hydrophobic amino acid
<220> FEATURE:
<221> NAME/KEY: MOD_RES
<222> LOCATION: (319)..(319)
<223> OTHER INFORMATION: Any hydrophobic amino acid
<220> FEATURE:
<221> NAME/KEY: MOD_RES
<222> LOCATION: (324)..(324)
<223> OTHER INFORMATION: Any hydrophobic amino acid
<220> FEATURE:
<221> NAME/KEY: MOD_RES
<222> LOCATION: (329)..(329)
<223> OTHER INFORMATION: Any hydrophobic amino acid
<220> FEATURE:
<221> NAME/KEY: MOD_RES
<222> LOCATION: (334)..(334)
<223> OTHER INFORMATION: Any hydrophobic amino acid
<220> FEATURE:
<221> NAME/KEY: MOD_RES
<222> LOCATION: (339)..(339)
<223> OTHER INFORMATION: Any hydrophobic amino acid
<220> FEATURE:
<221> NAME/KEY: MOD_RES
<222> LOCATION: (344)..(344)
<223> OTHER INFORMATION: Any hydrophobic amino acid
<220> FEATURE:
<221> NAME/KEY: MOD_RES
<222> LOCATION: (349)..(349)
<223> OTHER INFORMATION: Any hydrophobic amino acid
<220> FEATURE:
<221> NAME/KEY: MOD_RES
<222> LOCATION: (354)..(354)
<223> OTHER INFORMATION: Any hydrophobic amino acid
<220> FEATURE:
<221> NAME/KEY: MOD_RES
<222> LOCATION: (359)..(359)
<223> OTHER INFORMATION: Any hydrophobic amino acid
<220> FEATURE:
<221> NAME/KEY: MOD_RES
<222> LOCATION: (364)..(364)
<223> OTHER INFORMATION: Any hydrophobic amino acid
<220> FEATURE:
<221> NAME/KEY: MOD_RES
<222> LOCATION: (369)..(369)
<223> OTHER INFORMATION: Any hydrophobic amino acid
<220> FEATURE:
<221> NAME/KEY: MOD_RES
<222> LOCATION: (374)..(374)
<223> OTHER INFORMATION: Any hydrophobic amino acid
<220> FEATURE:
<221> NAME/KEY: MOD_RES
<222> LOCATION: (379)..(379)
<223> OTHER INFORMATION: Any hydrophobic amino acid
<220> FEATURE:
<221> NAME/KEY: MOD_RES
<222> LOCATION: (384)..(384)
<223> OTHER INFORMATION: Any hydrophobic amino acid
<220> FEATURE:
<221> NAME/KEY: MOD_RES
<222> LOCATION: (389)..(389)
<223> OTHER INFORMATION: Any hydrophobic amino acid
<220> FEATURE:
<221> NAME/KEY: MOD_RES
<222> LOCATION: (394)..(394)
<223> OTHER INFORMATION: Any hydrophobic amino acid
<220> FEATURE:
<221> NAME/KEY: MOD_RES
<222> LOCATION: (399)..(399)
<223> OTHER INFORMATION: Any hydrophobic amino acid
<220> FEATURE:
```

<221> NAME/KEY: MISC_FEATURE
<222> LOCATION: (1)..(400)
<223> OTHER INFORMATION: This sequence may encompass 20-80 "Val-Pro-Gly-
      Xaa-Gly" repeating units

<400> SEQUENCE: 25

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly
        355                 360                 365

```
Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400
```

GENERATION OF HEMOGLOBIN-BASED OXYGEN CARRIERS USING ELASTIN-LIKE POLYPEPTIDES

CROSS REFERENCE TO RELATED APPLICATIONS

This application is a continuation of U.S. application Ser. No. 14/965,053, filed Dec. 10, 2015, which claims the benefit of priority to U.S. Provisional Application No. 62/089,885, filed Dec. 10, 2014, entitled "GENERATION OF HEMOGLOBIN-BASED OXYGEN CARRIERS USING ELASTIN-LIKE POLYPEPTIDES", the content of which is incorporated by reference in their entirety.

The instant application contains a Sequence Listing which has been submitted electronically in ASCII format and is hereby incorporated by reference in its entirety. Said ASCII copy, created on Oct. 25, 2019, is named 064189-6748_SL.txt and is 121,379 bytes in size.

FIELD OF INVENTION

The present invention relates generally to artificial or synthetic blood substitutes.

BACKGROUND OF THE INVENTION

The Circulatory System and the Nature of Hemoglobin

Blood, the means for delivering oxygen ($O_2$) and nutrients to the tissues and removing carbon dioxide ($CO_2$) and waste products from the tissues for excretion, is composed of plasma in which red blood cells (RBCs or erythrocytes), white blood cells (WBCs), and platelets are suspended. The functions of blood can be grouped generally as maintenance of intravascular volume, delivery of oxygen to tissues, provision of coagulation factors, provision of some defense mechanisms, and transportation of metabolic waste products.

When the heart contracts, blood is pumped into certain major blood vessels, and from there, continues through the circulatory system. Humans and other mammals have two-circuit circulatory systems: one circuit is for pulmonary circulation (circulation to the lungs), and the other circuit is for systemic circulation (the rest of the body). Blood that is lacking oxygen is said to be deoxygenated. Deoxygenated blood, which has just exchanged oxygen for carbon dioxide across cell membranes, and now contains mostly carbon dioxide, enters the right atrium, where pulmonary circulation begins, and flows into the right ventricle. As the right ventricle contracts, it forces the deoxygenated blood into the pulmonary artery, which carries the deoxygenated blood to the lungs, where it becomes oxygenated.

Freshly oxygenated blood returns to the heart via the pulmonary veins, into the left atrium, which is where systemic circulation begins. The freshly oxygenated blood flows from the left atrium into the left ventricle. As the left ventricle contracts, the oxygenated blood is pumped into the main artery of the body—(the aorta), which branches into other arteries, which then branch into smaller arterioles. The arterioles meet up with capillaries, which bridge the smallest of the arteries (arterioles) and the smallest of the veins (venules). Near the arterial end, the capillaries allow materials essential for maintaining the health of cells to diffuse out (water, glucose, oxygen, and amino acids) and transport wastes and carbon dioxide to places in the body that can dispose of them. The waste products enter near the venous end of the capillary. Water diffuses in and out of capillaries to maintain blood volume, which adjusts to achieve homeostasis. Thereafter, the deoxygenated blood travels through the venules and veins in its return to the right atrium of the heart, which is where pulmonary circulation begins.

Red blood cells comprise approximately 99% of the cells in blood, and their principal function is the transport of oxygen to and the removal of carbon dioxide from the tissues. About 95% of the dry weight of the red cell is hemoglobin. Hemoglobin functions primarily as a carrier of a large volume of oxygen taken up in the lungs and delivered to the tissues.

The reversible oxygenation function of RBCs (i.e. a large volume of oxygen taken up in the lungs and delivered to the tissues and the removal of carbon dioxide) is carried out by hemoglobin. Hemoglobin is composed of about 6% heme and 94% globin (protein).

Human adult hemoglobin is a tetrameric protein comprising two alpha ($\alpha_1$, $\alpha_2$) and two beta ($\beta_1$, $\beta_2$) polypeptide subunits, each of which consists of a polypeptide chain, globin, and an associated heme molecule. Heme is the name given to the molecule of iron and the particular porphyrin found in hemoglobin, for example, protoporphyrin IX. The alpha subunit consists of 141 amino acids. The iron atom of the heme (ferroprotoporphyrin IX) group is bound covalently to the imidazole of His 87 (the "proximal histidine") of the alpha subunit. The beta subunit is 146 residues long, and the heme group is bound to this subunit at His 92. Hemoglobin forms a loose complex with oxygen when the iron is in the ferrous ($Fe^{++}$) state. The four polypeptide subunits ($\alpha_1$, $\alpha_2$, $\beta_1$, $\beta_2$) are held together by noncovalent attractions, for example, salt bridge, hydrogen bonds, and hydrophobic effect.

The primary amino acid structure of the human adult hemoglobin alpha and beta subunits, and the nucleic acid sequences, which encode them, are known (see Wilson et al., J. Biol. Chem., 1980, 255(7), 2807-2815)

The transport of oxygen from the body's external environment to its peripheral tissues depends on several factors, including the concentration and partial pressure of oxygen in the inspired air, alveolar ventilation, ventilation-perfusion relationships, cardiac output, blood volume, and hemoglobin concentration. FIG. 1 shows an oxygen dissociation curve, which is a plot of the proportion of hemoglobin in its saturated form on the vertical axis against the prevailing oxygen tension on the horizontal axis. The position of the oxygen-hemoglobin dissociation curve describes the affinity of hemoglobin for oxygen, and influences the transfer of oxygen from hemoglobin in blood to tissue cells.

The oxygenated hemoglobin dissociation curve as shown in FIG. 1 has a characteristic sigmoid shape, which is typical of allosteric proteins due to the cooperative effect that exists between the multiple oxygen binding sites on the same hemoglobin molecule. When oxygen binds to the first subunit of deoxyhemoglobin, the first oxygen molecule increases the affinity of the remaining subunits for additional oxygen molecules. As additional oxygen is bound to the other hemoglobin subunits, oxygen binding is incrementally strengthened, so that hemoglobin is fully oxygen-saturated at the oxygen tension of lung alveoli. Likewise, oxygen is incrementally unloaded and the affinity of hemoglobin for oxygen is reduced as oxyhemoglobin circulates to deoxygenated tissue.

The value of percent (%) saturation can range from 0 (all sites empty) to 100% (all sites filled). Oxygen affinity can be characterized by a quantity P50, which is normal human adult partial pressure of oxygen at which 50% of sites are filled or at which 50% of the hemoglobin is oxygenated. For hemoglobin, P50 is 26 torrs. The oxygen dissociation curve reflects the interaction between oxygen and hemoglobin, and both the shape and position of the curve are subject to change by factors that modify the ability of hemoglobin to bind oxygen, including body temperature, pH of blood, $CO_2$ tension, and the concentration of 2,3-diphosphoglycerate (2,3-DPG). Alterations in hemoglobin-oxygen affinity also occur in many disease states. Table 1 summarizes factors that alter hemoglobin-oxygen affinity.

TABLE 1

Factors that increase or decrease P50.

| Increase P50 | Decrease P50 |
|---|---|
| By Direct Effect: | By Direct Effect: |
| Increased [H+] | Decreased [H+] |
| Temperature | Temperature |
| $PCO_2$ | $PCO_2$ |
| DPG, ATP | DPG, ATP |
| Hgb Conc. | Hgb Conc. |
| Ionic Strength | Ionic Strength |
| Abnormal Hemoglobin | Abnormal Hemoglobin |
| Aldosterone | Carboxy hemoglobin |
| | Methemoglobin |

(Adapted from: Shappell, S.D. et al.: Adaptive, Genetic and Iatrogenic Alterations of the Oxyhemoglobin dissociation Curve. *Anesthesiology*, 37: 127-139, 1971)

The affinity of hemoglobin for oxygen depends on pH. The $CO_2$ molecule also affects the oxygen-binding characteristics of hemoglobin. Both H+ and $CO_2$ promote the release of bound $O_2$. Reciprocally, $O_2$ promotes the release of bound H+ and $CO_2$.

The affinity of hemoglobin for oxygen is further regulated by organic phosphates, such as 2,3-bisphosphoglycerate (BPG). This highly anionic organic phosphate is present in human red cells at about the same molar concentration as hemoglobin. In the absence of BPG, the P50 of hemoglobin is 1 torr. In its presence, P50 becomes 26 torrs. BPG lowers the oxygen affinity of hemoglobin by a factor of 26, which is essential in enabling hemoglobin to unload oxygen in tissue capillaries, by binding to and cross-linking deoxyhemoglobin but not to the oxygenated form. (Stryer, L, Portrait of an Allosteric Protein, Biochemistry, 4th ed.) Certain diseases or age also affects affinity of hemoglobin for oxygen.

When hemoglobin's affinity for oxygen is increased, the RBCs have subnormal P50 values and their oxyhemoglobin dissociation curves are situated to the left of normal. These changes indicate that a lower than normal oxygen tension will be needed to saturate the RBC hemoglobin in the lung, and the release of oxygen in the tissue occurs at lower than normal capillary oxygen tension. When hemoglobin's affinity for oxygen is decreased, the P50 values are higher and the oxyhemoglobin dissociation curves are situated to the right of normal. These changes indicate that a higher than normal oxygen tension will be needed to saturate hemoglobin in the lung, and that the release of oxygen in the tissue occurs at higher than normal capillary oxygen tension.

Within limits, rightward or leftward shifts of the oxygen dissociation curves have little effect on arterial oxygen saturation since normal human adult arterial $PO_2$ is above 80 mm Hg. At the peripheral capillary level, however, even small shifts of the oxygen dissociation curve can be important. A rightward shift of the curve indicates decreased hemoglobin affinity for oxygen, while a leftward shift indicates an increase in hemoglobin-oxygen affinity. A rightward shift of the curve is advantageous theoretically, since an equivalent amount of oxygen is released at a higher $PO_2$ than with a leftward positioned curve.

Blood Transfusions

Over 4.5 million patients require blood transfusions throughout North America each year. Blood transfusions are a life-saving intervention for a number of clinical conditions including, without limitation, replacing blood lost during surgical procedures and following acute hemorrhage, for resuscitation procedures following traumatic injury, or for anemic patients. In events involving acute trauma, occurring in a serious car accident, for instance, a victim may need almost 100 pints of transfused blood. Transfusion therapy has been an integral part of military medicine. As the most needed and vital component of blood, red blood cells (RBCs) are the most transfused blood product in battlefield trauma care and more than 54,000 units of RBCs are transfused every year in military hospitals. The primary goal of blood transfusion is to restore the circulation of oxygen through the body, a function that is physiologically mediated by the hemoglobin found in red blood cells. It is reported that over 40% of all trauma-related deaths within the first 24 hours results from hemorrhagic shock, which can be rapidly fatal; serious car accidents, battlefield injuries, and complications during child delivery are other examples of incidents leading to hemorrhagic shock. The overwhelming cause of mortality in each of these cases is a loss of oxygen-carrying blood. In such cases, the transportation time from the site of injury to a healthcare facility represents a critical time for the patient. However, blood transfusion is not readily done before reaching a hospital facility due to disadvantages and constraints of blood transfusion that are discussed below.

Transfusion of a patient with donated blood, while used widely, has a number of disadvantages. First, due to the irregular nature of blood donations, blood supply shortages are common. Second, there may be a shortage of a patient's blood type. Third, transfused blood may be contaminated with infectious agents. Fourth, donated blood has a short stored shelf life (42 days) and must be stored in a refrigerated environment. Stored blood also loses 2,3-diphosphoglycerate (2,3-DPG) as time progresses, increasing its oxygen affinity and impairing oxygen unloading capacity in tissues. Fifth, complications can occur with blood transfusion due to inaccurate cross-matching, which remains the leading direct cause of death resulting from blood transfusion. Sixth, the greatest risk of transfusion may be the alterations it induces in recipients' immunological function. Multiple blood transfusions may eventually lead to a severe systemic inflammatory response, which may cause increasing incidence of multiple organ failure.

Because of the many disadvantages and constraints of blood transfusion and shortages of blood supply, the need to develop a viable blood substitute as an alternative to transfused blood has been long recognized.

Blood Substitutes

Blood substitutes are the "Holy Grail" of trauma medicine that researchers have pursued for more than a century. The ideal blood substitute would have none of the transfusion problems associated with blood, i.e., it would not require cross-matching or blood typing, could be stored preferably at room temperature for a long period, would have a reasonable intravascular life span and thereafter be excreted promptly, and would be free of toxicity or disease transmission. It might be used for immediate restoration of oxygen delivery, such as in trauma, or in other urgent situations involving massive blood loss where red blood cells are not available quickly. Since blood typing and cross-matching would not be necessary, the substitute might be carried in emergency vehicles, stocked in emergency departments, or used by the military or civilians in situations where access to blood is limited. Other potential uses of blood substitutes include organ perfusion and preservation prior to transplantation, and improving oxygen delivery to tissues that have an impaired blood supply. Unfortunately, to date, no oxygen-carrying blood substitutes are approved for use by the US Food and Drug Administration (FDA).

Blood substitutes that have been developed previously can be grouped into two categories: perfluorocarbon-based emulsions and cell-free hemoglobin-based blood substitutes. Perfluorochemical-based compositions dissolve oxygen as opposed to binding it as a chelate as hemoglobin does. They are chemically inert molecules containing, primarily, fluorine and carbon atoms and are capable of dissolving large amounts of many gases, including oxygen. However, most of the oxygen is released prior to reaching the oxygen-laden molecule in the capillary network where the need for oxygen is greater. These molecules are hydrophobic in nature, and hence have to be emulsified prior to intravenous administration. Most of the development of these agents have been halted or products been withdrawn from the market.

Products comprising modified cell-free hemoglobin, which are thought to be more promising, are frequently referred to as hemoglobin-based oxygen carriers. Hemoglobin can be prepared in solution by lysis of red cells. The RBC membrane contains proteins, cholesterol and phospholipids. Stroma-free hemoglobin or acellular hemoglobin has been investigated as an oxygen carrier since the 1940s, when researchers realized that native hemoglobin is not antigenic. A solution containing stroma-free hemoglobin has many advantages over intact red blood cells, including the ability to withstand sterilization and a shelf life of approximately 2 years at room temperature for some products. However, stroma-free hemoglobin has many shortcomings. First, it is not as effective at oxygenation as are red blood cells, because free hemoglobin has reduced contact with phosphates, causing the P50 curve to shift to the left, resulting in hemoglobin with a high oxygen affinity and limited unloading. Second, when infused rapidly, stroma-free hemoglobin splits into dimers and is cleared by glomerular filtration and uptake by the reticuloendothelial system. Third, clinically, stroma-free hemoglobin has been found to produce renal dysfunction, coagulopathy, and hypertension.

To address these limitations, a variety of approaches have been used to molecularly stabilize and chemically modify hemoglobin. Bunn cross-linked hemoglobin with bis (N-maleimidomethyl) ether (BME), reduced the hemoglobin molecule's tendency to form dimers, thus decreasing its renal filtration and clearance, and prolonged its intravascular retention (Bunn, J Exp Med. May 1, 1969; 129(5): 909-924). Other investigators have produced hemoglobin that had been chemically modified at the 2,3-DPG site, the amino terminal group, or internally in an attempt to prevent hemoglobin from disassociating into αβ dimers and as a means of restoring the P50 to near-normal levels. (Winslow R M, Hemoglobin modification. In: Winslow R M, editor. Blood Substitutes. London: Academic Press; 2006. pp. 341-53). Using a different approach, Bonsen et al. produced a hemoglobin that was polymerized with glutaraldehyde, which prolonged its intravascular retention (Bonsen P, Novel polymerized, cross-linked, stroma-free hemoglobin. United States: 1975). Another modification approach involved the attachment of hemoglobin to a larger molecule, which caused it to stay within the vascular system for a longer period of time than does non-modified hemogobin. In one study, hemoglobin coupled to dextran was shown to support life in dogs and cats in the absence of red blood cells. (Tam S C, Proc Natl Acad Sci USA. 1976 June; 73(6):2128-3114; Humphries R G, Br J Pharmacol. 1980; 74:266).

Out of these and other suggested chemically modified hemoglobins, several products progressed to human studies and limited testing in human patients. However, only a few advanced to Phase II and III trials: DCLHb/HemAssist® (Baxter), SFH-P/PolyHeme® (Northfield), and HBOC-201/Hemopure® (Biopure). (Chen, JY, et al., Clinics 2009, 64(8):803-13); and Grethlein, 2012.

Diaspirin Cross-Linked Hemoglobin (DCLHb/HemAssist)® consists of hemoglobin with cross-linking between the two alpha chains, which lends stability to the molecule. The source of hemoglobin consisting of outdated human red blood cells that were pooled, washed, lysed and filtered. The product is then deoxygenated, crosslinked with bis(3,5-dibromosalicyl)fumarate (DBBF), and reoxygenated. DCLHb solutions exhibits a P50 of 32 mmHg. It also exhibits a long shelf life when stored in a freezer. However, Baxter Healthcare halted further development of DCLHb in 1998 after the product failed trials in patients with stroke and trauma. (Winslow R M. Current status of oxygen carriers ('blood substitutes'): 2006. Vox Sang. August 2006; 91(2): 102-10.)

SFH-P/PolyHeme® (Northfield Laboratories Inc., Evanston, Ill.) is produced by crosslinking stroma-free hemoglobin from outdated RBCs with glutaraldehyde and then pyridoxylating it. The product has a P50 of 20-22 mmHg (compared to a normal RBC, which exhibits a P50 of 26 mmHg). In May 2009, the FDA refused to approve PolyHeme.

HBOC-201/Hemopure® is derived from bovine hemoglobin polymerized with glutaraldehyde. HBOC-201's P50 is 40 mmHg, resulting in a lower oxygen affinity than native hemoglobin. It has an intravascular half-life of 8-23 hours and a shelf life of 36 months at room temperature. Hemopure® is approved in South Africa for the treatment of adult surgical patients who are acutely anemic with the intention of eliminating or reducing the need for allogenic red blood cell transfusions. In the United States, phase II trials have been put on hold due to safety issues. Hemopure® was removed from the market in 2008 due to deaths related to kidney failure following transfusion of the product.

Other first-generation polymerized hemoglobin products include HemoLink® (Hemosol Corporation, Mississauga, Canada), a human hemoglobin based oxygen carrier, containing polymerized human Hb, cross-linked with o-raffinose.

Hemospan® (Sangart Inc., San Diego, Calif.), also known as MP4OX, is an acellular PEG-conjugated human hemoglobin therapeutic in clinical trials in Europe and the United States. The product is prepared by site-specific conjugation of maleimide-activated poly(ethylene) glycol (PEG, MW ~5500) to human oxyhemoglobin through maleimidation reactions either (1) directly to reactive Cys thiols or (2) at surface Lys groups following thiolation using 2-iminothiolane. The thiolation/maleimidation reactions lead to the addition of ~8 PEGs per hemoglobin tetramer. (Kim D. Vandegriff, Bioconjugate Chem., 2008, 19 (11), pp 2163-2170) In animal models, Hemospan (MP4OX) has been shown to be effective in cases of hemorrhagic shock.

Pyridoxylated hemoglobin polyoxyethylene conjugate (PHP) is a conjugated hemoglobin developed by Apex Bioscience that completed a phase III trial in August 2009 in patients with shock associated with systemic inflammatory response syndrome (SIRS) to evaluate the safety and efficacy of continuous IV infusion of PHP plus conventional vasopressor treatment versus continuous IV infusion of Plasma-lyte A plus conventional vasopressors as a treatment for restoring hemodynamic stability in patients.

A recombinant 130 kDa dihemoglobin, which is made up of a single-chain tetra-α globin and four β globins has been expressed as a soluble protein in *E. coli*. (Marquardt, et al., J. Funct. Biomater. 2012, 3(1), 61-78). A 260 kDa tetrahemoglobin has also been produced by chemical crosslinking of a dihemoglobin that contains a Lys16Cys mutation in the C-terminal α-globin subunit. Tetrahemoglobin also shows reduced vasoactivity in conscious rats that is comparable to that observed for dihemoglobin. (Marquardt, et al., J. Funct. Biomater. 2012, 3(1), 61-78)

Efforts have been made to encapsulate hemoglobin within a lipid-membrane (e.g. liposome) to create a compound capable of carrying oxygen while not being associated with significant vasoconstriction. However, the half-life of this liposome encapsulated hemoglobin is short, which has hindered its clinical development. Liposome encapsulated hemoglobin is prone to aggregate and fuse together after several days of storage, diminishing its functionality. At present, the only institutions working actively on this product are in Japan.

Biodegradable polymers are often considered as alternatives to lipids for their improved in vivo stability. A vast array of biodegradable polymers, ranging from synthetic to natural and to hybrid or recombinant, have been studied and developed for drug delivery. Depending on the choice of building blocks, block polymers can assemble to nanostructures in the form of micelles, electrostatic complexes, or polymersomes. (Hoffman A S, J. of controlled release: official journal of the controlled release society, 2008, 132: 153-163).

Synthetic polymers include degradable or non-degradable synthetic polymers. Exemplary synthetic degradable polymers include poly(c-caprolactone) (PCL), poly(ε-caprolactone-co-ethyl ethylene phosphate) (PCLEEP), poly(lactic acid) (PLA), poly(lactic-co-glycolic acid) (PLGA), poly (lactic acid-co-ε-caprolactone) (PLACL), and polydioxanone (PDO). Exemplary non-degradable polymers include poly acrylamide (PAAm), poly acrylic acid (PAA), poly acrylonitrile (PAN), poly amide (Nylon) (PA, PA-4,6, PA-6,6), poly aniline (PANI), poly benzimidazole (PBI), poly bis(2,2,2-trifluoroethoxy) phosphazene, poly butadiene (PB), poly carbonate (PC), poly ether amide (PEA), poly ether imide (PEI), poly ether sulfone (PES), poly ethylene (PE), poly ethylene-co-vinyl acetate (PEVA), poly ethylene glycol (PEG), poly ethylene oxide (PEO), poly ethylene terephthalate (PET), poly ferrocenyldimethylsilane (PFDMS), poly 2-hydroxyethyl methacrylate (HEMA), poly 4-methyl-1-pentene (TpX), poly methyl methacrylate (pMMA), poly p-phenylene terephthalamide (PPTA), poly propylene (PP), poly pyrrole (PPY), poly styrene (PS), polybisphenol-A sulfone (PSF), poly sulfonated styrene (PSS), Styrene-butadiene-styrene triblock copolymer (SBS), poly urethane (PU), poly tetrafluoro ethylene (PTFE), poly vinyl alcohol (PVA), poly vinyl carbazole, poly vinyl chloride (PVC), poly vinyl phenol (PVP), poly vinyl pyrrolidone (PVP), and poly vinylidene difluoride (PVDF). A preferred synthetic polymer is polyethersulfone (PES).

Natural polymers are biocompatible and biodegradable and are derived from biological systems including protein polymers, DNA, and polysaccharides. They possess low toxicity and potentially favorable pharmacokinetics in the circulation.

Protein polymers can be synthetic or natural, or recombinant.

Recombinant protein polymers comprise repetitive amino acid sequences that can spontaneously self-assemble into sub-100 nm size nanoparticles upon conjugation of diverse hydrophobic molecules. Recombinant protein polymers or genetically engineered protein polymers are biodegradable and potentially biocompatible if the artificial sequence is not antigenic. Genetic engineering allows precise control over structural and functional properties of recombinant proteins, such as their molecular weight, solubility, hydrophobicity, targeting motif, secondary structures, and drug conjugation sites. Two potential recombinant protein systems are elastin-like polypeptides (ELPs), and silk-elastin-like polypeptides (SELPs).

ELPs, a family of recombinant proteins derived from human tropoelastin, are one class of artificial repetitive polypeptides which have grown in popularity as an alternative to synthetic polymers. The basic building block is a short hydrophobic domain, comprised of a five amino acid motif (Val-Pro-Gly-Xaa-Gly)n (SEQ ID NO: 11). By substituting the fourth amino acid Xaa in the pentapeptide, ELPs can undergo reversible and rapid phase transition in response to temperature. ELPs undergo an inverse phase transition above a transition temperature (Tt), which is primarily a function of the guest residue Xaa, n, and concentration (Urry DW. Journal of Physical Chemistry B. 1997, 101:11007-11028; Chilkoti A. Biomacromolecules. 2004, 5:846-851). In solution, ELPs are structurally disordered. When the temperature is raised above their Tt, they undergo a sharp (2-3° C. range) phase transition, leading to biopolymer coacervation (Urry DW. Journal of Physical Chemistry B. 1997, 101:11007-11028). This process is fully reversible when the temperature is lowered below Tt. Phase separation can be triggered by other external stimuli such as changes in ionic strength, pH, solvent, and magnetic fields (Chilkoti A, Advanced Drug Delivery Reviews. 2002, 54:1093-1111; Mackay JA, Biomacromolecules. 2010, 11 (11):2873-2879).

A series of ELPs with distinct transition temperatures have been designed as drug carriers (MacKay J A, Nat Mater, 2009, 8:993-999). For example, in one system, ELP-peptide fusion protein was conjugated to doxorubicin (Dreher M R, Cancer Res. 2007, 67:4418-4424), which formed micelles and aggregated in the tumor microenvironment under hyperthermic conditions leading to increased accumulation at the tumor site. In another study, the effect of hyperthermia-induced micelle formation was exploited to present multivalent targeting motifs to enhance cellular uptake (Dreher M R, J. Am Chem Soc. 2008, 130:587-694). Multiblock ELPs have been developed for drug delivery in the form of nanoparticles (NP) or a hydrogel depending on the multiblock composition and processing method (Sallach R E, Biomaterials 2009, 30:409-422; Kim W, Adv Drug Deliv Rev. 2010, 62:1468-1478; Jordan S W, Biomaterials 2007, 28:1191-1197; Wu X, Biomacromolecules 2008, 9:1787-1794).

Based on prior studies in small animal models, ELPs have low immunogenicity (Megeed Z, et al. Adv Drug Delivery Rev. 2002, 54:1075-1091; Cappello J, et al. J Cont Rel. 1998; 53:105-117; Liu W, et al. J Control Release. 2006; 116:170-178).

Because ELPs can be produced via genetic engineering, their composition, MW, and polydispersity can be precisely controlled. ELPs can be reproduced with high yield (~100-200 mg/L) in *E. coli*, and can be rapidly purified by exploiting their phase transition behavior, so that high-purity, clinical grade material is obtained.

FIG. 2 is a transmission electron microscopy (TEM) of negatively stained with uranylacetate ELP micelle nanoparticles formed by repetitive amino-acid sequences with different guest residues in hydrophobic and hydrophilic blocks (white round objects) with an average particle diameter of about 33 nm. (S. M. Janib et al., Integr Biol, 2013, 5(1): 183-194).

As a peptide therapeutic, ELP biopolymers have reasonably good pharmacokinetics with terminal circulation half-lives of 8-11 h in nude mice (Liu W, J Control Release. 2006; 116:170-178). A 59 kD ELP nanoparticle [V5A2G3-150] with a transition temperature >37° C. evaluated in mice (as shown in FIG. 3), exhibited an elimination half-life of 6-8 hrs in mouse serum (MacKay, J A, Int J Hyperthermia, 2008, 24(6):483).

FIG. 4 shows uptake and degradation of ELP nanoparticles in transformed hepatocytes. This in vitro study demonstrated that mice hepatocytes enzymatically degrade ELP nanoparticles (M. Shah et al. Protein Sci, 2012, 21(6): 743-750).

Drugs conjugated with ELPs gain properties of thermally-induced phase transition and also maintain their in vitro bioactivity. This has been shown for chemically-conjugated chemotherapeutics such as doxorubicin (Dreher M R, J Control Release. 2003; 91(1-2):31-43), recombinant oligopeptide fusions with cell penetrating peptides (Massodi I, J Control Release. 2005; 108(2-3):396-408), a c-myc oncogene inhibitor, (Bidwell G L, Mol Cancer Ther. 2005; 4(7):1076-1085) and recombinant protein fusions with interleukin-1 receptor antagonist (Shamji M F, Arthritis Rheum. 2007; 56(11):3650-3661) and other proteins (Trabbic-Carlson K, Protein Sci. 2004; 13(12):3274-3284; Trabbic-Carlson K, Protein Eng Des Sel. 2004; 17(1):57-66). Surfaces coated with an ELP fused to the RGD or fibronectin CS5 cell binding sequence also retain an ability to support in vitro endothelial cell adhesion and spreading. (Liu J C, Biomacromolecules. 2004; 5(2):497-504). Other applications of ELPs, including entrapment of small molecules such as dexamethasone, (Herrero-Vanrell R, J Control Release. 2005; 102(1):113-122) have also been investigated. (Simnick A J, Polymer Reviews. 2007; 47:121-154).

ELPs are attractive as hemoglobin delivery systems for at least five important reasons: first, because ELPs can be genetically encoded, their synthesis from a synthetic gene in a heterologous host (e.g., bacteria or eukaryotic cell) can provide complete control over the amino acid sequence and molecular weight, two variables that are not easy to precisely control in synthetic polymers. Second, ELPs can be expressed from a plasmid-borne gene in E. coli to relatively high yields (~500 mg/L growth), which also makes them attractive for hemoglobin delivery applications where large quantities of polymer are often required. Third, they can be purified from E. coli—and other—cell lysates in batch process by exploiting their inverse temperature phase transition without the need for chromatography, which simplifies large scale purification of ELPs (Meyer D E, et al., Nat Biotechnol. 1999, 17:1112-1115). Fourth, ELPs can be engineered to approach the viscoelastic properties of native elastin upon crosslinking. Fifth, they are biocompatible, biodegradable, and non-immunogenic (Urry D W, et al., J Bioact Compat Polym. 1991, 6:263-282).

Silk proteins are produced by a variety of insects and spiders, and form fibrous materials in nature, such as spider orb webs and silkworm cocoons. Silk protein is a native block copolymer with alternating large hydrophobic and hydrophilic blocks. The hydrophobic block is generally a repetitive sequence conserved with short-chain amino acids, such as glycine and alanine. The hydrophilic block is less conserved and usually contains non-repetitive sequences rich in charged amino acids. The hydrophilic domain is often substituted with other peptide sequences to achieve specific function for drug delivery. The length of the hydrophobic domain can also be tuned to yield protein NPs with reproducible sizes for drug and gene delivery (Numata K, Biomaterials 2007, 28:1191-1197; Numata K, Adv Drug Deliv Rev. 2010, 62:1497-1508). A recent study demonstrated that a SELP recombinant protein endowed with a cell penetrating peptide could achieve transfection efficiency 45 times higher than that of poly(ethyleneimine). (Numata K, Silk-based Gene Carriers with Cell Membrane Destabilizing Peptides, Biomacromolecules 2010).

Silkworm silk from B. mori silkworm silk-like repeats of GAGAGS (SEQ ID NO: 12) and elastin block (VPGVG) (SEQ ID NO: 13) copolymers, and silk-elastin-like proteins (SELP) constructed by recombinant DNA techniques, have been utilized as gene and drug delivery systems, by forming hydrogels to release adenovirus containing reporter genes.

Many clinical trials involving blood substitutes have been discontinued or held because they induced adverse effects including vasoconstriction, hypertension, or liver failure due to metabolic byproducts. Therefore, new strategies to discover or biosynthesize biocompatible materials, which can deliver oxygen with improved therapeutic efficacy and non-toxicity are needed.

SUMMARY OF THE INVENTION

According to one aspect, the described invention provides a biocompatible pharmaceutical composition comprising a therapeutic amount of a complex comprising a polymer in association with a hemoglobin (Hb), a Hb subunit(s), a Hb fragment(s), a Hb derivative(s), or a functional equivalent thereof that stores and releases oxygen in accordance with an oxygen dissociation curve; wherein the therapeutic amount of the complex is effective to treat a condition caused by blood loss, anemia, or a hemoglobin disorder, and to improve subject survival relative to a control, wherein the polymer is a protein polymer, a polynucleotide polymer, a polysaccharide polymer, or a synthetic polymer.

According to one embodiment, the condition caused by blood loss includes hemorrhagic shock.

According to one embodiment, the protein polymer is associated with the Hb, the Hb subunit(s), the Hb fragment(s), the Hb derivative(s), or the functional equivalent thereof via a covalent bond, an ionic bond, a hydrogen bond, a hydrophobic force, encapsulation, or via fusion. According to another embodiment, the protein polymer is an elastin-like polypeptide (ELP).

According to one embodiment, the ELP and the Hb, the Hb subunit(s), the Hb fragment(s), the Hb derivative(s), or the functional equivalent thereof are operatively linked to form a fusion protein, which is encoded by a polynucleotide comprising a nucleotide sequence that encodes the ELP and a nucleotide sequence that encodes the Hb, the Hb qjsubunit(s), the Hb fragment(s), the Hb derivative(s), or the functional equivalent thereof. According to another embodiment, the ELP and the Hb, the Hb subunit(s), the Hb fragment(s), the Hb derivative(s), or the functional equivalent thereof are operatively linked to form a fusion protein, which is obtained by chemically joining the ELP and the ELP and the Hb, the Hb subunit(s), the Hb fragment(s), the Hb derivative(s), or the functional equivalent thereof.

According to another embodiment, the ELP and the Hb, the Hb subunit(s), the Hb fragment(s), the Hb derivative(s), or the functional equivalent thereof are operatively linked to form a complex, wherein the ELP is assembled into a spherical nanoparticle comprising a core into which the Hb, the Hb subunit(s), the Hb fragment(s), the Hb derivative(s), or the functional equivalent thereof is encapsulated.

According to one embodiment, the fusion protein is assembled into a spherical nanoparticle comprising a core inside of which the Hb, the Hb subunit(s), the Hb fragment(s), the Hb derivative(s), or the functional equivalent thereof is enclosed.

According to one embodiment, the ELP comprises a pentameric amino acid motif (Val-Pro-Gly-Xaa-Gly)n (SEQ ID NO: 11), wherein Xaa specifies any amino acid and n denotes a number of repetitive motifs. According to another embodiment, n=20-90, and Xaa is Serine or a conservative amino acid substitute thereof. According to another embodiment, the conservative amino acid substitute of Serine is Thr. According to another embodiment, n=20-90, and Xaa is Isoleucine or a conservative amino acid substitute thereof. According to another embodiment, the conservative amino acid substitute of Isoleucine is Leu or Met or Val.

According to one embodiment, the ELP comprises a diblock copolymer comprising: a hydrophilic block comprising a pentameric amino acid motif (Val-Pro-Gly-Xaa-Gly)n, wherein n=20-90, and Xaa is a hydrophilic amino acid (SEQ ID NO: 14); and a hydrophobic block comprising a pentameric amino acid motif (Val-Pro-Gly-Xaa-Gly)n, wherein n=20-90, and Xaa is a hydrophobic amino acid (SEQ ID NO: 24). According to another embodiment, for the hydrophilic block, the Xaa is selected from the group consisting of lysine (+), arginine (+), aspartate (−) and glutamate (−), serine, threonine, asparagine, glutamine, and histidine; and for the hydrophobic block, Xaa is selected from the group consisting of alanine, valine, leucine, isoleucine, proline, phenylalanine, tryptophan, and methionine. According to another embodiment, for the hydrophilic block the Xaa is Serine or a conservative amino acid substitute thereof; and for the hydrophobic block the Xaa is Isoleucine or a conservative amino acid substitute thereof. According to another embodiment, the conservative amino acid substitute of Serine is Thr; and the conservative amino acid substitute of Isoleucine is Leu or Met or Val. According to another embodiment, n=48 for hydrophobic block and n=48 for hydrophilic block.

According to one embodiment, the Hb, the Hb subunit(s), the Hb fragment(s), the Hb derivative(s), or the functional equivalent thereof is operatively linked to the C-terminus of the ELP. According to another embodiment, the Hb, the Hb subunit(s), the Hb fragment(s), the Hb derivative(s), or the functional equivalent thereof is operatively linked to the hydrophobic block of the ELP. According to another embodiment, the Hb, the Hb subunit(s), the Hb fragment(s), the Hb derivative(s), or the functional equivalent thereof is of an amino acid sequence selected from the group consisting of SEQ ID No. 4, SEQ ID No. 5 and SEQ ID No. 6. According to another embodiment, the ELP is of amino acid sequence SEQ ID NO: 7. According to another embodiment, the Hb, the Hb subunit(s), the Hb fragment(s), the Hb derivative(s), or the functional equivalent thereof is encoded by a polynucleotide sequence selected from the group consisting of SEQ ID No. 1, SEQ ID No. 2 and SEQ ID No. 3.

According to one embodiment, the biocompatible pharmaceutical composition further comprises one or more pharmaceutically acceptable salts.

According to another aspect, the describe invention provides a method of treating a condition due to blood loss and improving subject survival, the method comprising: (1) administering a biocompatible pharmaceutical composition comprising a therapeutic amount of a complex comprising a polymer associated with a Hb, subunit(s), a Hb fragment(s), a Hb derivative(s), or a functional equivalent thereof, wherein the polymer is a protein polymer, a polynucleotide polymer, a polysaccharide polymer, or a synthetic polymer; wherein the therapeutic amount is effective to store and release oxygen in accordance with an oxygen dissociation curve.

According to one embodiment, the condition caused by blood loss includes hemorrhagic shock.

According to one embodiment, the protein polymer is associated with the Hb, the Hb subunit(s), the Hb fragment(s), the Hb derivative(s), or the functional equivalent thereof via a covalent bond, an ionic bond, a hydrogen bond, a hydrophobic force, encapsulation, or via fusion. According to another embodiment, the protein polymer is an elastin-like polypeptide (ELP). According to another embodiment, the ELP and the Hb, the Hb subunit(s), the Hb fragment(s), the Hb derivative(s), or the functional equivalent thereof are operatively linked to form a fusion protein, which is encoded by a polynucleotide comprising a nucleotide sequence that encodes the ELP and a nucleotide sequence that encodes the Hb, the Hb subunit(s), the Hb fragment(s), the Hb derivative(s), or the functional equivalent thereof. According to another embodiment, the ELP and the Hb, the Hb subunit(s), the Hb fragment(s), the Hb derivative(s), or the functional equivalent thereof are operatively linked to form a fusion protein, which is obtained by chemically joining the ELP and the ELP and the Hb, the Hb subunit(s), the Hb fragment(s), the Hb derivative(s), or the functional equivalent thereof. According to another embodiment, the ELP is assembled into a spherical nanoparticle comprising a core inside of which the Hb, the Hb subunit(s), the Hb fragment(s), the Hb derivative(s), or the functional equivalent thereof is encapsulated.

According to one embodiment, the fusion protein is assembled into a spherical nanoparticle comprising a core inside of which the Hb, the Hb subunit(s), the Hb fragment(s), the Hb derivative(s), or the functional equivalent thereof is enclosed.

According to one embodiment, the ELP comprises a pentameric amino acid motif (Val-Pro-Gly-Xaa-Gly)n, wherein Xaa specifies any amino acid and n denotes a number of repetitive motifs (SEQ ID NO: 11). According to another embodiment, n=20-90, and Xaa is Serine or a conservative amino acid substitute thereof. According to another embodiment, the conservative amino acid substitute of Serine is Thr. According to another embodiment, wherein n=20-90, and Xaa is Isoleucine or a conservative amino acid substitute thereof. According to another embodiment, the conservative amino acid substitute of Isoleucine is Leu or Met or Val.

According to one embodiment, the ELP comprises a diblock copolymer comprising: a hydrophilic block comprising a pentameric amino acid motif (Val-Pro-Gly-Xaa-Gly)n, wherein n=20-80, and Xaa is a hydrophilic amino acid (SEQ ID NO: 15); and a hydrophobic block comprising a pentameric amino acid motif (Val-Pro-Gly-Xaa-Gly)n, wherein n=20-80, and Xaa is a hydrophobic amino acid (SEQ ID NO: 25). According to another embodiment, the Xaa is selected from the group consisting of lysine (+), arginine (+), aspartate (−) and glutamate (−), serine, threonine, asparagine, glutamine, and histidine in the hydrophilic block; and Xaa is selected from the group consisting of alanine, valine, leucine, isoleucine, proline, phenylalanine, tryptophan, and methionine in the hydrophobic block. According to another embodiment, the hydrophilic block the Xaa is Serine or a conservative amino acid substitute thereof and for the hydrophobic block the Xaa is Isoleucine or a conservative amino acid substitute thereof. According to another embodiment, the conservative amino acid substitute of Serine is Thr, and the conservative amino acid substitute of Isoleucine is Leu or Met or Val. According to another embodiment, n=48 for hydrophobic block and n=48 for hydrophilic block.

According to one embodiment, the Hb, the Hb subunit(s), the Hb fragment(s), the Hb derivative(s), or the functional equivalent thereof is operatively linked to the C-terminus of the ELP. According to another embodiment, the Hb, the Hb subunit(s), the Hb fragment(s), the Hb derivative(s), or the functional equivalent thereof is operatively linked to the hydrophobic block of the ELP. According to another embodiment, the Hb, the Hb subunit(s), the Hb fragment(s), the Hb derivative(s), or the functional equivalent thereof is of amino acid sequence selected from the group consisting of SEQ ID No. 4, SEQ ID No. 5 and SEQ ID No. 6. According to another embodiment, the ELP is of amino acid sequence SEQ ID NO. 7. According to another embodiment, the Hb, the Hb subunit(s), the Hb fragment(s), the Hb derivative(s), or the functional equivalent thereof is encoded by a polynucleotide sequence selected from the group consisting of SEQ ID No. 1, SEQ ID No. 2 and SEQ ID No. 3.

According to one embodiment, the biocompatible pharmaceutical composition further comprises one or more pharmaceutically acceptable salts.

According to one embodiment, the method further comprises constructing a vector and/or host cell comprising a fusion gene polynucleotide that comprises a polynucleotide sequence coding a fusion protein comprising ELP and Hb, the Hb subunit(s), the Hb fragment(s), the Hb derivative(s), or the functional equivalent thereof.

According to one embodiment, the method further comprises preparing the fusion protein by expressing the fusion gene polynucleotide in an expression system.

According to one embodiment, the method further comprises separating or purifying the fusion protein from the expression system.

According to one embodiment, the method further comprises preparing the fusion protein by chemically operatively linking the ELP and Hb, the Hb subunit(s), the Hb fragment(s), the Hb derivative(s), or the functional equivalent thereof.

DETAILED DESCRIPTION OF THE INVENTION

Definitions

Figure 1:
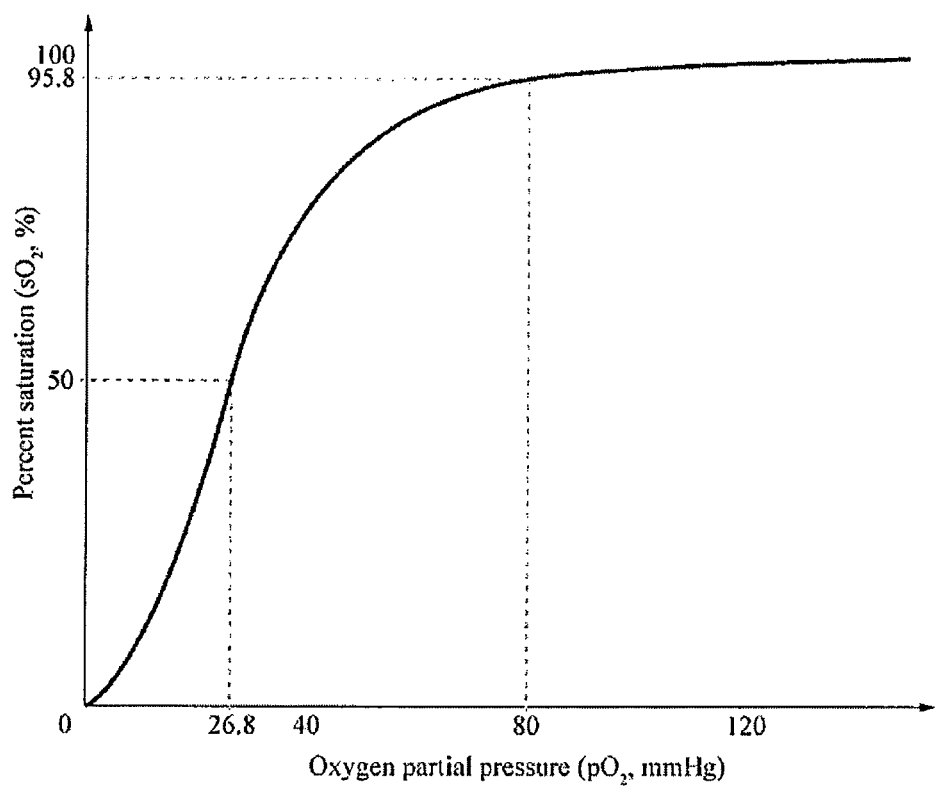
FIG. 1. The oxyhemoglobin dissociation curve plots the proportion of hemoglobin in its saturated form on the vertical axis against the prevailing oxygen tension on the horizontal axis.
Figure 2:
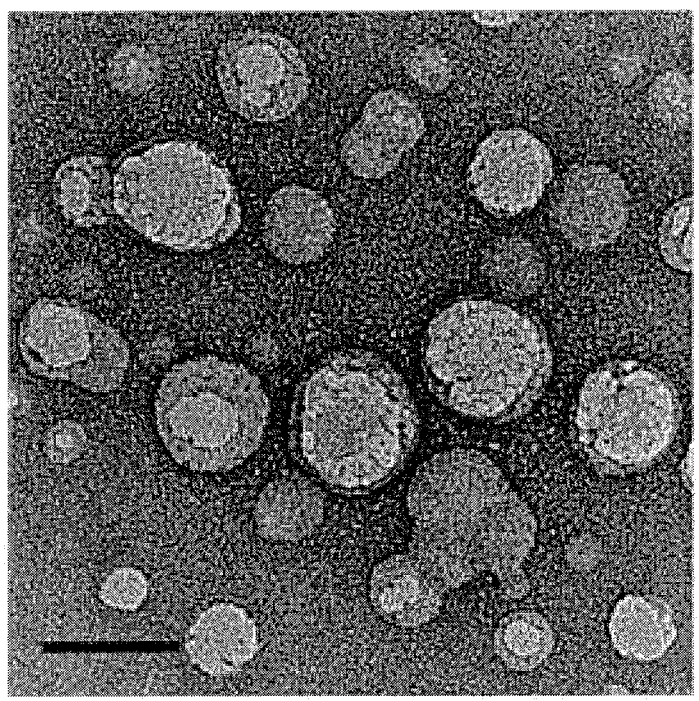
FIG. 2 is a transmission electron microscopy (TEM) of negatively stained nanoparticles (white round objects) with an average particle diameter of about 33 nm stained with uranyl acetate. (S. M. Janib et al., Integr Biol, 2013)
Figure 3:
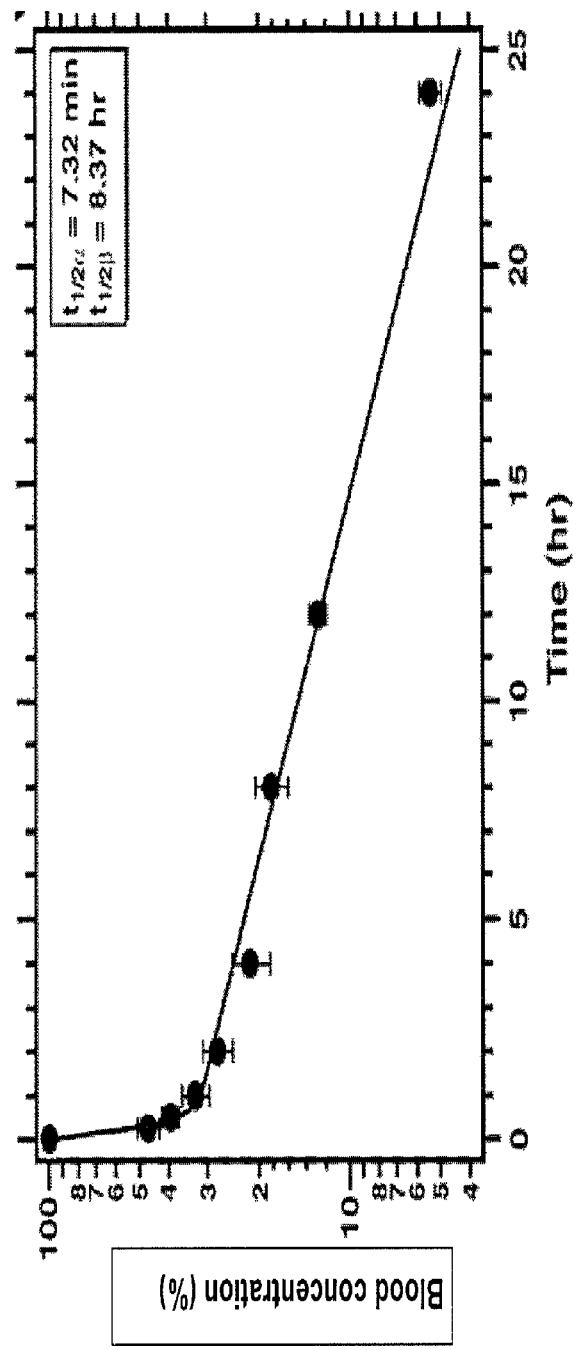
FIG. 3 shows that polypeptide nanoparticles exhibit an elimination half-life of 6-8 hrs in mouse serum (J. A. MacKay and A. Hilkoti, Int J Hyperthermia, 2008)
Figure 4:
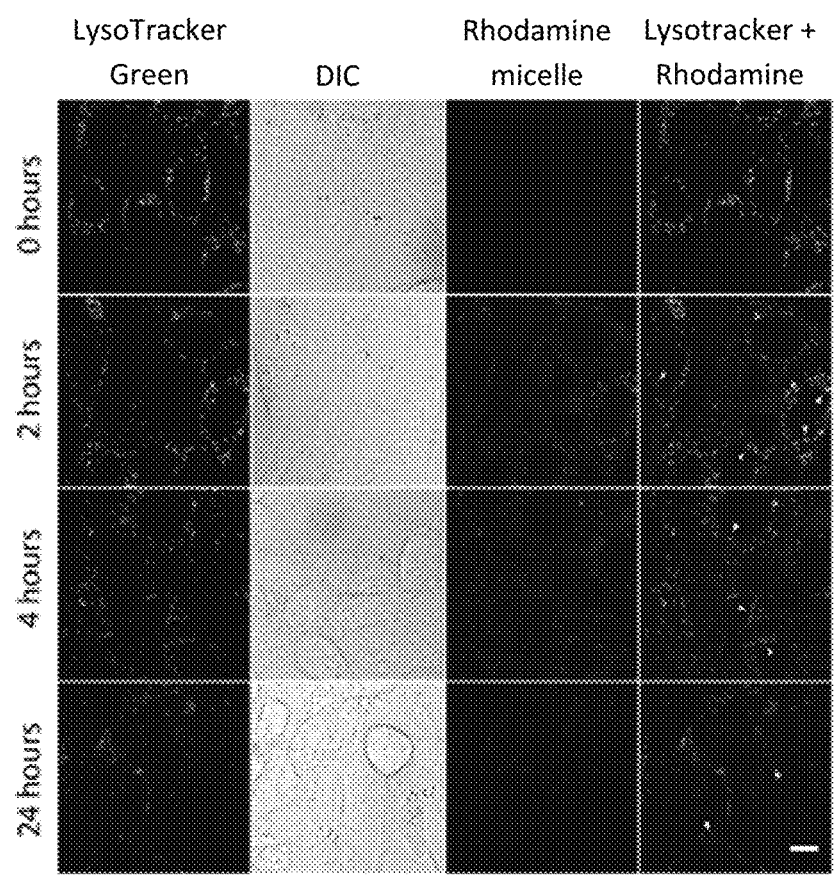
FIG. 4 shows in vitro studies demonstrating that mice hepatocytes enzymatically degrade nanoparticles (M. Shah et al. Protein Sci, 2012)
Figure 5:
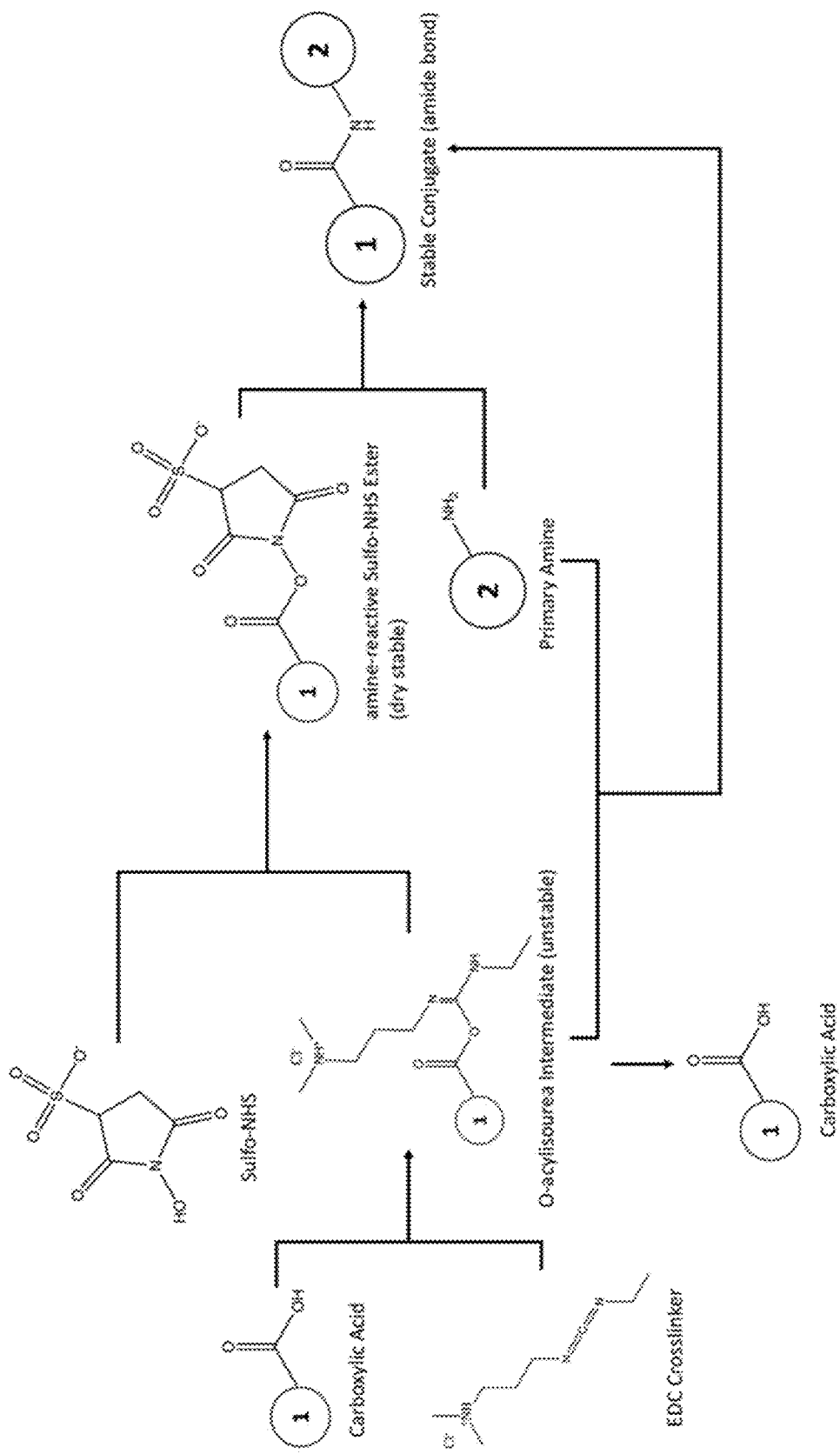
FIG. 5 is a schematic of the chemical conjugation process used to link elastin-like polypeptides (ELPs) to hemoglobin.

The terms "administering" or "administration" as used herein are used interchangeably to mean the giving or applying of a substance and include in vivo administration, as well as administration directly to tissue ex vivo.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations, which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid, which is altered so as to increase the half-life of the peptide or to increase the potency of the peptide, or to increase the bioavailability of the peptide.

Based on its propensity to be in contact with polar solvent like water, a side chain may be classified as hydrophobic (low propensity to be in contact with water), polar or charged (energetically favorable contact with water or hydrophilic). The charged amino acid residues include lysine (+), arginine (+), aspartate (−) and glutamate (−). Polar amino acids include serine, threonine, asparagine, glutamine, and histidine. The hydrophobic amino acids include alanine, valine, leucine, isoleucine, proline, phenylalanine, tryptophan, and methionine. Cysteine may be considered slightly polar or nonpolar. Tyrosine may be considered polar (due to hydroxyl group on phenyl ring in side chain) or non-polar (due to aromatic ring).

The following represent groups of amino acids that are conservative substitutions for one another:
Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).

The term "amphiphilic" as used herein refers to a compound containing a large organic cation or anion, which possesses a long unbranched hydrocarbon chain, e.g. $CH_3(CH_2)nCO_2\text{-}M+$, $CH_3(CH_2)nN+(CH_3)_3X-$ (n>7), $CH_3(CH_2)nSO_3\text{-}M+$. The existence of distinct polar (hydrophilic) and nonpolar (hydrophobic) regions in the molecule promotes the formation of micelles in dilute aqueous solution.

The term "associate" and its various grammatical forms as used herein refers to joining, connecting, or combining to, either directly, indirectly, actively, inactively, inertly, non-inertly, completely or incompletely.

The term "biocompatible" as used herein refers to causing no clinically relevant tissue irritation, injury, toxic reaction, or immunological reaction to living tissue.

The term "biodegradable" as used herein refers to material that will break down actively or passively over time by simple chemical processes, by action of body enzymes or by other similar biological activity mechanisms.

The term "block" as used herein refers to a portion of a macromolecule, comprising many constitutional units, that has at least one feature, which is not present in the adjacent portions.

The term "block copolymer" as used herein refers to a copolymer that is a block polymer. In a block copolymer, adjacent blocks are constitutionally different, i.e., each of these blocks comprises constitutional units derived from different characteristic species of monomer or with different composition or sequence distribution of constitutional units.

The term "blood substitutes" as used herein refers to an oxygen storage and delivery therapeutic. One type of the artificial blood substitute is a "hemoglobin-based oxygen carrier".

The term "carrier" as used herein refers to a usually inactive substance that acts as a vehicle for an active substance. The terms "excipient", "vehicle", or "carrier" refer to substances that facilitate the use of, but do not deleteriously react with, the active compound(s) when mixed with it. The term "active" refers to the ingredient, component or constituent of the compositions of the present invention responsible for the intended therapeutic effect. Carriers must be of sufficiently high purity and of sufficiently low toxicity to render them suitable for administration to the subject being treated. The carrier can be inert, or it can possess pharmaceutical benefits. The term "pharmaceutically acceptable carrier" as used herein refers to any substantially non-toxic carrier conventionally useful for administration of pharmaceuticals in which the active component will remain stable and bioavailable. The pharmaceutical compositions within the described invention contain a therapeutically effective amount of included in a pharmaceutically-acceptable carrier. The term "pharmaceutically-acceptable carrier" as used herein refers to one or more compatible solid or liquid filler, diluents or encapsulating substances which are suitable for administration to a human or other vertebrate animal. The term "carrier" as used herein refers to an organic or inorganic ingredient, natural or synthetic, with which the active ingredient is combined to facilitate the application. The components of the pharmaceutical compositions also are capable of being commingled in a manner such that there is no interaction which would substantially impair the desired pharmaceutical efficiency.

The term "cell" is used herein to refer to the structural and functional unit of living organisms and is the smallest unit of an organism classified as living.

The term "cell culture" as used herein refers to establishment and maintenance of cell populations in vitro derived from dispersed cells taken from original tissues, primary culture, or from a cell line or cell strain.

The term "coacervation" or phase separation as used herein refers to a macromolecular aggregation process brought about by partial desolvation of fully solvated macromolecules. A distinction is drawn between simple and complex coacervation. In simple coacervation, there is only one colloidal solute, and phase separation is induced by addition of alcohol or salt, change in temperature or change in pH. In complex coacervation, which deals with separations containing more than one solute, an oppositely charged substance is added to a polymer solution leading to the formation of a coacervate phase via an anion-cation interaction. These phase separation processes can be used to encapsulate solid or liquid drug particles, which are dispersed in a polymer solution.

The term "complex" as used herein refers to an entity composed of molecules in which the constituents maintain much of their chemical identity.

The term "contact" and its various grammatical forms as used herein refers to a state or condition of touching or of immediate or local proximity.

The term "constitutional repeating unit" as used herein refers to the smallest constitutional unit, the repetition of which constitutes a regular macromolecule (or oligomer molecule or block).

The term "constitutional unit" as used herein refers to an atom or group of atoms in a macromolecule or oligomer molecule, comprising a part of the chain together with its pendant atoms or groups of atoms, if any.

The term "copolymer" as used herein refers to a polymer derived from more than one species of monomer. Copolymers that are obtained by copolymerization of two monomer species are sometimes termed bipolymers, those obtained from three monomers terpolymers, those obtained from four monomers quaterpolymers, etc.

The term "copolymerization" as used herein refers to polymerization in which a copolymer is formed.

The term "critical micelle temperature (CMT) also known as Krafft point" as used herein refers to a narrow temperature range above which the solubility of a surfactant rises sharply. At this temperature, the solubility of the surfactant becomes equal to the critical micelle concentration. It is best determined, for example, by locating the abrupt change in slope of a graph of the logarithm of the solubility against t or 1/T.

The term "crosslink" as used herein refers to a constitutional unit connecting two parts of a macromolecule that were separate molecules or on distant parts of the same molecule. A network may be thought to consist of many "primary chains" that are interconnected by a number of crosslinks. The crosslink can be a covalent bond, a site of weaker chemical interactions, a portion of crystallites, and even a physical entanglement.

The term "diblock copolymer" as used herein refers to a polymer consisting of two types of monomers, A and B. The monomers are arranged such that there is a chain of each monomer, and those two chains are grafted together to form a single copolymer chain.

The term "effective amount" as used herein refers to the amount necessary or sufficient to realize a desired biologic effect.

The term "encapsulate" or "encapsulation" as used herein refers to a process in which tiny particles are enclosed inside a semipermeable membrane, usually approximately spherical.

The term "fragment" or "peptide fragment" as used herein refers to a small part derived, cut off, or broken from a larger peptide, polypeptide or protein, which retains the desired biological activity of the larger peptide, polypeptide or protein.

The terms "functional equivalent" or "functionally equivalent" are used interchangeably herein to refer to substances, molecules, polynucleotides, proteins, peptides, or polypeptides having similar or identical effects. The "hemoglobin functional equivalent" as used herein refers to a molecule, a compound or a complex that appropriately stores and releases oxygen in accordance with an oxygen dissociation curve.

The term "fusion protein" as used herein refers to a protein or polypeptide constructed by combining multiple protein domains or polypeptides for the purpose of creating a single polypeptide or protein with functional properties derived from each of the original proteins or polypeptides. Creation of a fusion protein may be accomplished by operatively ligating or linking two different nucleotides sequences that encode each protein domain or polypeptide via recombinant DNA technology, thereby creating a new polynucleotide sequences that codes for the desired fusion protein. Alternatively, a fusion protein maybe created by chemically joining the desired protein domains.

The term "gene cassette" is a type of mobile genetic element or cassette that contains a gene of interest and a recombination site. The gene may exist incorporated into an integron or freely as circular DNA. Gene cassettes often carry antibiotic resistance genes. The cassette is a pre-existing structure into which an insert can be moved. A gene conversion process occurs in which the old gene is replaced with a copy of a silent gene and the new copy becomes active. As the process involves replacing one ready-made construct with another in an active slot, it is termed a cassette mechanism.

The term "genetic engineering" or "genetically engineered" as used herein refers to the manipulation of DNA to produce new types of organisms, usually by inserting or deleting genes.

The term "hemorrhagic shock" as used herein refers to a condition of reduced tissue perfusion, resulting in the inadequate delivery of oxygen and nutrients that are necessary for cellular function. Whenever cellular oxygen demand outweighs supply, both the cell and the organism are in a state of shock. On a multicellular level, the definition of shock becomes more difficult because not all tissues and organs will experience the same amount of oxygen imbalance for a given clinical disturbance. The 4 classes of shock, are Hypovolemic, Vasogenic (septic), Cardiogenic, and Neurogenic. (Blalock A. Principle of Surgical Care, Shock, and Other Problems. St Louis: Mosby; 1940.) Hypovolemic shock, the most common type, results from a loss of circulating blood volume from clinical etiologies, such as penetrating and blunt trauma, gastrointestinal bleeding, and obstetrical bleeding. Hemorrhagic shock produced by rapid and significant loss of intravascular volume may lead sequentially to hemodynamic instability, decreases in oxygen delivery, decreased tissue perfusion, cellular hypoxia, organ damage, and death.

The term "hybridization" refers to the process of combining complementary, single-stranded nucleic acids into a single molecule. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. Measuring the effects of base incompatibility by quantifying the rate at which two strands anneal can provide information as to the similarity in base sequence between the two strands being annealed. The term "specifically hybridizes" as used herein refers to the process whereby a nucleic acid distinctively or definitively forms base pairs with complementary regions of at least one strand of DNA that was not originally paired to the nucleic acid. For example, a nucleic acid that may bind or hybridize to at least a portion of an mRNA of a cell encoding a peptide comprising a specific protein sequence may be considered a nucleic acid that specifically hybridizes. A nucleic acid that selectively hybridizes undergoes hybridization, under stringent hybridization conditions, of the nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, at least 90% sequence identity, or at least 100% sequence identity (i.e., complementary) with each other.

The term "hydrogel" as used herein refers to gel in which the swelling agent is water. The network component of a hydrogel is usually a polymer network.

The term "liposome" as used herein refers to an artificially formed single or multi-layer spherical lipid bilayer structure, for example, made from solution of lipids in organic solvents dispersed in aqueous media.

The term "micelle" as used herein refers to an electrically charged colloidal particle, usually organic in nature, in which all of the hydrophobic portions of the molecule are inwardly directed, leaving the hydrophilic portions in contact with the surrounding aqueous phase. If the major phase is hydrophobic, the inverse arrangement will be found.

The term "molecule" as used herein refers to a chemical unit composed of one or more atoms.

The term "monomer" as used herein refers to a substance, each of the molecules of which can, on polymerization, contribute one or more constitutional units in the structure of the macromolecule.

The term "mutation" as used herein refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "nanocarrier" as used herein refers to a nanomaterial being used as a transport module for another substance, such as a drug. Commonly used nanocarriers include micelles, polymers, carbon-based materials, liposomes and other substances.

The term "nanoparticle" or nanomaterial as used herein refers to a particle or material with at least one dimension of $1 \times 10^{-9}$ m-$999 \times 10^{-9}$ m.

The term "natural polymer" as used herein refers to a polymer derived from biological systems, including, without limitation, a protein, DNA, RNA and polysaccharides.

The term "nucleic acid" as used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" as used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The phrase "operatively linked" as used herein refers to a linkage in which two or more protein domains or polypeptides are ligated or combined via recombinant DNA technology or chemical reaction such that each protein domain or polypeptide of the resulting fusion protein retains its original function.

The term "P50" as used herein refers to the partial pressure of oxygen (PO2) at which hemoglobin becomes 50% saturated with oxygen.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure.

The term "particle" as used herein refers to an extremely small constituent (e.g., nanoparticles, microparticles, or in some instances larger).

The term "peptide" is used herein to refer to two or more amino acids joined by a peptide bond.

The term "pharmaceutically acceptable salt" as used herein refers to those salts, which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts, which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids, which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The term "pharmaceutical composition" as used herein refers to a composition that is employed to prevent, reduce in intensity, cure or otherwise treat a target condition or disease.

The term "polymer" as used herein refers to any of various chemical compounds made of smaller, identical molecules (called monomers) linked together. Polymers generally have high molecular weights. The process by which molecules are linked together to form polymers is called "polymerization."

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The term "protein" is used herein to refer to a large complex molecule or polypeptide composed of amino acids. The sequence of the amino acids in the protein is determined by the sequence of the bases in the nucleic acid sequence that encodes it.

The term "polypeptide" is used herein in its broadest sense to refer to a sequence of subunit amino acids, amino acid analogs or peptidomimetics, wherein the subunits are linked by peptide bonds.

The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation, which do not occur naturally. Circular, branched and branched circular polypeptides may be synthesized by non-translation natural process and by entirely synthetic methods, as well.

The term "phase" as used herein refers to a distinct state of matter in a system in which matter that is identical in chemical composition and physical state and separated from other material by the phase boundary.

The term "recombinant proteins" as used herein refers to proteins that can result from the expression of recombinant DNA within living cells are termed recombinant proteins.

The term "shock" as used herein refers to a state of inadequate perfusion, which does not sustain the physiologic needs of organ tissues. Many conditions, including blood loss but also including nonhemorrhagic states such as dehydration, sepsis, impaired autoregulation, obstruction, decreased myocardial function, and loss of autonomic tone, may produce shock or shocklike states.

The term "solution" as used herein refers to a homogeneous mixture of two or more substances. It is frequently, though not necessarily, a liquid. In a solution, the molecules of the solute (or dissolved substance) are uniformly distributed among those of the solvent.

The term "solvate" as used herein refers to a complex formed by the attachment of solvent molecules to that of a solute.

The term "solvent" as used herein refers to a substance capable of dissolving another substance (termed a "solute") to form a uniformly dispersed mixture (solution).

The phrase "subject" as used herein refers to a patient that (i) will be administered at least pharmaceutical composition of the described invention, (ii) is receiving at least pharmaceutical composition of the described invention; or (iii) has received at least one pharmaceutical composition of the described invention, unless the context and usage of the phrase indicates otherwise.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein.

The terms "therapeutically effective amount", or "effective amount" or an "amount effective", or "pharmaceutically effective amount" are used interchangeably to refer to an amount that is sufficient to provide the intended benefit of treatment. An effective amount of an active agent that can be employed according to the described invention generally ranges from about 50 mg/kg body weight to about 1.5 g/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutically effective amount", "amount effective" and "pharmaceutically effective amount" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is preferred generally that a maximum dose be used, that is, the highest safe dose according to some medical judgment. "Dose" and "dosage" are used interchangeably herein.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "Tropoelastin" as used herein refers to a protein that is expressed and post-translationally modified from the gene encoding elastin, prior to cross-linking to form elastin. Martin et al. (1995) Gene, 154, 159-166, details the making of the synthetic gene and subsequent expression of synthetic human elastin (SHEL). A used herein, "tropoelastin" encompasses full length tropoelastin, isoforms of tropoelastin, genetically engineered tropoelastin constructs, and fragments and derivatives of tropoelastin.

The term "transition temperature (for liquid crystals)" as used herein refers to the temperature at which the transition from mesophase X to mesophase Y occurs. A mesophase is a phase occurring over a definite range of temperature, pressure, or concentration within a mesomorphic state. A mesomorphic state of matter is one in which the degree of molecular order is intermediate between the perfect three-dimensional, long-range positional and orientational order found in solid crystals and the absence of long-range order found in isotropic liquids, gases, and amorphous solids.

The terms "variants", "mutants", and "derivatives" are used herein to refer to sequences with substantial identity to a reference sequence. A skilled artisan can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known.

According to one aspect, the described invention provides a pharmaceutical composition comprising a polymer and a hemoglobin or functional equivalent thereof, wherein the pharmaceutical composition is effective to deliver oxygen, prevent or treat conditions caused by blood loss or anemia or other blood disorder, and improve subject survival.

According to one embodiment, The composition is prepared by bringing into association or contact a protein polymer and a hemoglobin, subunit(s), fragment(s), derivatives(s) or functional equivalent thereof or a pharmaceutically acceptable salt or solvate thereof ("active compound") with a carrier which constitutes one or more accessory agents. In general, the formulations are prepared by uniformly and intimately bringing into association the active agent(s) with liquid carriers or finely divided solid carriers or both and then, if necessary, shaping the product into the desired formulation.

According to one embodiment of the described invention, the condition caused by blood loss includes, without limitation, hemorrhagic shock.

According to one embodiment of the described invention, the polymer is a natural polymer, a synthetic polymer (including degradable and non-degradable), a hybrid polymer, or a recombinant polymer.

Exemplary synthetic degradable polymers include, without limitation, poly(c-caprolactone) (PCL), poly(ε-caprolactone-co-ethyl ethylene phosphate) (PCLEEP), poly(lactic acid) (PLA), poly(lactic-co-glycolic acid) (PLGA), poly(lactic acid-co-ε-caprolactone) (PLACL), and polydioxanone (PDO).

According to one embodiment, the polymer is a protein polymer, a polynucleotide polymer (e.g. a DNA, or an RNA), a polysaccharide polymer, or a synthetic polymer.

According to one embodiment, the protein polymer is a natural protein polymer, a synthetic protein polymer, or a recombinant protein polymer.

According to one embodiment, the hemoglobin is natural, synthetic, recombinant, a fragment, a subunit, or a derivative.

According to one embodiment, a hemoglobin functional equivalent includes, without limitation, a molecule comprising an affinity for oxygen.

According to one embodiment, the hemoglobin, subunit(s), fragment(s), derivative(s), or functional equivalent thereof can be formulated per se or in salt form.

According to one embodiment, the hemoglobin or subunit(s) or fragment(s) or derivative(s) or functional equivalent thereof can be truncated or modified.

According to one embodiment, the polymer binds to the hemoglobin, subunit(s), fragment(s), derivative(s), or functional equivalent thereof via a covalent bond, an ionic bond, a hydrogen bond, a hydrophobic force, encapsulation, or is operatively linked via fusion.

According to one embodiment, the polymer contacts the hemoglobin, subunit(s), fragment(s), derivative(s), or functional equivalent thereof.

According to one embodiment, the polymer is operatively linked to a hemoglobin subunit(s) or fragment(s) thereof.

According to one embodiment, the polymer binds to hemoglobin via a chemical reaction.

According to another embodiment, the polymer and hemoglobin comprise a fusion protein.

According to one embodiment, the protein polymer is an elastin-like protein (ELP), a silk-like protein (SLP), or a silk-elastin like protein (SELP).

According to one embodiment, the ELP comprises a pentameric amino acid motif of (Val-Pro-Gly-Xaa-Gly)n, wherein Xaa specifies any amino acid and n denotes the number of repetitive motifs (SEQ ID NO: 11).

According to some such embodiments, n is at least 20, 25, 30, 35, 40, 45, 50, 55, 60, 65, 70, 75, 80, 85, 90. According to some embodiments, n ranges from 20-30, 20-40, 20-50, 20-60, 20-70, 20-80, 20-90, 30-40, 30-50, 30-60, 30-70, 30-80, 30-90, 40-50, 40-60, 40-70, 40-80, 40-90, 50-60, 50-70, 50-80, 50-90, 60-70, 60-80, 60-90, 70-80, 70-90, or 80-90.

According to one embodiment, the ELP can be formulated per se or in salt form.

According to one embodiment, the ELP can be truncated, modified, or derivatized.

According to one embodiment of the described invention, the ELP is a diblock copolymer, comprising a hydrophobic block of amino acids and a hydrophilic block of amino acids, which can assemble into a spherical nanoparticle above a critical micelle temperature (CMT) to encapsulate the hemoglobin, a subunit(s), a fragment(s), a derivative(s), or a functional equivalent thereof at its core.

According to one embodiment, the hydrophilic block of the ELP diblock copolymer comprises a pentameric amino acid motif of (Val-Pro-Gly-Xaa-Gly)n, wherein n=20-90, and Xaa is a hydrophilic amino acid (SEQ ID NO: 14), for example, lysine (+), arginine (+), aspartate (−), glutamate (−), serine, threonine, asparagine, glutamine, and histidine.

According to one embodiment, the hydrophilic block of the ELP diblock copolymer comprises a pentameric amino acid motif of (Val-Pro-Gly-Xaa-Gly)n, wherein n=20-90, and Xaa is Ser or a conservative amino acid substitute thereof, for example, Thr (SEQ ID NO: 16).

According to one embodiment, the hydrophilic block of the ELP diblock copolymer comprises a pentameric amino acid motif of (Val-Pro-Gly-Xaa-Gly)n, wherein n=40-60 (SEQ ID NO: 17).

According to one embodiment, the hydrophobic block of the ELP diblock copolymer comprises a pentameric amino acid motif of (Val-Pro-Gly-Ser-Gly)n, wherein n=20-90, and Xaa is a hydrophobic amino acid (SEQ ID NO: 18), for example, alanine, valine, leucine, isoleucine, proline, phenylalanine, tryptophan, and methionine.

According to one embodiment, the hydrophobic block of the ELP diblock copolymer comprises a pentameric amino acid motif of (Val-Pro-Gly-Xaa-Gly)n, wherein n=20-90, and Xaa is Ile or a conservative amino acid substitute thereof, for example, Leu or Met or Val (SEQ ID NO: 19).

According to one embodiment, the hydrophobic block of the ELP diblock copolymer comprises a pentameric amino acid motif of (Val-Pro-Gly-Xaa-Gly)n, wherein n=40-60 (SEQ ID NO: 17).

According to one embodiment of the described invention, the hemoglobin subunit or fragment is operatively linked to the hydrophobic block of the ELP to facilitate enclosing of hemoglobin or functional equivalent thereof within the core of an ELP nanoparticle.

According to one embodiment, the hemoglobin, subunit(s), fragment(s), derivative(s), or functional equivalent thereof is operatively linked to the C-terminus of the ELP.

According to one embodiment, the hemoglobin, subunit(s), fragment(s), derivative(s), or functional equivalent thereof is operatively linked to a hydrophobic block of the ELP.

According to one embodiment, the hemoglobin, subunit(s), fragment(s), derivative(s), or functional equivalent thereof is operatively linked to the hydrophobic block of the ELP via a chemical reaction.

According to another embodiment, the hemoglobin, subunit(s), fragment(s), derivative(s), or functional equivalent thereof that is operatively linked to the hydrophobic block of the ELP comprises a fusion protein.

According to one embodiment, the specific polynucleotide is contained in a vector and/or host cell.

According to one embodiment, the fusion protein is encoded by a polynucleotide comprising a nucleotide sequence that encodes a recombinant ELP operatively linked to a nucleotide sequence that encodes a hemoglobin, a subunit, a fragment, or a functional equivalent thereof.

According to one embodiment, the polynucleotide sequence that encodes the hemoglobin, a subunit, a fragment, or a functional equivalent thereof is selected from the group consisting of SEQ ID NO. 1, SEQ ID NO. 2 and SEQ ID NO. 3.

According to one embodiment, a hemoglobin, a subunit, a fragment, or a functional equivalent thereof comprises an amino acid sequence selected from the group consisting of: SEQ ID NO. 4, SEQ ID NO. 5 and SEQ ID NO. 6.

According to one embodiment, the ELP comprises amino acid sequence SEQ ID NO. 7.

According to one embodiment, the fusion protein comprises an ELP of amino acid sequence SEQ ID NO. 7 operatively linked to one or more hemoglobin subunits of amino acid sequences selected from the group consisting of SEQ ID NO. 4, SEQ ID NO. 5 and SEQ ID NO. 6.

According to one embodiment, the fusion protein comprises amino acid sequence SEQ ID NO. 8 containing an ELP of amino acid sequence SEQ ID NO. 7 operatively linked to a hemoglobin subunit of amino acid sequence SEQ ID NO. 4.

According to one embodiment, the fusion protein comprises amino acid sequence SEQ ID NO. 9 containing an ELP of amino acid sequence SEQ ID NO. 7 operatively linked to a hemoglobin subunit of amino acid sequence SEQ ID NO. 5.

According to one embodiment, the fusion protein comprises amino acid sequence SEQ ID NO. 10 containing an ELP of amino acid sequence SEQ ID NO. 7 operatively linked to a hemoglobin subunit of amino acid sequence SEQ ID NO. 6.

According to one embodiment of the described invention, the pharmaceutical composition comprises a therapeutic amount of a protein polymer-encapsulated hemoglobin molecule.

According to one embodiment, the protein polymer-encapsulated hemoglobin molecule is a fusion protein consisting essentially of a protein polymer operatively linked to a hemoglobin subunit or a fragment, wherein the hemoglobin is encapsulated within the protein polymer.

According to one embodiment, the pharmaceutical composition further comprises one or more pharmaceutically acceptable carriers.

According to another aspect, the described invention provides a method for treating a condition due to blood loss, and improving subject survival, the method comprising: (1) administering a biocompatible pharmaceutical composition comprising a therapeutic amount of a complex comprising a polymer associated with a hemoglobin, a subunit(s), a fragment(s), a derivative(s), or a functional equivalent thereof.

According to one embodiment of the described invention, the condition caused by blood loss includes, without limitation, hemorrhagic shock.

According to one embodiment of the described invention, the polymer is a natural polymer, a synthetic polymer (including degradable and non-degradable), a hybrid polymer, or a recombinant polymer.

Exemplary synthetic degradable polymers include, without limitation, poly(ε-caprolactone) (PCL), poly(ε-caprolactone-co-ethyl ethylene phosphate) (PCLEEP), poly(lactic acid) (PLA), poly(lactic-co-glycolic acid) (PLGA), poly (lactic acid-co-ε-caprolactone) (PLACL), and polydioxanone (PDO).

According to one embodiment, the polymer is a protein polymer, a polynucleotide polymer (e.g. a DNA, or an RNA), a polysaccharide polymer, or a synthetic polymer.

According to one embodiment, the protein polymer is a natural protein polymer, a synthetic protein polymer, or a recombinant protein polymer.

According to one embodiment, the hemoglobin is natural, synthetic, recombinant, a fragment, a subunit, or a derivative.

According to one embodiment, a hemoglobin functional equivalent includes, without limitation, a molecule comprising an affinity for oxygen.

According to one embodiment, the hemoglobin, subunit(s), fragment(s), derivative(s), or functional equivalent thereof can be formulated per se or in salt form.

According to one embodiment, the hemoglobin or subunit(s) or fragment(s) or derivative(s) or functional equivalent thereof can be truncated or modified.

According to one embodiment, the polymer binds to the hemoglobin, subunit(s), fragment(s), derivative(s), or functional equivalent thereof via a covalent bond, an ionic bond, a hydrogen bond, a hydrophobic force, encapsulation, or is operatively linked via fusion.

According to one embodiment, the polymer contacts the hemoglobin, subunit(s), fragment(s), derivative(s), or functional equivalent thereof.

According to one embodiment, the polymer is operatively linked to a hemoglobin subunit(s) or fragment(s) thereof.

According to one embodiment, the polymer binds to hemoglobin via a chemical reaction.

According to another embodiment, the polymer and hemoglobin comprise a fusion protein.

According to one embodiment, the protein polymer is an elastin-like protein (ELP), a silk-like protein (SLP), or a silk-elastin like protein (SELP).

According to one embodiment, the ELP comprises a pentameric amino acid motif of (Val-Pro-Gly-Xaa-Gly)n, wherein Xaa specifies any amino acid and n denotes the number of repetitive motifs (SEQ ID NO: 11).

According to some such embodiments, n is at least 20, 25, 30, 35, 40, 45, 50, 55, 60, 65, 70, 75, 80, 85, 90. According to some embodiments, n ranges from 20-30, 20-40, 20-50, 20-60, 20-70, 20-80, 20-90, 30-40, 30-50, 30-60, 30-70, 30-80, 30-90, 40-50, 40-60, 40-70, 40-80, 40-90, 50-60, 50-70, 50-80, 50-90, 60-70, 60-80, 60-90, 70-80, 70-90, or 80-90.

According to one embodiment, the ELP can be formulated per se or in salt form.

According to one embodiment, the ELP can be truncated, modified, or derivatized.

According to one embodiment of the described invention, the ELP is a diblock copolymer, comprising a hydrophobic block of amino acids and a hydrophilic block of amino acids, which can assemble into a spherical nanoparticle above a critical micelle temperature (CMT) to encapsulate the hemoglobin, a subunit(s), a fragment(s), a derivative(s), or a functional equivalent thereof at its core.

According to one embodiment, the hydrophilic block of the ELP diblock copolymer comprises a pentameric amino acid motif of (Val-Pro-Gly-Xaa-Gly)n, wherein n=20-90, and Xaa is a hydrophilic amino acid (SEQ ID NO: 14), for example, lysine (+), arginine (+), aspartate (−), glutamate (−), serine, threonine, asparagine, glutamine, and histidine.

According to one embodiment, the hydrophilic block of the ELP diblock copolymer comprises a pentameric amino acid motif of (Val-Pro-Gly-Xaa-Gly)n, wherein n=20-90, and Xaa is Ser or a conservative amino acid substitute thereof, for example, Thr (SEQ ID NO: 16)

According to one embodiment, the hydrophilic block of the ELP diblock copolymer comprises a pentameric amino acid motif of (Val-Pro-Gly-Xaa-Gly)n, wherein n=40-60 (SEQ ID NO: 17).

According to one embodiment, the hydrophobic block of the ELP diblock copolymer comprises a pentameric amino acid motif of (Val-Pro-Gly-Ser-Gly)n, wherein n=20-90, and Xaa is a hydrophobic amino acid, for example, alanine, valine, leucine, isoleucine, proline, phenylalanine, tryptophan, and methionine (SEQ ID NO: 18).

According to one embodiment, the hydrophobic block of the ELP diblock copolymer comprises a pentameric amino acid motif of (Val-Pro-Gly-Xaa-Gly)n, wherein n=20-90, and Xaa is Ile or a conservative amino acid substitute thereof, for example, Leu or Met or Val (SEQ ID NO: 19).

According to one embodiment, the hydrophobic block of the ELP diblock copolymer comprises a pentameric amino acid motif of (Val-Pro-Gly-Xaa-Gly)n, wherein n=40-60 (SEQ ID NO: 17).

According to one embodiment of the described invention, the hemoglobin subunit or fragment is operatively linked to the hydrophobic block of the ELP to facilitate enclosing of hemoglobin or functional equivalent thereof within the core of an ELP nanoparticle.

According to one embodiment, the hemoglobin, subunit(s), fragment(s), derivative(s), or functional equivalent thereof is operatively linked to the C-terminus of the ELP.

According to one embodiment, the hemoglobin, subunit(s), fragment(s), derivative(s), or functional equivalent thereof is operatively linked to a hydrophobic block of the ELP.

According to one embodiment, the hemoglobin, subunit(s), fragment(s), derivative(s), or functional equivalent thereof is operatively linked to the hydrophobic block of the ELP via a chemical reaction.

According to another embodiment, the hemoglobin, subunit(s), fragment(s), derivative(s), or functional equivalent thereof that is operatively linked to the hydrophobic block of the ELP comprises a fusion protein.

According to one embodiment, the specific polynucleotide is contained in a vector and/or host cell.

According to one embodiment, the fusion protein is encoded by a polynucleotide comprising a nucleotide sequence that encodes a recombinant ELP operatively linked to nucleotide sequence that encodes a hemoglobin, a subunit, a fragment, or a functional equivalent thereof.

According to one embodiment, the polynucleotide sequence that encodes the hemoglobin, a subunit, a fragment, or a functional equivalent thereof is selected from the group consisting of SEQ ID NO. 1, SEQ ID NO. 2 and SEQ ID NO. 3.

According to one embodiment, a hemoglobin, a subunit, a fragment, or a functional equivalent thereof comprises an amino acid sequence selected from the group consisting of: SEQ ID NO. 4, SEQ ID NO. 5 and SEQ ID NO. 6.

According to one embodiment, the ELP comprises amino acid sequence SEQ ID NO. 7.

According to one embodiment, the fusion protein comprises an ELP of amino acid sequence SEQ ID NO. 7 operatively linked to one or more hemoglobin subunits of amino acid sequences selected from the group consisting of SEQ ID NO. 4, SEQ ID NO. 5 and SEQ ID NO. 6.

According to one embodiment, the fusion protein comprises amino acid sequence SEQ ID NO. 8 containing an ELP of amino acid sequence SEQ ID NO. 7 operatively linked to a hemoglobin subunit of amino acid sequence SEQ ID NO. 4.

According to one embodiment, the fusion protein comprises amino acid sequence SEQ ID NO. 9 containing an ELP of amino acid sequence SEQ ID NO. 7 operatively linked to a hemoglobin subunit of amino acid sequence SEQ ID NO. 5.

According to one embodiment, the fusion protein comprises amino acid sequence SEQ ID NO. 10 containing an ELP of amino acid sequence SEQ ID NO. 7 operatively linked to a hemoglobin subunit of amino acid sequence SEQ ID NO. 6.

According to one embodiment of the described invention, the pharmaceutical composition comprises a therapeutic amount of a protein polymer-encapsulated hemoglobin molecule.

According to one embodiment, the protein polymer-encapsulated hemoglobin molecule is a fusion protein consisting essentially of a protein polymer operatively linked to a hemoglobin subunit or a fragment, wherein the hemoglobin is encapsulated within the protein polymer.

According to one embodiment, the pharmaceutical composition further comprises one or more pharmaceutically acceptable carriers.

Formulations of pharmaceutical composition may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, the pharmaceutical composition may be administered to a subject parenterally through, e.g. a needle, a cannula, a catheter, and the like.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The protein polymer complex may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof.

The formulations may be presented conveniently in unit dosage form and may be prepared by any of the methods well known in the art of pharmacy.

The pharmaceutical protein polymer—hemoglobin complex or a pharmaceutically acceptable salt, solvate or prodrug thereof may be mixed with other active materials that do not impair the desired action, or with materials that supplement the desired action.

Solutions or suspensions used for parenteral administration may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, exemplary carriers are physiological saline or phosphate buffered saline (PBS).

Pharmaceutical compositions for parenteral administration comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono-or diglycerides. In addition, fatty acids such as oleic acid are used in the preparation of injectables.

Formulations for parenteral administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The polymer-hemoglobin complex may be provided in particles. The term "particles" as used herein refers to nano or microparticles (or in some instances larger) that may contain in whole or in part the hemoglobin or functional equivalent of hemoglobin as described herein. According to one embodiment, the particles can contain the hemoglobin, subunit(s), fragment(s), derivative(s), or functional equivalent thereof in a core surrounded by the polymer. According to one embodiment, the therapeutic complex can be dispersed throughout the particles. According to one embodiment, the therapeutic complex can be adsorbed into the particles. The particles can be of any order release kinetics, including zero order release, first order release, second order release, delayed release, sustained release, immediate release, etc., and any combination thereof. The particle may include, in addition to the therapeutic complex, any of those protein polymers routinely used in the art of pharmacy and medicine, including, but not limited to, erodible, nonerodible, biodegradable, or nonbiodegradable material or combinations thereof. According to one embodiment, the particles may be microcapsules of protein polymers that contain the hemoglobin, subunit(s), fragment(s), derivative(s), or functional equivalent thereof. According to one embodiment, the particles may be of virtually any shape.

The compositions of the present invention may be in the form of a sterile injectable aqueous or oleaginous suspension. Such injectable preparations may be formulated using suitable dispersing or wetting agents and suspending agents.

The sterile injectable preparation also may be a sterile injectable solution or suspension in a nontoxic parenterally acceptable diluent or solvent, for example, as a solution in 1,3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/ or dextran. Optionally, the suspension may also contain stabilizers.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 0.05% w to about 99.95% w, depending on the activity of the drug being employed. According to one embodiment, about 5% w to about 95% will be used. The carrier may be one or a combination of two or more pharmaceutical excipients, but generally will be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the present invention are readily absorbed in the lungs without the need to employ penetration enhancers.

According to some embodiments, the compositions of the described invention may be formulated with an excipient, vehicle or carrier selected from solvents, suspending agents, binding agents, fillers, lubricants, disintegrants, and wetting agents/surfactants/solubilizing agents.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to pregelatinized maize starch, polyvinylpyrrolidone or hydroxypropyl methylcellulose); fillers (including but not limited to lactose and other sugars, microcrystalline cellulose, pectin, gelatin, calcium sulfate, ethyl cellulose, polyacrylates or calcium hydrogen phosphate); lubricants (including, but not limited to magnesium stearate, talc, silica, sollidal silicon dioxide, stearic acid, metallic stearates, hydrogenated vegetable oils, corn starch, polyethylene glycols, sodium benzoate, sodium acetate); disintegrants (including but not limited to starch, sodium starch glycolate) and wetting agents (including but not limited to sodium lauryl sulfate). Additional suitable carriers for the compositions of the present invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

According to some embodiments, the pharmaceutically acceptable carrier of the compositions of the present invention includes a release agent such as a sustained release or delayed release carrier. According to such embodiments, the carrier can be any material capable of sustained or delayed release of the active ingredient to provide a more efficient administration, resulting in less frequent and/or decreased dosage of the active ingredient, ease of handling, and extended or delayed effects. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

Additional compositions of the present invention can be prepared readily using known technology, such as that which is described in Remington's Pharmaceutical Sciences, 18th or 19th editions, published by the Mack Publishing Company of Easton, Pa., which is incorporated herein by reference.

According to some embodiments, the compositions of the present invention can further include one or more compatible active ingredients aimed at providing the composition with another pharmaceutical effect. "Compatible" as used herein means that the active ingredients of such a composition are capable of being combined with each other in such a manner so that there is no interaction that would substantially reduce the efficacy of each active ingredient or the composition under ordinary use conditions.

According to another embodiment of the present invention, the composition may be administered serially or in combination with other compositions for treating conditions of blood loss or anemia or other blood disorders.

An amount adequate to accomplish therapeutic or prophylactic treatment is defined herein as a therapeutically-effective dose. In therapeutic regimes, an amount of the compositions of the described invention is administered until a sufficient beneficial response has been achieved. For example, the response is monitored and repeated dosages are given if the response starts to wane. A skilled artisan can determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the present invention to achieve the desired response, and "maximum efficacy" refers to the maximum achievable effect. The amount of the active complex in the compositions of the described invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, N.Y., 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment, it is preferred that the therapeutic dosage be close to the maximum tolerated dose. For chronic preventive use, lower dosages may be desirable because of concerns about long term effects.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLE

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Construction of Recombinant ELP Genes Encoding for ELPs

To generate ELPs of a specific and pre-determined chain length, the following is an example of a plasmid reconstruction recursive directional ligation (preRDL) strategy can be employed (McDaniel JR, Biomacromolecules. 2010, 11:944-952). Two cloning vectors, which contain an ELP gene are cut with two separate sets of restriction enzymes, as is described previously (Sun G, Journal of controlled release: official journal of the Controlled Release Society. 2011;155:218-226), and two vectors are digested with two sets of restriction enzymes, respectively. The two sets of cut vectors are gel purified and ligated together using an appropriate DNA ligase, resulting in the recursive extension of the genes encoding for pentameric repeats, for example, (VPGXaaG)n, wherein Xaa denotes any amino acid and n denotes the number of repetitive motifs (SEQ ID NO: 11). The same strategy is employed to generate the ELP diblock copolymer, where the N-terminal gene of one monoblock is ligated to a C-terminal ELP gene of another via preRDL. For example, the ELP diblock copolymer comprises one hydrophobic block, comprising (VPGXaaG)n wherein Xaa is one of hydrophobic amino acids, n=40-60 (SEQ ID NO: 17); and one hydrophilic block, comprising (VPGXaaG)n wherein Xaa=one of hydrophilic amino acids, n=40-60 (SEQ ID NO: 20). Gene sequences encoding for the desired polypeptides can be confirmed, for example, using diagnostic DNA digestion and DNA sequencing from both N and C termini.

Exemplary Protocol for the Bacterial Transformation of DNA Containing the Desired Nucleotide Sequence During ligation, Top10/BLR cells (e.g. Life Technologies, Merck Millipore) are removed from the −80° C. fridge and thawed on ice. An aliquot of 125 µL of the Top10/BLR cells is transferred into a fresh tube and an aliquot of 5 µL of DNA ligase is added. The cells in the tube are well mixed by pipetting up and down, and incubated on ice for 5-10 min. The cells in the tube are heat shocked for 1 min at 42° C. (or 3 min at 37° C.), and incubated for 5 min on ice. The cells are plated onto pre-warmed ampicillin plates, and incubated (upside-down) overnight in the 37° C. incubator.

Expression of ELP Genes and Purification of Recombinant ELPs

The expression vectors containing the desired constructs are transformed into E. coli cells for protein hyperexpression and proteins are purified by inverse transition cycling (ITC). (Golemis E, Adams P D. Protein-protein interactions: a molecular cloning manual. Edn. 2nd Cold Spring Harbor Laboratory Press; Cold Spring Harbor, N.Y.: 200532). Briefly, overnight cultures are spun down and re-suspended in cold PBS. The proteins are liberated from bacteria by periodic probe-tip sonication for an appropriate time period. Insoluble debris is collected by centrifugation for at 4° C. for an appropriate time period, and the supernatant is transferred to another tube. Excess poly-ethylene imine (PEI) (MW=3,000) is added to precipitate nucleic acids and the solution is centrifuged. The supernatant, containing soluble ELP, is purified using about 4-6 rounds of inverse transition cycling (ITC). For each round, the supernatant is heated to 37° C. to induce phase separation, and the coacervate is collected by centrifugation. The ELP is then re-suspended in cold PBS and centrifuged at 4° C. again, completing one round of ITC. About 4-6 rounds of ITC are sufficient to ensure the purity.

Exemplary Protocol for the Purification of ELPs

An aliquot of 125 µl of BLR cells is transferred into a fresh tube and thawed on ice. An aliquot of 1 µl of miniprep plasmid is transferred into the tube, which contains the freshly thawed BLR cells (E. coli strain preferred for protein expression) on ice. The tube containing miniprep plasmid and BLR cells is kept on ice for ~10 min, then moved onto a heat block to heat at 42° C. for 1 min; and then moved into an ice bath and kept for 5 min. The cells with recombinant DNA plasmids are then plated on Amp plates and are incubated overnight upside down.

One colony is selected from the overnight Amp plate, transferred into an Erlenmeyer flask, which contains 50 ml of TB media with 50 µl ampicillin, and then left overnight in a shaking incubator at 37° C. and 250 rpm. 0.75 ml of the overnight culture is added to 0.75 ml DMSO solution to make a DMSO stock of the overnight culture. The DMSO stock is stored at −80° C. The rest of the culture is centrifuged at 3000 rpm, 4° C. for 10 minutes to sediment the bacteria. The bacteria pellet is re-solubilized with an aliquot of 5 ml of media and well mixed by pipetting up and down. An aliquot of 500 µl of re-suspended pellet is inoculated into a one liter (1 L) culture media in a 4 liter Erlenmeyer flask, to which an aliquot of 1 ml of ampicillin is added. The Erlenmeyer flask is then left overnight in a shaking incubator at 37° C. and 250 rpm.

After overnight incubation, the culture is centrifuged at 3000 rpm and 4° C. for 10 min to separate the bacteria containing the ELP from the supernatant. The supernatant is discarded. The pellet is transferred into a 50 ml conical tube (Falcon tube), which contains 40 ml of cold PBS to re-suspend and form a suspension, which is then vortexed. The conical flask is then put in a plastic beaker, which contains ice and a little bit of water and is sonicated according to the following time sequence to generate a lysed product, (i.e., 10 secs on, 20 secs off, repeat cycle for 3 mins).

The lysed product is transferred from the Falcon tube to an Oakridge tube and then is cold spin sonicated at 12,000 rpm, 4° C., for 15 min. The supernatant is transferred to a 50 ml Falcon tube and the pellet, which contains insoluble cellular debris, is discarded. PEI is added to the supernatant to a final concentration of 0.5% and mixed gently. The solution is then incubated for 10-20 min on ice, with occasional gentle mixing, and then centrifuged at 12,000 rpm for 15 min at 4° C. The supernatant is transferred to a new centrifuge tube (Falcon tube); the pellet, which contains precipitated DNA and insoluble cellular debris, is discarded. The supernatant is placed in a 37° C. water bath for 10 min, and then, about 2.6 g of NaCl (1M of NaCl in ~45 ml) is added to the supernatant. The supernatant is then spun at 37° C., 4000 rpm for 10 min. The supernatant is removed and the pellet is re-suspended on ice in 15 ml of cold PBS; the supernatant is then transferred to the Oakridge tube and re-suspended in 5 ml of PBS first, and then washed out with 10 ml of PBS. The suspension is then spun at 12,000 rpm, 4° C., for 10 min to remove any remaining insoluble matter. The supernatant is retained and any pellet formed is discarded.

One exemplary ELP diblock copolymer comprises one hydrophobic block, comprising (VPGXaaG)n wherein Xaa is Ile and n=48 (SEQ ID NO: 21); and one hydrophilic block, comprising (VPGXaaG)n wherein Xaa=Ser and n=48 (SEQ ID NO: 22). The amino acid sequence of the exemplary ELP diblock copolymer is shown as SEQ ID NO. 7.

ELP Spherical Nanoparticles Possessing Hemoglobin, a Subunit(s), a Fragment(s), a Derivative(s), or a Functional Equivalent Thereof at the Core of ELP Via Noncovalent Attractions Hemoglobin, a subunit(s), a fragment(s), a derivative(s), or a functional equivalent thereof is mixed with the recombinant ELP based on a 1:1 molar ratio at a 7.4±0.3 pH in PBS buffer to form an ELP-hemoglobin complex, where the ELP and the hemoglobin, subunit(s), fragment(s), derivative(s), or functional equivalent thereof are held together by noncovalent attractions, for example, salt bridge, hydrogen bonds, and/or a hydrophobic effect.

The amino acid sequences of exemplary hemoglobin subunit(s) are SEQ ID NO. 4, SEQ ID NO. 5 and SEQ ID NO. 6. The amino acid sequence of an exemplary ELP is SEQ ID NO. 7.

Fusion Protein Formed by Chemical Reaction of ELP with Hemoglobin, a Subunit(s), a Fragment(s), a Derivative(s), or a Functional Equivalent Thereof Hemoglobin, a subunit(s), a fragment(s), a derivative(s), or a functional equivalent thereof is mixed with the recombinant ELP based on 1:1 molar ratio at a 7.4±0.3 pH in PBS buffer. The reaction is kept at 4° C. overnight. Size-exclusion chromatography is used to remove unreacted reagents from the fusion protein consisting of ELP operatively linked to the hemoglobin, subunit(s), fragment(s), derivative(s), or functional equivalent thereof.

The amino acid sequences of exemplary hemoglobin subunit(s) are SEQ ID NO. 4, SEQ ID NO. 5, and SEQ ID NO. 6. The amino acid sequence of exemplary ELP is SEQ ID NO. 7.

Construction of Fusion Genes Encoding for Fusion Proteins

The gene encoding human hemoglobin, subunit(s), fragment(s), derivative(s), or functional equivalent thereof is inserted into a cloning vector, which is linearized. The nucleotide sequence of the exemplary hemoglobin subunit(s) is selected from the group consisting of SEQ ID. NO. 1, SEQ ID. NO. 2, and SEQ ID. NO. 3. A cassette for the ELP gene encoding ELP diblock copolymer (VPGXaaG)n comprising a hydrophobic block, wherein Xaa is one of hydrophobic amino acids (SEQ ID NO: 23); and a hydrophilic block, wherein Xaa is one of hydrophilic amino acids, is removed from the cloning vector by double digestion, followed by electrophoretic separation and agarose gel extraction. The ELP cassette is then ligated into the linearized vector operatively linked to a nucleotide sequence encoding a hemoglobin subunit. The fusion gene cassette is then removed by double digestion, followed by electrophoretic separation and agarose gel extraction. Separately, an expression vector is double digested, treated, agarose gel purified, and then ligated with the fusion gene cassette to yield the target fusion gene (ELP-hemoglobin) in an expression vector. The expression vector containing the target fusion gene (ELP-hemoglobin) is transformed into an expression strain of E.coli.

Expression of Fusion Genes and Purification of Fusion Proteins

An appropriate amount of media with appropriate concentration of antibiotics, for example, ampicillin is inoculated with the expression strain and grown using a hyper expression protocol. (Daniell H, et al., Methods Mol Biol 1997, 63:359-371). Overnight cell cultures are spun down and re-suspended in cold PBS. Cells are harvested by centrifugation, re-suspended in cold PBS, lysed by probe-tip sonication at 4° C., and centrifuged at 4° C. to eliminate insoluble cell debris. The supernatant containing soluble fusion protein is transferred to another tube, nucleic acids are precipitated using polyethyleneimine (PEI) and removed by centrifugation at 4° C.

Fusion protein (containing ELP-hemoglobin) is purified by 4-6 rounds of inverse transition cycling (ITC) as described previously (McPherson D T, et al., Protein Expr Purif 1996, 7(1):51-57). Briefly, for one round of ITC, the supernatant, containing the soluble fusion protein is heated to induce phase separation, and the coacervate is collected by centrifugation. The fusion protein is then re-suspended in cold PBS and re-centrifuged at 4° C.

To confirm fusion protein purity, for example, SDS-PAGE can be performed. To determine concentrations of fusion protein, for example, the concentration can be determined spectrophotometrically using calculated extinction coefficients (Gill S, et al., Analytical Biochemistry 1989, 182: 319-326).

The amino acid sequences of the exemplary fusion proteins are presented as SEQ ID NO. 8, SEQ ID NO. 9, and SEQ ID NO. 10. For example, the fusion protein is of amino acid sequence SEQ ID No. 8 comprising an ELP amino acid sequence SEQ ID No. 7 operatively linked to a hemoglobin amino acid sequence SEQ ID No. 4. The fusion protein of amino acid sequence SEQ ID No. 9 comprises an ELP amino acid sequence SEQ ID No. 7 operatively linked to a hemoglobin amino acid sequence SEQ ID No. 5. The fusion protein of amino acid sequence SEQ ID No. 8 comprises an ELP amino acid sequence SEQ ID No. 7 operatively linked to a hemoglobin amino acid sequence SEQ ID No. 6. According to some embodiments, a linking peptide (Yaa)m resides between the ELP amino acid sequence and hemoglobin amino sequence, wherein Yaa specifies any amino acid and m denotes a number of repetitive amino acids.

Isolation of Plasmid DNA Containing ELP-Hemoglobin Fusion Gene

Plasmid DNA containing an ELP-hemoglobin fusion gene can be isolated, for example, using a Qiagen minprep kit according to manufacturer's protocol. Briefly, plastic culture tubes are filled with 4 mL of autoclaved TB media and inoculated with a bacterial colony transformed with plasmid DNA containing an ELP-hemoglobin fusion gene. Next, the inoculated tubes are incubated overnight at 37° C. in a shaker incubator. The next day, four, 1.5 mL tubes and 1 filter are labeled for each colony selected. After incubating overnight, 0.5 mL aliquots are removed from the inoculated tubes and are transferred to the newly labeled 1.5 mL tubes. The inoculated tubes are centrifuged for 10 minutes at 4,000 rpm. After centrifugation, supernatant is discarded, the pellets are resuspended in 250 µL Buffer P1 (Qiagen, Valencia, Calif.), and the resuspended pellets are transferred to a 1.5 mL microfuge tube. Next, 250 µL Buffer P2 (Qiagen, Valencia, Calif.) is added to the microfuge tube containing Buffer P1 and the tube is inverted 4-6 times. After inversion, 350 µL Buffer N3 (Qiagen, Valencia, Calif.) is added to the microfuge tube containing Buffer P1 and Buffer P2 and the tube is inverted 4-6 times. Following inversion, the microfuge tube is centrifuged in a table-top centrifuge for 10 minutes at 13.2 rpm. After centrifugation, the supernatant is poured into the appropriate pre-labeled filter and centrifuged in a table-top centrifuge for 0.5 minutes at 13.2 rpm. After centrifugation, the flow-through is discarded and 750 µL Buffer PE (Qiagen, Valencia, Calif.) is added to the filter and the filter is centrifuged in a table-top centrifuge or 0.5 minutes at 13.2 rpm. The flow-through is dicared and the filter is centrifuged in a table-top centrifuge or 0.5 minutes at 13.2 rpm. After centrifugation, the top half of filter is placed in the appropriate pre-labeled microfuge tube; the bottom half of the filter is discarded. Next, 50 µL of autoclaved water is added to the filter and the filter is incubated at room temperature for 2-3 minutes before centrifuging in a table-top centrifuge or 0.5 minutes at 13.2 rpm. After centrifugation, the flow-through is collected and the filter is discarded. An optical density (OD) measurement at 280 nm can be performed on the flow-through to determine plasmid DNA concentration.

Expression of ELP-Hemoglobin Fusion Protein

ELP-hemoglobin fusion protein can be expressed, for example, by *E. coli* BLR cells using the following exemplary protocol. Briefly, 125 µL of freshly thawed BLR cells are transformed with 1 µL of isolated plasmid containing an ELP-hemoglobin fusion gene by incubating on ice for 10 minutes, in a 42° C. heat block for 1 minute and on ice for 5 minutes. Following transformation, the BLR cells are plated on an ampicillin (Amp) agar plate and incubated upsided down overnight. Following overnight incubation, one colony is selected from the Amp agar plate and is placed in Erlenmyer flask containing 50 mL of TB media and 50 µL of ampicillin. The flask is incubated overnight in a shaker incubator at 37° C. and 250 rpm. After overnight incubation, a DMSO stock of the culture is prepared by adding 0.75 mL of culture to 0.75 mL DMSO. The DMSO stock is then placed in a −80° C. freezer. The remaining overnight culture is centrifuged at 3,000 rpm at 4° C. for 10 minutes. Supernatant is discarded and the pellet is resuspended in 5 mL TB media. Next, 500 µL of the resuspended culture is used to inoculate a 4 L Erlenmeyer flask containing 1 L of TB media and 1 mL ampicillin. The inoculated flask is incubated overnight in a shaker incubator at 37° C. and 250 rpm. Next, the overnight culture is centrifuged at 3,000 rpm, at 4° C. for 10 minutes. The supernatant is discarded, the cell pellet is resuspend with 40 mL cold PBS, vortexed and sonicated to lyse the cells. The lysed cells are placed in an ice bath for 10 seconds, removed from the ice for 20 seconds and this cycle is repeated for a total of 3 minutes. The lysed cells are transferred to an Oakridge tube and centrifuged at 12,000 rpm at 4° C. for 15 minutes. After centrifugation, the pellet is discarded and the supernatant is transferred to a 50 mL conical tube. Polyethyleneimine (PEI) is added to the supernatant at a final concentration of 0.5% and gently mixed. The supernatant is then incubated on ice for 10-20 minutes, with occasional gentle mixing. After incubation, the supernatant is centrifuged at 12,000 rpm for 15 minutes at 4° C. After centrifugation, the pellet is discarede and the supernatant is transferred to new 50 mL conical tube. The supernatant is placed in a 37° C. water bath, 2.6 g of NaCl is added, and the supernatant is incubated for 10 minutes. Following incubation, the supernatant is centrifuged at 4,000 rpm for 10 minutes at 37° C. The supernatant is discarded and the pellet is resuspended on ice in 15 mL of cold PBS. The resuspended pellet is transferred to an Oakridge tube and centrifuged at 12,000 rpm for 10 minutes at 4° C. The pellet is discarded and the supernatant is retained. Again, the supernatant is placed in a 37° C. water bath, 2.6 g of NaCl is added, and the supernatant is incubated for 10 minutes. Following incubation, the supernatant is centrifuged at 4,000 rpm for 10 minutes at 37° C. The supernatant is discarded and the pellet is resuspended on ice in 15 mL of cold PBS. The resuspended pellet is transferred to an Oakridge tube and centrifuged at 12,000 rpm for 10 minutes at 4° C. The pellet is discarded and the supernatant is retained.

Chemical Conjugation of Elastin-Like Protein (ELP) to Hemoglobin

ELP was conjugated to hemoglobin using a 1-Ethyl-3-(3-dimethylaminopropyl) carbodiimide (EDC) based linker according to the manufacturer's (Thermo Scientific, Grand Island, N.Y.) protocol.

Briefly, a 10-fold molar excess of EDC (Thermo Scientific, Product Number 22980) was added directly to hemoglobin (Sigma-Aldrich, Catalog Number H7379). Next, 0.6 mg of N-hydroxysuccinimide (NHS) was added to the EDC and hemoglobin, the components were mixed and allowed to react for 15 minutes at room temperature. After the 15 minute reaction, ELP expressed in *E. coli* (as described above) was added to the hemoglobin reaction mixture to produce hemoglobin:ELP ratios of 2:1, 1; 1 and 1:4. Next, the ELP and hemoglobin reaction mixture was incubated for 2 hours at room temperature. After the 2 hour incubation, the reaction was quenched by adding hydroxylamine to a final concentration of 10 mM.

SDS-PAGE of ELP-Hemoglobin Fusion Proteins

ELP-hemoglobin fusion was assessed by sodium dodecyl sulfate polyacrylamide gel electrophoresis (SDS-PAGE).

Briefly, ELP-hemoglobin samples containing hemoglobin:ELP ratios of 2:1, 1:1 and 1:4 were mixed with 1× Sample Buffer (62.5 mM Tris HCl, pH 6.8 at 25° C.; 2% w/v SDS; 10% Glycerol; 50 mM DTT; 0.01% w/v Bromophenol Blue). Approximately 20 ug of each ELP-hemoglobin protein was resolved (125V, 30-40 mA) on a SDS-PAGE gel (Thermo Scientific, Grand Island, N.Y.). Next, the gel was washed 2×5 minutes in ultrapure water, fixed 2×15 minutes in 30% ethanol: 10% acetic acid solution, and washed 2×5 minutes in 10% ethanol then 2×5 minutes in ultrapure water. After the gel was fixed and washed, the gel was sensitized for 1 minute in Silver Stain Sensitizer (Thermo Scientific, Product Number 24612) and then washed 2×1 minute with water. Next, the gel was stained in Silver Stain Working Solution (0.5 mL enhancer with 25 mL Stain) (Thermo Scientific, Product Number 24612) for 30 minutes. After the gel was stained, the gel was washed 2×20 seconds with ultrapure water and developed for 2-3 minutes (or until bands appear) using Developer Working Solution (0.5 mL Enhancer with 25 mL Developer) (Thermo Scientific, Product Number 24612). Finally, the developing reaction was stop by adding 5% acetic acid for 10 minutes.

Figure 6:
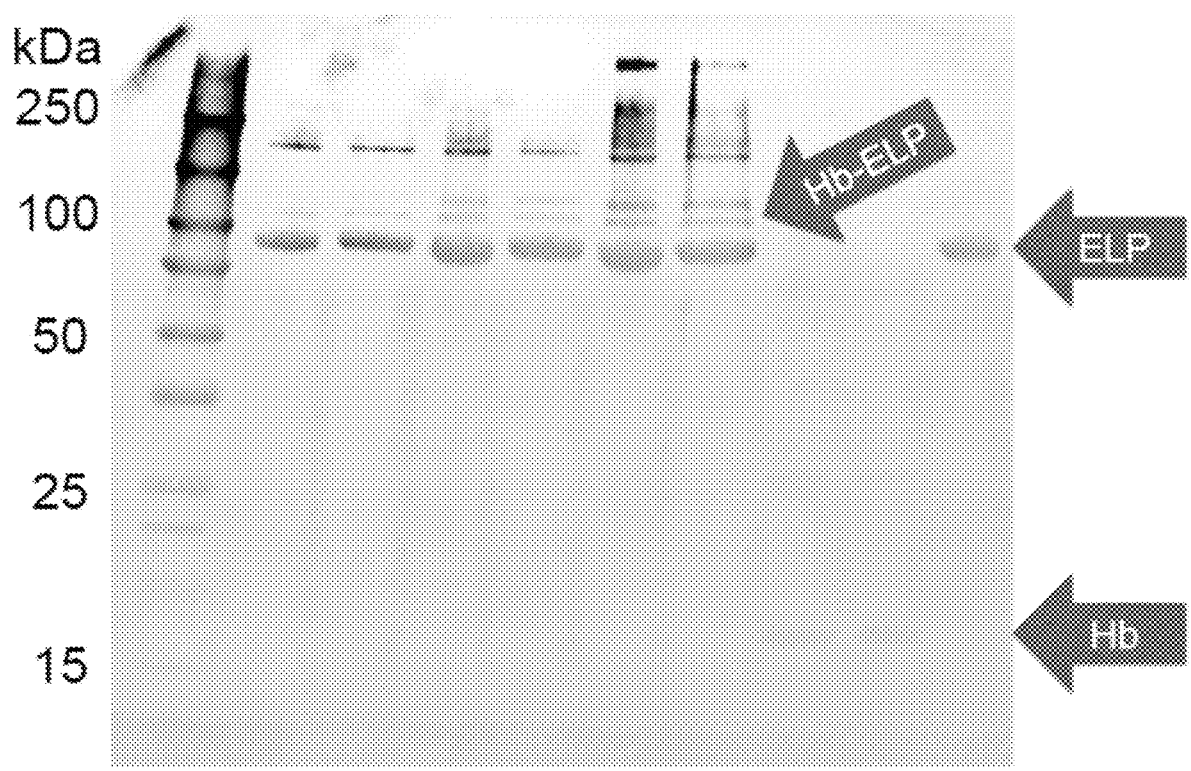
FIG. 6 shows SDS-PAGE of ELP-hemoglobin fusions. M: molecular weight ladder; Lanes 1-2: ELP-hemoglobim fusion (2:1 ratio of hemoglobin:ELP); Lanes 3-4: ELP-hemoglobin fusion (1:1 ratio of hemoglobin:ELP); Lanes 5-6: ELP-hemoglobin fusion (1:4 ratio of hemoglobin:ELP); Lanes 7-8: hemoglobin; Lanes 9-10: ELP.

FIG. 6 shows the results SDS-PAGE. Without being bound by theory, the two protein bands directly above the ELP bands in lanes 1-6 are believe to correspond to ELP binding either one subunit or two subunits of hemoglobin.

Size Exclusion Analysis of ELP-Hemoglobin

Size exclusion analysis was performed on ELP-hemoglobin obtained by the chemical conjugation method described above.

Briefly, ELP-hemoglobin (1:4 ratio of hemoglobin:ELP) was injected/loaded onto a size exclusion column using a BioLogic DuoFlow Chromatography System (Bio-Rad, Hercules, Calif.). The load/injection parameters were as follows:

Static Loop

Buffer A: 100% (1×PBS)/Buffer B: 0% (ddH$_2$O) 20 mL (4× of sample loop volume)/2.60 mL/min.

Once the ELP-hemoglobin sample was loaded on the column, the sample was run through the column using the following parameters:

Isocratic Flow; Buffer A: 100%/Buffer B: 0%; 480 mL/2.60 mL/min.

Isocratic Flow; Buffer A: 0%/Buffer B: 100%; 850 mL/2.60 mL/min.

Isocratic Flow; buffer A: 100%/Buffer B: 0%; 350 mL/2.60 mL/min.

Once a peak was observed, samples were collected using a fraction collector.

Figure 7:
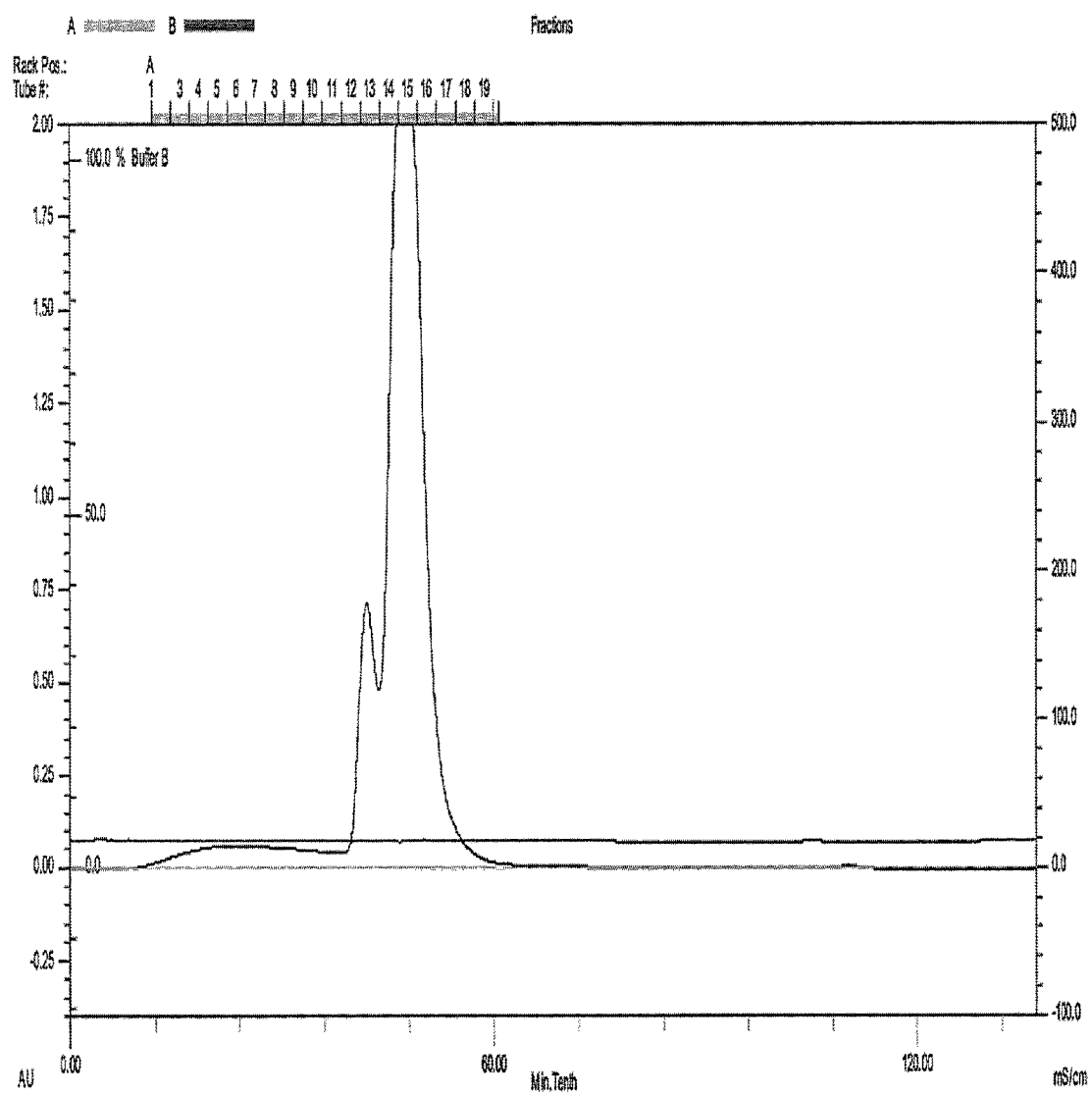
FIG. 7 shows a chromatogram of a size exclusion analysis of an ELP-hemoglobin fusion (1:4 ratio of hemoglobin:ELP). The first peak (Fraction 1) is ELP-hemoglobin fusion. The second peak (Fraction 2) is ELP.

FIG. 7 shows the chromatogram of the size exclusion analysis performed on the ELP-hemoglobin fusion protein (1:4 ratio of hemoglobin:ELP). The first peak (Fraction 1) is ELP-hemoglobin fusion. The second peak (Fraction 2) is ELP.

Dynamic Light Scattering (DLS) Analysis

A dynamic light scattering (DLS) instrument (Wyatt Technology, Santa Barbara, Calif.) was used to measure the hydrodynamic radium of the two fractions (Fraction 1 and Fraction 2) collected by size exclusion analysis.

Figure 8:
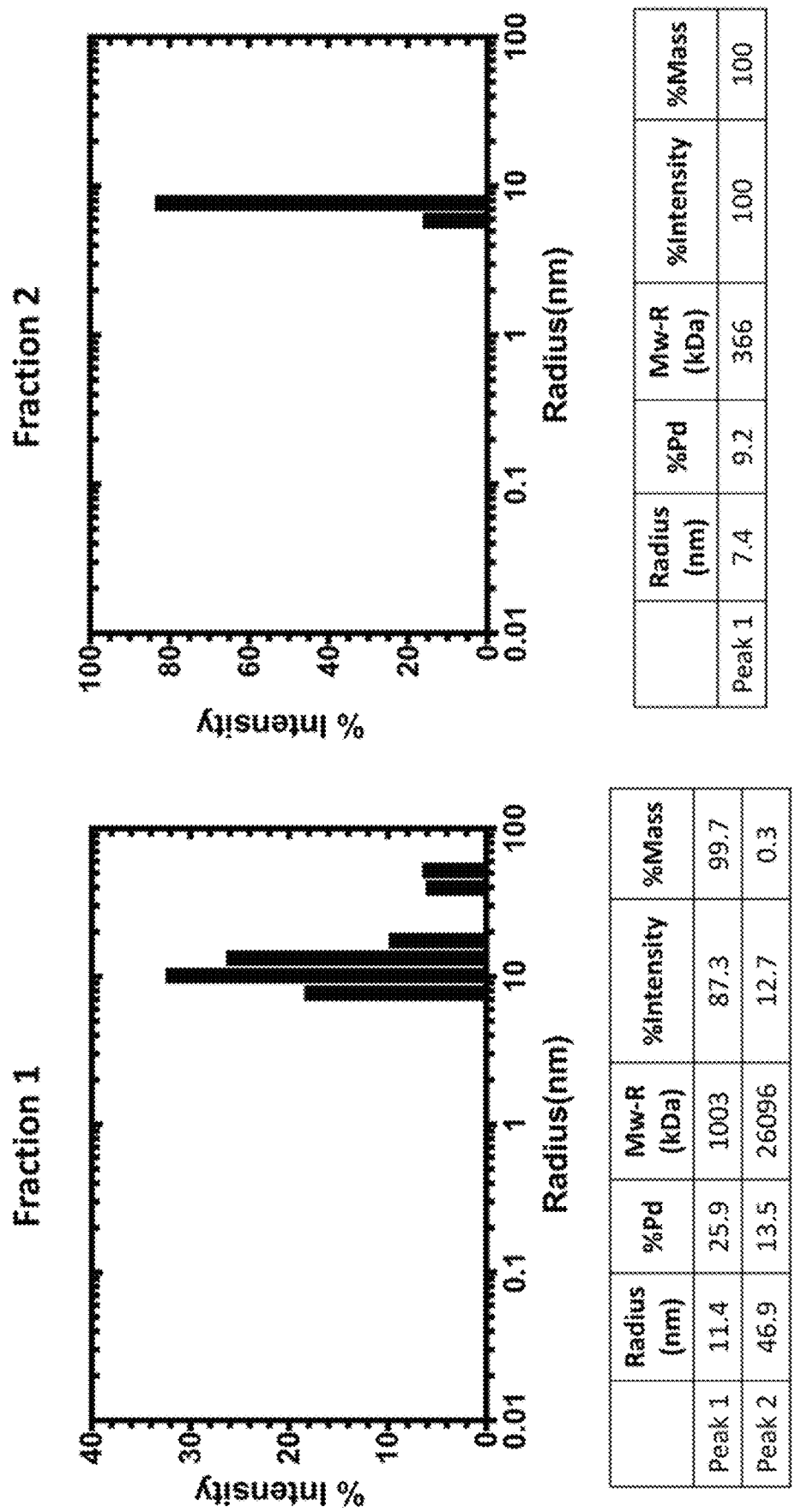
FIG. 8 shows a bar graph (intensity (%) vs. radium (nm)) of dynamic light scattering (DLS) results for Fraction 1(first peak) and Fraction 2 (second peak) of the size exclusion analysis shown in FIG. 7. Hydrodynamic radius of Fraction 1=11.4 nm. Hydrodynamic radius of Fraction 2=7.4 nm.

FIG. 8 shows a bar graph (intensity (%) vs. radium (nm)) of dynamic light scattering (DLS) results for Fraction 1(first peak) and Fraction 2 (second peak) collected by size exclusion analysis. The hydrodynamic radius of Fraction 1 was equal to 11.4 nm. The hydrodynamic radius of Fraction 2 was equal to 7.4 nm.

Figure 9:
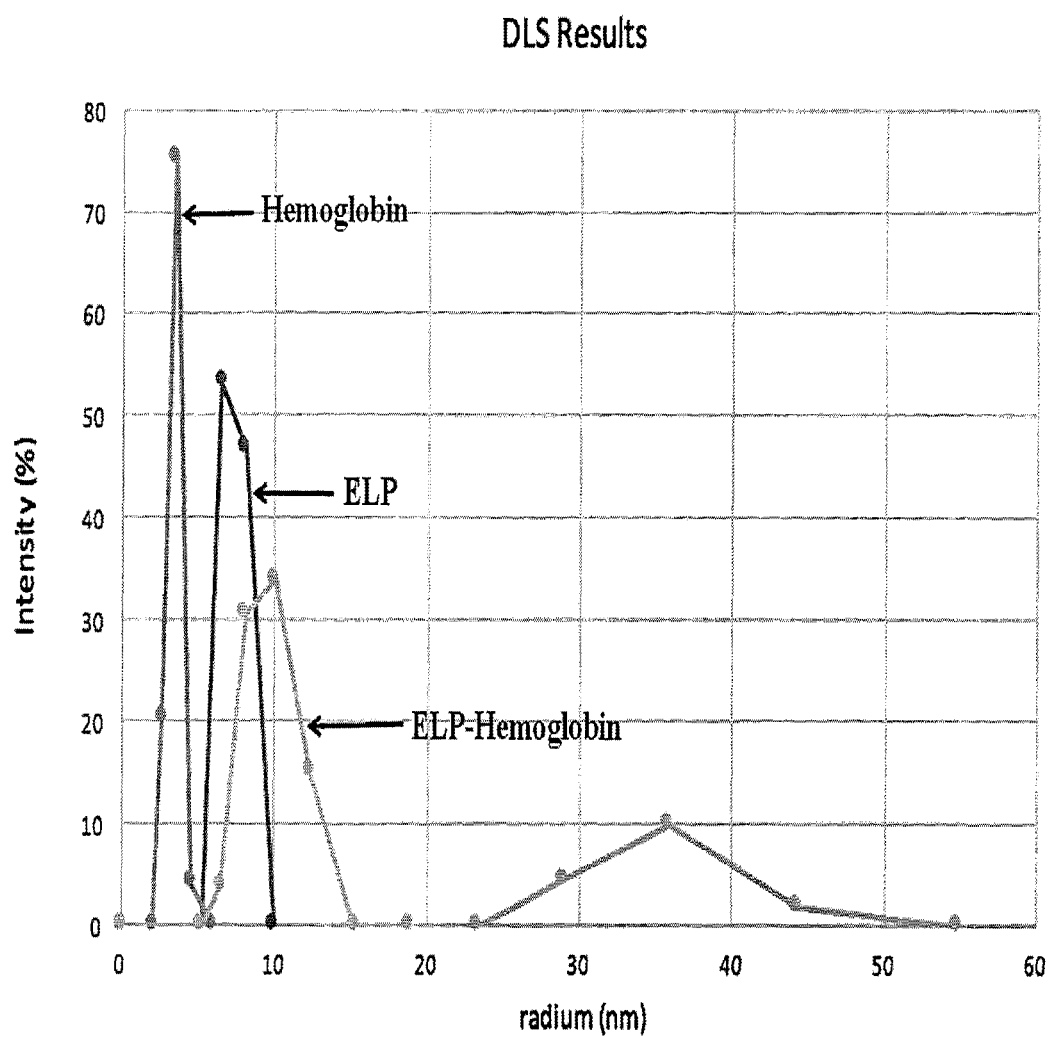
FIG. 9 shows a line graph (intensity (%) vs. radium (nm)) of dynamic light scattering (DLS) results for hemoglobin, ELP and ELP-hemoglobin fusion.

FIG. 9 shows a line graph (intensity (%) vs. radium (nm)) of the dynamic light scattering (DLS) results for the ELP-hemoglobin fusion protein. An increase in hydrodynamic radius of the ELP-hemoglobin fusion is observed when compared to hemoglobin and to ELP.

UV-Vis Characterization

UV-vis was used to determine whether absorption at 400 nm by hemoglobin was maintained in Fraction 1 (first peak/ELP-hemoglobin) collected by size exclusion analysis.

Briefly, both the visible lamp and the UV lamp of a scanning spectrophotometer (Beckman Coulter, Fullerton, Calif.) were switched on to warm. Next, the analysis method was set to "Wavelength Scan II". A cuvette containing blank solvent was placed in the first position of the cuvette holder. Cuvettes containing hemoglobin, Fraction 1 (first peak/ELP-hemoglobin) and Fraction 2 (second peak/ELP) were placed in positions 2, 3 and 4 respectively. The instrument was blanked using the blank solvent cuvette and then the cuvettes containing hemoglobin, Fraction 1 and Fraction 2 were scanned over a series of wavelengths ranging from 200 nm to 800 nm.

Figure 10:
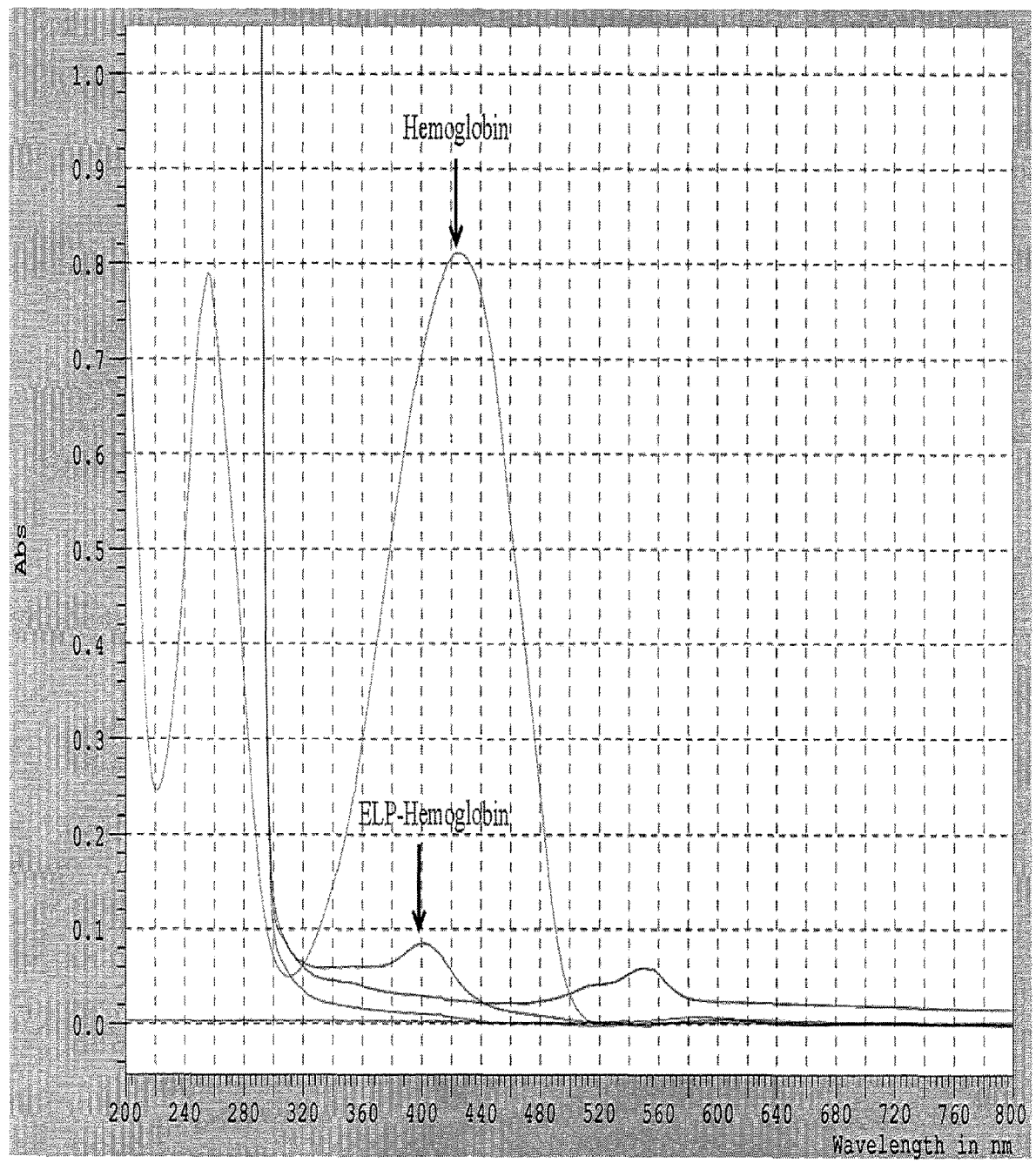
FIG. 10 shows UV-vis results (absorbance vs. wavelength in nm) for Fraction 1 (first peak) and Fraction 2 (second peak) of the size exclusion analysis shown in FIG. 7. The UV-vis results indicate that 400 nm absorption of hemoglobin was maintained after ELP modification.

FIG. 10 shows the UV-vis results (absorbance vs. wavelength in nm) for hemoglobin, Fraction 1 (first peak) and Fraction 2 (second peak). These results indicate that 400 nm absorption of hemoglobin was maintained after ELP modification.

Phase Separation of ELP

An important property of ELP is its ability to undergo phase separation. That is, below a critical transition temperature, ELP is a soluble unimer in aqueous solution, whereas above its transition temperature, ELP undergoes a phase transition and aggregates into an insoluble coacervate (Urry D W, J. Phys. Chem. B. 1997; 101: 11007-11028). Because the fusion of ELP to a protein can alter the phase behavior of ELP, phase separation of Fraction 1 (first peak/ELP-hemoglobin) and Fraction 2 (second peak/ELP) was measured by temperature-programmed turbidimetry. Briefly, light attenuation of Fraction 1 and Fraction 2 collected by size exclusion analysis was monitored at 350 nm as the temperature was ramped at a rate of 1° C./min.

Figure 11:
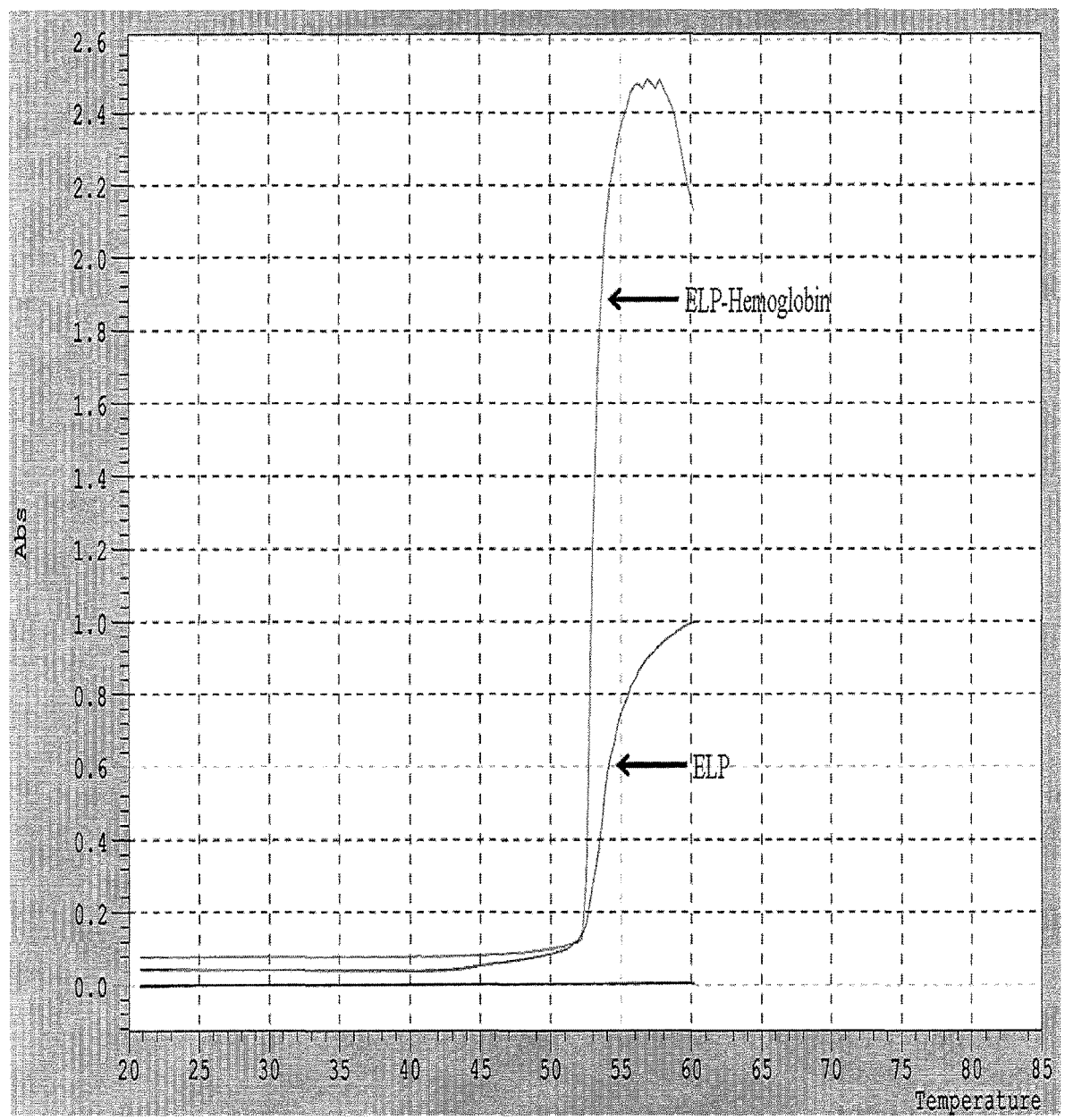
FIG. 11 shows phase separation results (absorbance at 350 nm vs. Temperature in ° C.) for Fraction 1 (first peak) and Fraction 2 (second peak) of the size exclusion analysis shown in FIG. 7. The phase separation results indicate that ELP phase separation is maintained after ELP-hemoglobin fusion.

FIG. 11 shows the phase separation results (absorbance at 350 nm vs. Temperature in ° C.) for Fraction 1 (first peak/ELP-hemoglobin) and Fraction 2 (second peak/ELP) collected by size exclusion analysis. The phase separation results indicate that ELP phase separation is maintained after ELP-hemoglobin fusion.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

---

What is claimed is:

1. A biocompatible pharmaceutical composition comprising a therapeutic amount of a complex comprising an elastin-like polypeptide (ELP) operatively linked via fusion to a hemoglobin (Hb), a Hb subunit(s), a Hb fragment(s), or a Hb derivative(s) comprising the amino acid sequence selected from SEQ ID NO:4, SEQ ID NO: 5 or SEQ ID NO:. 6, that stores and releases oxygen in accordance with an oxygen dissociation curve; wherein the therapeutic amount of the complex is effective to treat a condition caused by blood loss, anemia, or a hemoglobin disorder, and to improve subject survival relative to a control, wherein the ELP comprises:
- a hydrophilic block comprising a pentameric amino acid motif (Val-Pro-Gly-Xaa-Gly)n, wherein n=20-90, and Xaa is a hydrophilic amino acid; and
- a hydrophobic block comprising a pentameric amino acid motif (Val-Pro-Gly-Xaa'-Gly)n, wherein n=20-90, and Xaa' is a hydrophobic amino acid.

2. The biocompatible pharmaceutical composition of claim 1, wherein the ELP is assembled into a spherical nanoparticle comprising a core into which the Hb, the Hb subunit(s), the Hb fragment(s), or the Hb derivative(s) is encapsulated.

3. The biocompatible pharmaceutical composition of claim 1, wherein the ELP comprises a pentameric amino acid motif (Val-Pro-Gly-Xaa-Gly)n, wherein n=20-90, and Xaa is Ser or Ile, or a conservative amino acid substitute thereof.

4. The biocompatible pharmaceutical composition of claim 3, wherein the conservative amino acid substitute of Ser is Thr.

5. The biocompatible pharmaceutical composition of claim 3, wherein the conservative amino acid substitute of Ile is Leu, Met, or Val.

6. The biocompatible pharmaceutical composition of claim 1, wherein for the hydrophilic block, the Xaa is selected from the group consisting of Lys, Arg, Asp, Glu, Ser, Thr, Asn, Gln, and His; and for the hydrophobic block, Xaa' is selected from the group consisting of Ala, Val, Leu, Ile, Pro, Phe, Trp, and Met.

7. The biocompatible pharmaceutical composition of claim 6, wherein for the hydrophilic block the Xaa is Ser or a conservative amino acid substitute thereof;
and for the hydrophobic block the Xaa' is Ile or a conservative amino acid substitute thereof.

8. The biocompatible pharmaceutical composition of claim 7, wherein the conservative amino acid substitute of Ser is Thr; and the conservative amino acid substitute of Ile is Leu, Met or Val.

9. The biocompatible pharmaceutical composition of claim 1, wherein n=48 for hydrophobic block and n=48 for hydrophilic block.

10. The biocompatible pharmaceutical composition of claim 1, wherein the Hb, the Hb fragment(s), or the Hb derivative(s) is operatively linked to the C-terminus of the ELP.

11. The biocompatible pharmaceutical composition of claim 1, wherein the Hb, the Hb subunit(s), the Hb fragment(s), or the Hb derivative(s) is operatively linked to the hydrophobic block of the ELP.

12. The biocompatible pharmaceutical composition of claim 1, wherein the ELP comprises the amino acid sequence SEQ ID NO: 7.

13. The biocompatible pharmaceutical composition of claim 1, wherein the Hb, the Hb subunit(s), the Hb fragment(s), or the Hb derivative(s) comprises one or more pharmaceutically acceptable salts thereof.

14. A method of treating a condition due to blood loss and improving subject survival, the method comprising: administering a therapeutic amount of the biocompatible pharmaceutical composition of claim 1 to the subject in need thereof.

* * * * *